United States Patent
Han

(10) Patent No.: US 12,065,444 B2
(45) Date of Patent: Aug. 20, 2024

(54) SUBSTITUTED TETRAZOLO[1,5-A]PYRAZINES AND TETRAZOLO[1,5-C]PYRIMIDINES AS ADENOSINE RECEPTOR ANTAGONISTS

(71) Applicant: Crossignal Therapeutics, Inc., La Jolla, CA (US)

(72) Inventor: Sangdon Han, La Jolla, CA (US)

(73) Assignee: Crossignal Therapeutics, Inc., La Jolla, CA (US)

( * ) Notice: Subject to any disclaimer, the term of this patent is extended or adjusted under 35 U.S.C. 154(b) by 0 days.

(21) Appl. No.: 17/989,584

(22) Filed: Nov. 17, 2022

(65) Prior Publication Data

US 2023/0159541 A1    May 25, 2023

Related U.S. Application Data

(60) Provisional application No. 63/281,445, filed on Nov. 19, 2021.

(51) Int. Cl.
  *A61K 31/4985* (2006.01)
  *A61K 31/519* (2006.01)
  *C07D 487/04* (2006.01)
  *C07D 519/00* (2006.01)

(52) U.S. Cl.
  CPC ......... *C07D 487/04* (2013.01); *C07D 519/00* (2013.01)

(58) Field of Classification Search
  CPC . A61K 31/4985; A61K 31/519; C07D 487/04
  USPC ............. 514/249, 261.1; 544/254, 350
  See application file for complete search history.

(56) References Cited

U.S. PATENT DOCUMENTS 8,569,300 B2 * 10/2013 Borchardt ............... A61P 37/06
                                                  514/249
2021/0061809 A1    3/2021 Han et al.

FOREIGN PATENT DOCUMENTS

WO    WO 2011/112766    9/2011
WO    WO 2013/039785    3/2013
WO    WO 2019/168847    9/2019

OTHER PUBLICATIONS

Cocco et al., "Transformation of 6-methylthiopyrimidines. Preparation of new pyrimidine derivatives and fused azolopyrimidines," Journal of Heterocyclic Chemistry, Jul. 2000, 37(4):707-710.
Dziedzic et al., "Release of adenosine-induced immunosuppression: Comprehensive characterization of dual A2A/A2B receptor antagonist," Int. Immunopharmacol., Jul. 2021, 96, 107645, 12 pages.
Fathalla et al., "Novel 2-thiopyrimidine derivatives as CDK2 inhibitors: molecular modeling, synthesis, and anti-tumor activity evaluation," Medicinal Chemistry Research, Apr. 2012, 22(2):659-673.
Fishman et al., "Adenosine Receptors and Cancer," Handb. Exp. Pharmacol., May 2009, 193:399-441, 44 pages.
Franco et al., "Adenosine Receptor Antagonists to Combat Cancer and to Boost Anti-Cancer Chemotherapy and Immunotherapy," Cells, Oct. 2021, 10(11), 2831, 13 pages.
International Search Report and Written Opinion in International Appln. No. PCT/US2022/050311, mailed Feb. 14, 2023, 17 pages.
Jamwal et al., "Therapeutic Potential of Agonists and Antagonists of A1, A2a, A2b and A3 Adenosine Receptors," Curr. Pharm. Des., 2019, 25(26):2892-2905, 15 pages.

* cited by examiner

*Primary Examiner* — Douglas M Willis
(74) *Attorney, Agent, or Firm* — Fish & Richardson P.C.

(57)  ABSTRACT

Provided herein are substituted tetrazolo[1,5-a]pyrazines and tetrazolo[1,5-c]pyrimidines useful for the treatment of diseases and disorders associated with the adenosine receptor, such as cancer. Also provided herein are pharmaceutical compositions, methods of inhibiting the activity of an adenosine receptor, and methods of treating disease and disorders using these compounds.

18 Claims, No Drawings

SUBSTITUTED TETRAZOLO[1,5-A]PYRAZINES AND TETRAZOLO[1,5-C]PYRIMIDINES AS ADENOSINE RECEPTOR ANTAGONISTS

CROSS-REFERENCE TO RELATED APPLICATIONS

This application claims the benefit of priority to U.S. Provisional Application No. 63/281,445, filed on Nov. 19, 2021, the contents of which are hereby incorporated by reference.

TECHNICAL FIELD

Provided herein are compounds of useful for the treatment of diseases and disorders associated with the adenosine receptor, such as cancer. Also provided herein are pharmaceutical compositions, methods of inhibiting the activity of an adenosine receptor, and methods of treating disease and disorders using these compounds.

BACKGROUND

Adenosine is an endogenous factor with cell-protective activity, especially under damaging conditions with limited oxygen and substrate supply. Adenosine arises as an intermediate during the intracellular breakdown of adenosine 5′-monophosphate (AMP), but can be released from the cell and function as a hormone-like substance or neurotransmitter by binding specific receptors. There are four subtypes of adenosine receptors, A1, A2a, A2b and A3, all belonging to the G protein coupled receptor family, mainly coupled with Gs and -Gi proteins. See Jamwal et al., Curr. Pharm. Des., 2019, 25(26):2892-2905. The activity of adenosine receptors is mediated by cyclic AMP (cAMP). Activation of A2a or A2b receptors in turn activates the membrane-bound adenylate cyclase, leading to an increase in the intracellular concentration of cAMP, while activation of the A1 or A3 receptors results in a decrease in the intracellular concentration of cAMP.

Given their role in modulating cAMP levels, adenosine receptors play a role a various physiological processes such as heart rate, blood pressure, bone homeostatis, immune response, and cell growth and division. See Fishman et al., Handb. Exp. Pharmacol. (2009) 193:399-441. Despite significant research into adenosine receptor modulation, particularly in development of adenosine receptor antagonists, very few are approved for human use. See Franco et al., Cells, 2021, 10, 2831. As such, there is a need for adenosine receptor antagonists.

SUMMARY

Some embodiments provide a compound of Formula (I):

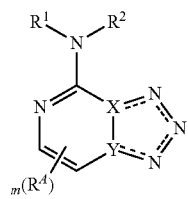

(I)

or a pharmaceutically acceptable salt thereof, wherein:
$R^1$ and $R^2$ are independently hydrogen, C1-C4 alkyl, C1-C4 haloalkyl, 4-7 membered heterocyclyl, C3-C6 cycloalkyl, C2-C4 alkenyl, or C2-C4 alkynyl;
or $R^1$ and $R^2$ together with the nitrogen atom to which they are attached to form a 4-7 membered heterocyclyl optionally substituted with 1-2 substituents independently selected from halogen and C1-C4 alkyl; or
one of $R^1$ and $R^2$ is hydrogen; and the other of $R^1$ and $R^2$, together with the nitrogen atom to which it is attached, forms an (acyloxy)C1-C6 alkyl carbamate or an (oxodioxolenyl)methyl carbamate;
each ≡ represents a double or single bond;
one of X and Y is carbon and the other of X and Y is nitrogen;
each $R^A$ is independently C5-C7 cycloalkyl optionally substituted with 1-3 independently selected $R^3$, 4-7 membered heterocyclyl optionally substituted with 1-3 independently selected $R^3$, phenyl optionally substituted with 1-3 independently selected $R^3$, or 5-10 membered heteroaryl optionally substituted with 1-3 independently selected $R^3$;
m is one or two;
each $R^3$ is independently halogen, cyano, —$OR^4$, —$NR^4R^5$, —C(=O)$R^{4A}$, —$CO_2R^{4B}$, —C(=O)$NR^4R^5$, —$SR^4$, —S(=O)$R^{4A}$, —$SO_2R^{4A}$, —$NO_2$, —OC(=O)$R^{4A}$, —OC(=O)$NR^4R^5$, —S(=O)$NR^4R^5$, —$SO_2NR^4R^5$, —$NR^4C$(=O)$NR^4R^5$, —$NR^4C$(=O)$R^{4A}$, —$NR^4CO_2R^{4A}$, —$NR^4S$(=O)$R^{4A}$—$NR^4SO_2R^{4A}$, C1-C6 haloalkyl, C2-C6 alkenyl, C2-C6-alkynyl, C3-C6 cycloalkyl, or C1-C6 alkyl optionally substituted with hydroxyl;
$R^4$ and $R^5$ are independently hydrogen, C1-C6 alkyl, C1-C6 haloalkyl, C3-C6 cycloalkyl, C2-C6 alkenyl, C2-C6-alkynyl, or —C(=O)$R^6$;
$R^{4A}$ is C1-C6 alkyl, C1-C6 haloalkyl, C2-C6 alkenyl, C2-C6-alkynyl, or C3-C6 cycloalkyl;
$R^{4B}$ is hydrogen, C1-C6 alkyl, C1-C6 haloalkyl, C2-C6 alkenyl, C2-C6-alkynyl, or C3-C6 cycloalkyl; and
$R^6$ is C1-C6 alkyl, C1-C6 haloalkyl, C2-C6 alkenyl, C2-C6-alkynyl, or C3-C6 cycloalkyl.

Some embodiments provide a pharmaceutical composition comprising the compound of Formula (I), or a pharmaceutically acceptable salt thereof, and a pharmaceutically acceptable excipient.

Some embodiments provide a compound for use in inhibiting the activity of one or more adenosine receptors selected from the group consisting of A2a, A2b, and A1, wherein the compound is a compound of Formula (I), or a pharmaceutically acceptable salt thereof.

Some embodiments provide a method of inhibiting the activity of one or more adenosine receptors selected from the group consisting of A2a, A2b, and A1, comprising contacting one or more of the receptors with a compound of Formula (I) in an amount sufficient to inhibit the activity of the receptor.

Some embodiments provide a method of treating cancer in a subject in need thereof, comprising administering to the subject a therapeutically effective amount of the compound of Formula (I), or a pharmaceutically acceptable salt thereof.

Some embodiments provide a method of treating an immune disease or disorder in a subject in need thereof, comprising administering to the subject a therapeutically effective amount of the compound of Formula (I), or a pharmaceutically acceptable salt thereof.

DETAILED DESCRIPTION

The present disclosure provides compounds of Formula (I) or pharmaceutically acceptable salts thereof, methods of blocking adenosine receptors, methods of treating diseases such as cancer, and pharmaceutical compositions thereof.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is also to be understood that the terminology used herein is to describe particular aspects only and is not intended to be limiting. As used in the specification and the claims, the term "comprising" can include the aspect of "consisting of." Unless defined otherwise, all technical and scientific terms used herein have the same meaning as commonly understood by one of ordinary skill in the art to which the disclosed compositions and methods belong.

Compounds

The compounds disclosed herein have a structure of Formula (I):

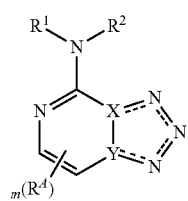

(I)

or a pharmaceutically acceptable salt thereof, wherein:
$R^1$ and $R^2$ are independently hydrogen, C1-C4 alkyl, C1-C4 haloalkyl, 4-7 membered heterocyclyl, C3-C6 cycloalkyl, C2-C4 alkenyl, or C2-C4-alkynyl;
or $R^1$ and $R^2$ together with the nitrogen atom to which they are attached to form a 4-7 membered heterocyclyl optionally substituted with 1-2 substituents independently selected from halogen and C1-C4 alkyl; or
one of $R^1$ and $R^2$ is hydrogen; and the other of $R^1$ and $R^2$, together with the nitrogen atom to which it is attached, forms an (acyloxy)C1-C6 alkyl carbamate or an (oxodioxolenyl)methyl carbamate;
each ═══ represents a double or single bond;
one of X and Y is carbon and the other of X and Y is nitrogen;
each $R^A$ is independently C5-C7 cycloalkyl optionally substituted with 1-3 independently selected $R^3$, 4-7 membered heterocyclyl optionally substituted with 1-3 independently selected $R^3$, phenyl optionally substituted with 1-3 independently selected $R^3$, or 5-10 membered heteroaryl optionally substituted with 1-3 independently selected $R^3$;
m is one or two;
each $R^3$ is independently halogen, cyano, —$OR^4$, —$NR^4R^5$, —C(═O)$R^{4A}$, —$CO_2R^{4B}$, —C(═O)NR^4R^5$, —$SR^4$, —S(═O)$R^{4A}$, —$SO_2R^{4A}$, —$NO_2$, —OC(═O)$R^{4A}$, —OC(═O)NR^4R^5$, —S(═O)NR^4R^5$, —$SO_2NR^4R^5$, —NR^4C(═O)NR^4R^5$, —NR^4C(═O)$R^{4A}$, —NR^4CO_2R^{4A}$, —NR^4S(═O)$R^{4A}$, —NR^4SO_2R^{4A}$, C1-C6 haloalkyl, C2-C6 alkenyl, C2-C6-alkynyl, C3-C6 cycloalkyl, or C1-C6 alkyl optionally substituted with hydroxyl;
$R^4$ and $R^5$ are independently hydrogen, C1-C6 alkyl, C1-C6 haloalkyl, C3-C6 cycloalkyl, C2-C6 alkenyl, C2-C6-alkynyl, or —C(═O)$R^6$;
$R^{4A}$ is C1-C6 alkyl, C1-C6 haloalkyl, C2-C6 alkenyl, C2-C6-alkynyl, or C3-C6 cycloalkyl;
$R^{4B}$ is hydrogen, C1-C6 alkyl, C1-C6 haloalkyl, C2-C6 alkenyl, C2-C6-alkynyl, or C3-C6 cycloalkyl; and
$R^6$ is C1-C6 alkyl, C1-C6 haloalkyl, C2-C6 alkenyl, C2-C6-alkynyl, or C3-C6 cycloalkyl.

In some embodiments, $R^2$ is hydrogen, C1-C4 alkyl, C1-C4 haloalkyl, 4-7 membered heterocyclyl, C3-C6 cycloalkyl, C2-C4 alkenyl, or C2-C4-alkynyl. In some embodiments, $R^1$ is hydrogen, C1-C4 alkyl, 4-7 membered heterocyclyl, or C3-C6 cycloalkyl. In some embodiments, $R^1$ is hydrogen, C1-C4 alkyl, C1-C4 haloalkyl, C2-C4 alkenyl, or C2-C4-alkynyl. In some embodiments, $R^1$ is hydrogen or C1-C4 alkyl. In some embodiments, $R^1$ is hydrogen. In some embodiments, $R^1$ is C1-C4 alkyl. In some embodiments, $R^1$ is methyl, ethyl, isopropyl, n-butyl, or tert-butyl. In embodiments, $R^1$ is methyl. In some embodiments, $R^1$ is ethyl. In some embodiments, $R^1$ is isopropyl. In some embodiments, $R^1$ is tert-butyl. In some embodiments, $R^1$ is C2-C4 alkenyl. In some embodiments, $R^1$ is C2-C4-alkynyl. In some embodiments, $R^1$ is C3-C6 cycloalkyl. In some embodiments, $R^1$ is 4-7 membered heterocyclyl. In some embodiments, $R^1$ is C1-C4 haloalkyl. In some embodiments, $R^1$ is $CF_3$.

In some embodiments, $R^1$ is hydrogen, C1-C4 alkyl, C1-C4 haloalkyl, 4-7 membered heterocyclyl, C3-C6 cycloalkyl, C2-C4 alkenyl, or C2-C4-alkynyl. In some embodiments, $R^2$ is hydrogen, C1-C4 alkyl, 4-7 membered heterocyclyl, or C3-C6 cycloalkyl. In some embodiments, $R^2$ is hydrogen, C1-C4 alkyl, C1-C4 haloalkyl, C2-C4 alkenyl, or C2-C4-alkynyl. In some embodiments, $R^2$ is hydrogen or C1-C4 alkyl. In some embodiments, $R^2$ is hydrogen. In some embodiments, $R^2$ is C1-C4 alkyl. In some embodiments, $R^2$ is methyl, ethyl, isopropyl, n-butyl, or tert-butyl. In embodiments, $R^2$ is methyl. In some embodiments, $R^2$ is ethyl. In some embodiments, $R^2$ is isopropyl. In some embodiments, $R^2$ is tert-butyl. In some embodiments, $R^2$ is C3-C6 cycloalkyl. In some embodiments, $R^2$ is 4-7 membered heterocyclyl. In some embodiments, $R^2$ is C1-C4 haloalkyl. In some embodiments, $R^2$ is $CF_3$. In some embodiments, $R^2$ is C2-C4 alkenyl. In some embodiments, $R^2$ is C2-C4-alkynyl.

In some embodiments, $R^1$ and $R^2$ are each hydrogen. In some embodiments, $R^1$ and $R^2$ are each independently C1-C4 alkyl. In some embodiments, $R^1$ and $R^2$ are each methyl, ethyl, isopropyl, n-butyl, or tert-butyl. In some embodiments, $R^1$ and $R^2$ are each methyl.

In some embodiments, $R^1$ and $R^2$, together with the nitrogen atom to which they are attached to form a 4-7 membered heterocyclyl optionally substituted with 1-2 substituents independently selected from halogen and C1-C4 alkyl. In some embodiments, $R^1$ and $R^2$, together with the nitrogen atom to which they are attached to form a 5-6 membered heterocyclyl substituted with 1-2 independently selected halogen. In some embodiments, $R^1$ and $R^2$, together with the nitrogen atom to which they are attached to form a 5-6 membered heterocyclyl substituted with 1-2 independently selected C1-C4 alkyl. In some embodiments, $R^1$ and $R^2$, together with the nitrogen atom to which they are attached to form a 5-6 membered heterocyclyl substituted with one halogen and one C1-C4 alkyl. In some embodiments, $R^1$ and $R^2$, together with the nitrogen atom to which they are attached to form an unsubstituted 5-6 membered heterocyclyl.

In some embodiments, one of $R^1$ and $R^2$ is hydrogen; and the other of $R^1$ and $R^2$, together with the nitrogen atom to which it is attached, forms an (acyloxy)C1-C6 alkyl carbamate. In some embodiments, one of $R^1$ and $R^2$ is hydrogen; and the other of $R^1$ and $R^2$, together with the nitrogen atom to which it is attached, forms an (oxodioxolenyl) methyl carbamate.

In some embodiments, one of X and Y is carbon and the other of X and Y is nitrogen. In some embodiments, X is carbon and Y is nitrogen. In some embodiments, X is nitrogen and Y is carbon.

In some embodiments, each $R^4$ is independently C5-C7 cycloalkyl optionally substituted with 1-3 independently selected $R^3$, 4-7 membered heterocyclyl optionally substituted with 1-3 independently selected $R^3$, phenyl optionally substituted with 1-3 independently selected $R^3$, or 5-10 membered heteroaryl optionally substituted with 1-3 independently selected $R^3$. In some embodiments, one or two $R^4$ is phenyl optionally substituted with 1-3 independently selected $R^3$ or 5-10 membered heteroaryl optionally substituted with 1-3 independently selected $R^3$. In some embodiments, one or two $R^4$ is phenyl optionally substituted with 1-3 independently selected $R^3$. In some embodiments, one or two $R^4$ is phenyl substituted with 1-3 independently selected $R^3$. In some embodiments, one or two $R^4$ is phenyl substituted with 1-2 independently selected $R^3$. In some embodiments, one or two $R^4$ is phenyl substituted with one $R^3$. In some embodiments, one or two $R^4$ is 5-10 membered heteroaryl optionally substituted with 1-3 independently selected $R^3$. In some embodiments, one or two $R^4$ is 5-10 membered heteroaryl substituted with 1-3 independently selected $R^3$. In some embodiments, one or two $R^4$ is 5-10 membered heteroaryl substituted with 1-2 independently selected $R^3$. In some embodiments, one or two $R^4$ is 5-10 membered heteroaryl substituted with one $R^3$. In some embodiments, one or two $R^4$ is C5-C7 cycloalkyl optionally substituted with 1-3 independently selected $R^3$. In some embodiments, one or two $R^4$ is C5-C7 cycloalkyl substituted with 1-3 independently selected $R^3$. In some embodiments, one or two $R^4$ is C5-C7 cycloalkyl substituted with 1-2 independently selected $R^3$. In some embodiments, one or two $R^4$ is C5-C7 cycloalkyl substituted with one $R^3$. In some embodiments, one or two $R^4$ is 4-7 membered heterocyclyl optionally substituted with 1-3 independently selected $R^3$. In some embodiments, one or two $R^4$ is 4-7 membered heterocyclyl substituted with 1-3 independently selected $R^3$. In some embodiments, one or two $R^4$ is 4-7 membered heterocyclyl substituted with 1-2 independently selected $R^3$. In some embodiments, one or two $R^4$ is 4-7 membered heterocyclyl substituted with one $R^3$.

In some embodiments, each $R^4$ is independently selected from:

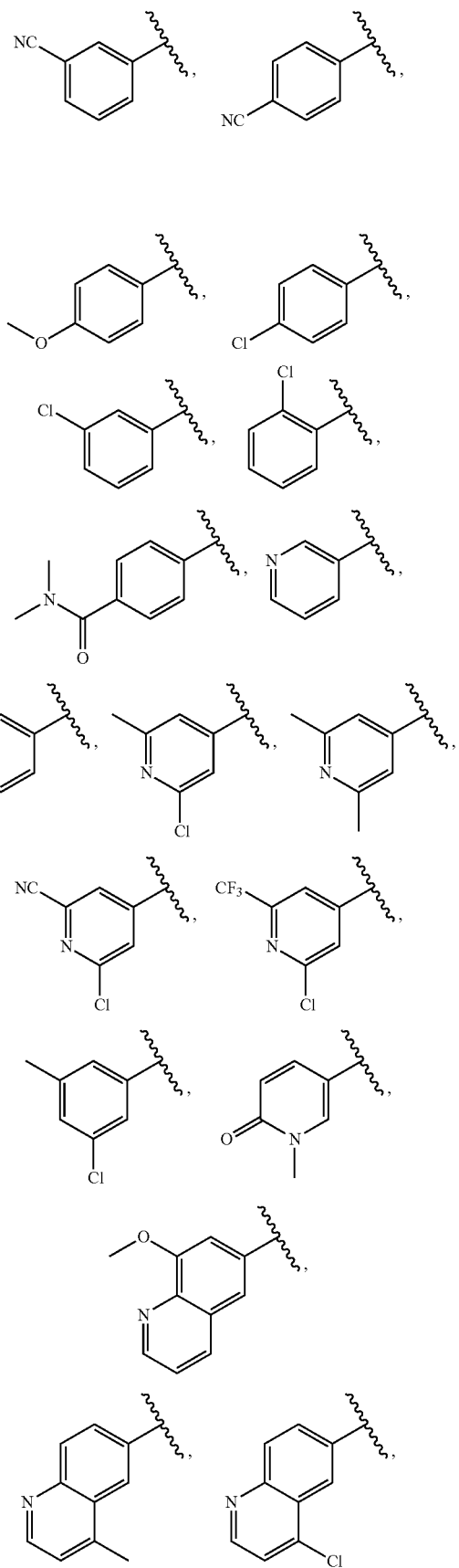

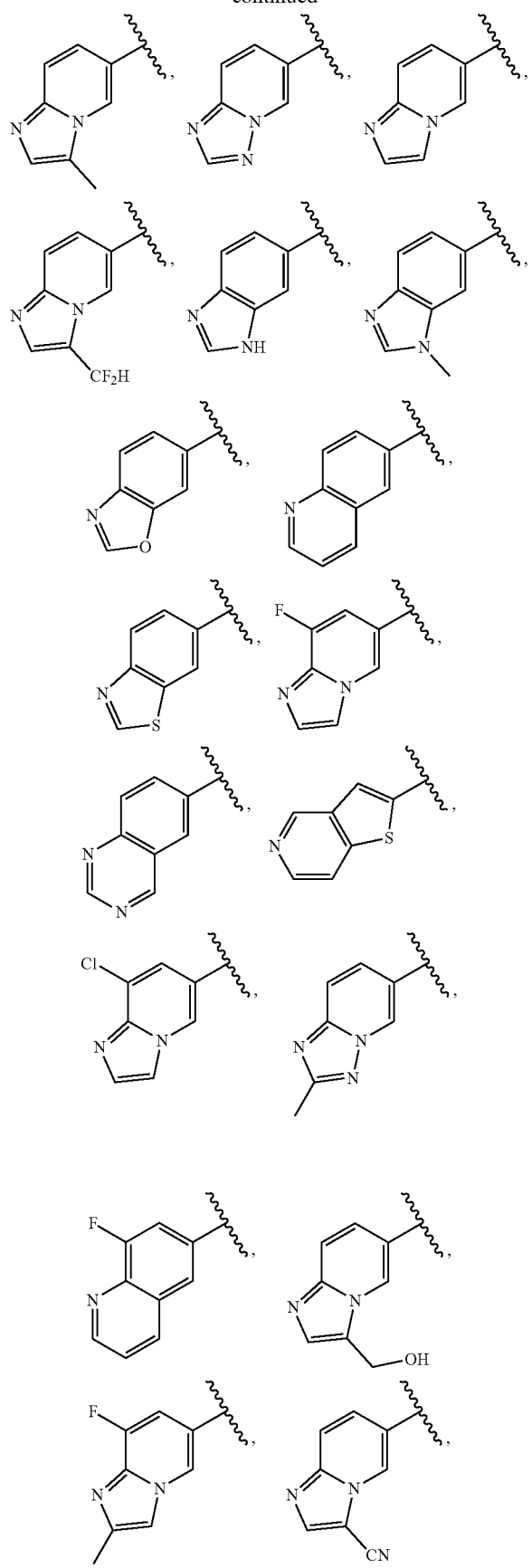
-continued
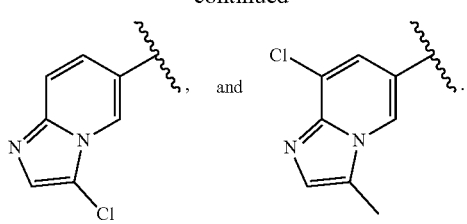
and
In some embodiments, each $R^A$ is independently selected from:
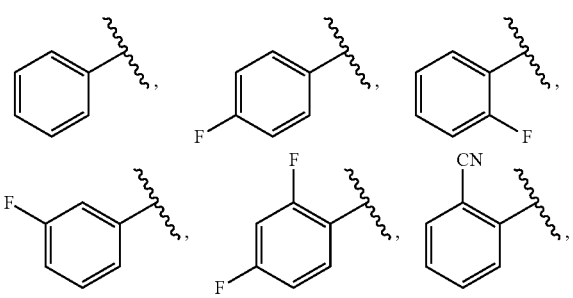
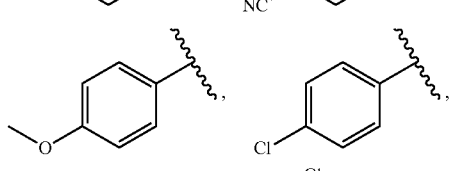
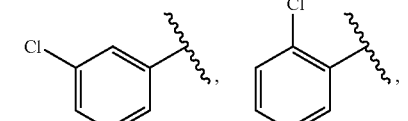
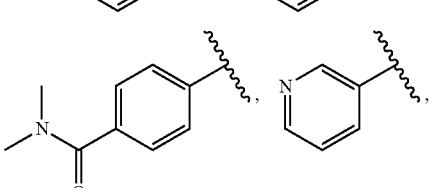
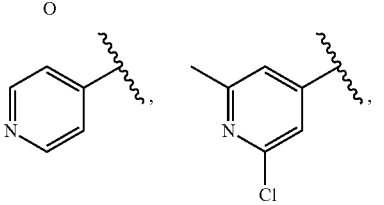
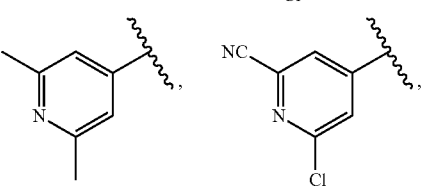

-continued
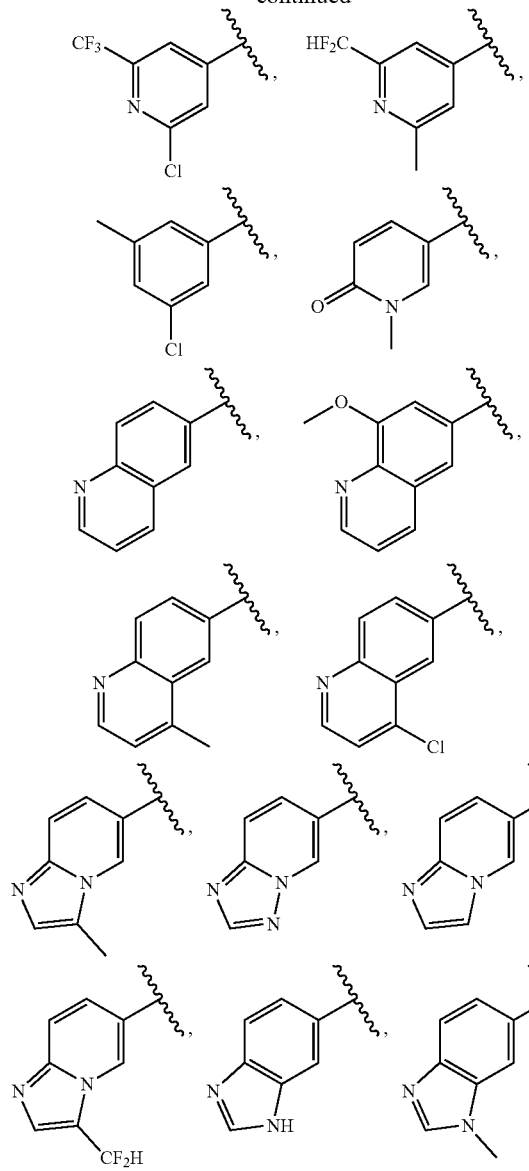
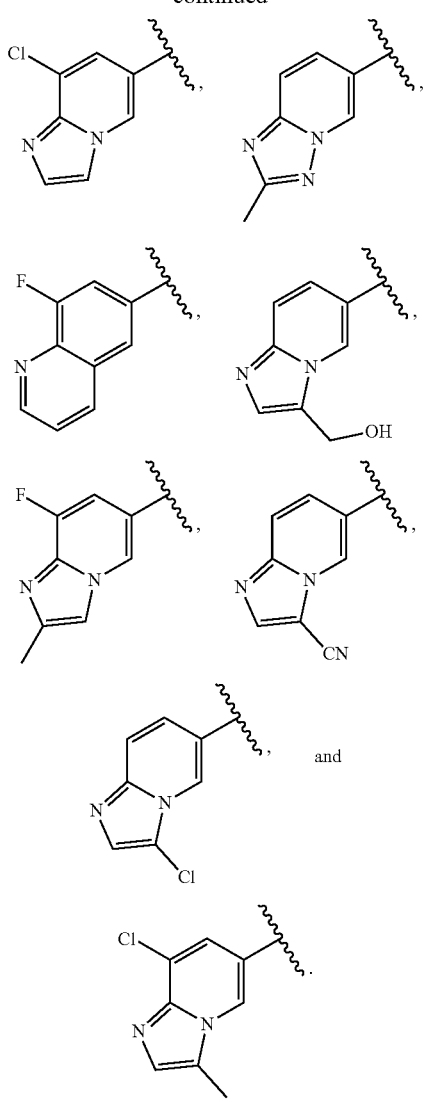
In some embodiments, one $R^A$ is
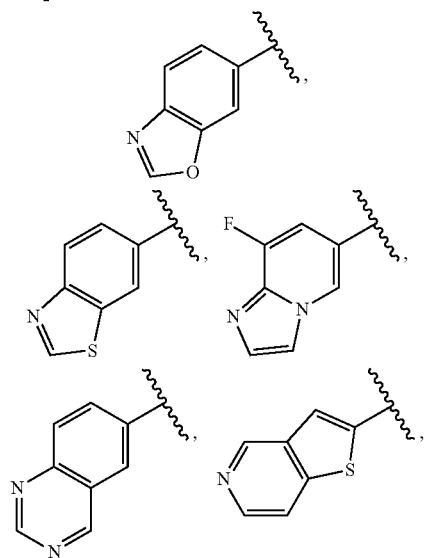
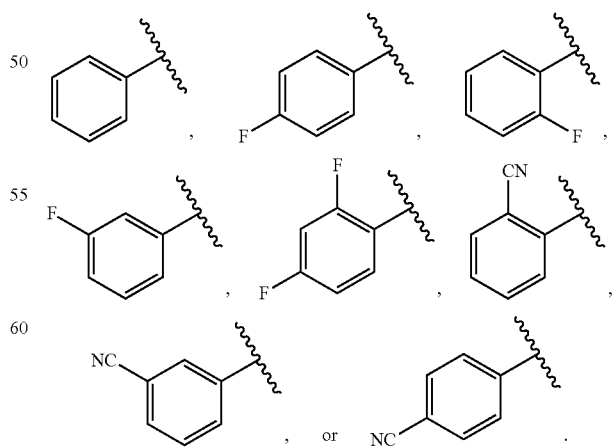

In some embodiments, one $R^A$ is

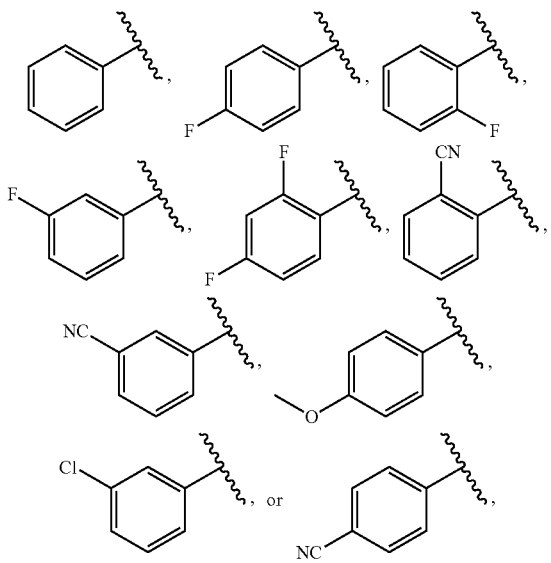

In some embodiments, one $R^A$ is

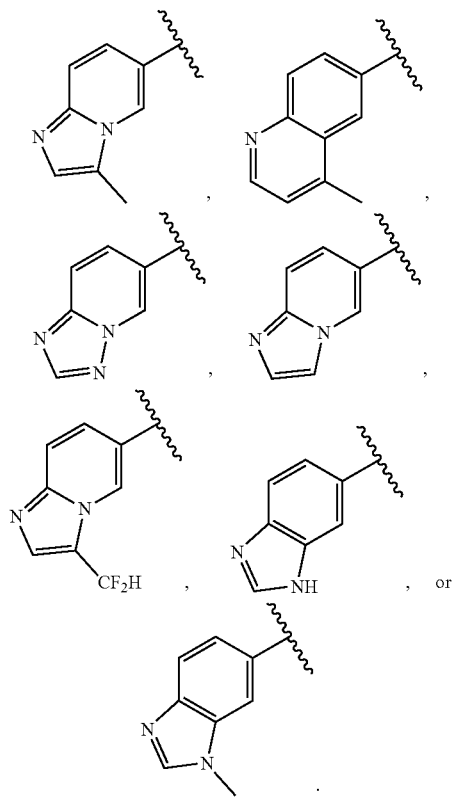

In some embodiments, one or two $R^A$ is an unsubstituted phenyl. In some embodiments, one or two $R^A$ is an unsubstituted 5-10 membered heteroaryl. In some embodiments, one or two $R^A$ is an unsubstituted C5-C7 cycloalkyl.

In some embodiments, m is one or two. In some embodiments, m is one. In some embodiments, m is two. In some embodiments, m is two and each $R^A$ is the same. In some embodiments, m is two and each $R^A$ is different. In some embodiments, m is 2; one $R^A$ is phenyl substituted with one or two independently selected $R^3$, or 6 membered heteroaryl substituted with one or two independently selected $R^3$; and the other $R^A$ is a 6-10 membered heteroaryl substituted with one or two independently selected $R^3$. In some embodiments, m is 2; one $R^A$ is phenyl substituted with one or two independently selected $R^3$, or 6 membered heteroaryl substituted with one or two independently selected $R^3$; the other $R^A$ is a 6-10 membered heteroaryl substituted with one or two independently selected $R^3$; and, each $R^3$ is independently selected from C1-C3 alkyl, C1-C3 haloalkyl, methoxy, fluoro, chloro, and cyano.

In some embodiments, each $R^3$ is independently halogen, cyano, —$OR^4$, —$NR^4R^5$, —$C(=O)R^{4A}$, —$CO_2R^{4B}$, —$C(=O)NR^4R^5$, —$SR^4$, —$S(=O)R^{4A}$, —$SO_2R^{4A}$, —$NO_2$, —$OC(=O)R^{4A}$, —$OC(=O)NR^4R^5$, —$S(=O)NR^4R^5$, —$SO_2NR^4R^5$, —$NR^4C(=O)NR^4R^5$, —$NR^4C(=O)R^{4A}$, —$NR^4CO_2R^{4A}$, —$NR^4S(=O)R^{4A}$, —$NR^4SO_2R^{4A}$, C1-C6 haloalkyl, C2-C6 alkenyl, C2-C6-alkynyl, C3-C6 cycloalkyl, or C1-C6 alkyl optionally substituted with hydroxyl. In some embodiments, each $R^3$ is independently halogen, cyano, —$OR^4$, —$NR^4R^5$, —$C(=O)R^{4A}$, —$CO_2R^{4B}$, or —$C(=O)NR^4R^5$. In some embodiments, each $R^3$ is independently —$SR^4$, —$S(=O)R^{4A}$, —$SO_2R^{4A}$, —$NO_2$, —$OC(=O)R^{4A}$, —$OC(=O)NR^4R^5$, —$S(=O)NR^4R^5$, —$SO_2NR^4R^5$, —$NR^4C(=O)NR^4R^5$, —$NR^4C(=O)R^{4A}$, —$N^4CO_2R^{4A}$, —$NR^4S(=O)R^{4A}$, or —$NR^4SO_2R^{4A}$. In some embodiments, each $R^3$ is independently C1-C6 haloalkyl, C2-C6 alkenyl, C2-C6-alkynyl, C3-C6 cycloalkyl, or C1-C6 alkyl optionally substituted with hydroxyl. In some embodiments, one or two $R^3$ is independently halogen. In some embodiments, one or two $R^3$ is independently cyano. In some embodiments, one or two $R^3$ is independently —$OR^4$. In some embodiments, one or two $R^3$ is independently $NR^4R^5$. In some embodiments, one or two $R^3$ is independently —$C(=O)R^{4A}$. In some embodiments, one or two $R^3$ is independently —$CO_2R^{4B}$. In some embodiments, one or two $R^3$ is independently —$C(=O)NR^4R^5$. In some embodiments, one or two $R^3$ is independently —$SR^4$. In some embodiments, one or two $R^3$ is independently —$S(=O)R^{4A}$. In some embodiments, one or two $R^3$ is independently —$SO_2R^{4A}$. In some embodiments, one or two $R^3$ is independently —$NO_2$. In some embodiments, one or two $R^3$ is independently —$OC(=O)R^{4A}$. In some embodiments, one or two $R^3$ is independently —$OC(=O)NR^4R^5$. In some embodiments, one or two $R^3$ is independently —$S(=O)NR^4R^5$. In some embodiments, one or two $R^3$ is independently —$SO_2NR^4R^5$. In some embodiments, one or two $R^3$ is independently —$NR^4C(=O)NR^4R^5$. In some embodiments, one or two $R^3$ is independently —$NR^4C(=O)R^{4A}$. In some embodiments, one or two $R^3$ is independently —$NR^4CO_2R^{4A}$. In some embodiments, one or two $R^3$ is independently —$NR^4S(=O)R^{4A}$ In some embodiments, one or two $R^3$ is independently —$NR^4SO_2R^{4A}$. In some embodiments, one or two $R^3$ is independently C1-C6 haloalkyl. In some embodiments, one or two $R^3$ is independently difluoromethyl or trifluoromethyl. In some embodiments, one or two $R^3$ is independently C2-C6 alkenyl. In some embodiments, one or two $R^3$ is independently C2-C6-alkynyl. In some embodiments, one or two $R^3$ is independently C3-C6 cycloalkyl. In some embodiments, one or two $R^3$ is independently C1-C6 alkyl optionally substituted with hydroxyl. In some embodiments, one or two $R^3$ is independently C1-C6 alkyl substituted with hydroxyl. In some embodiments, one or two $R^3$ is independently hydroxymethyl. In some embodiments, one or two $R^3$ is independently an unsubstituted C1-C6 alkyl. In some embodiments, one or two $R^3$ is independently methyl, ethyl, isopropyl, n-butyl, or tert-butyl. In some embodiments, one or two $R^3$ is methyl. In some embodiments, each $R^3$ is independently halogen, C1-C6 alkyl, cyano, or —$OR^4$. In some embodiments, each $R^3$ is independently halogen, C1-C6 alkyl, or —$OR^4$. In some embodiments, each $R^3$ is independently selected from C1-C3 alkyl, C1-C3 haloalkyl, methoxy, fluoro, chloro, and cyano.

In some embodiments, each $R^4$ is independently hydrogen, C1-C6 alkyl, C1-C6 haloalkyl, C3-C6 cycloalkyl, C2-C6 alkenyl, C2-C6-alkynyl, or —C(=O)$R^6$. In some embodiments, each $R^4$ is independently hydrogen, C2-C6 alkenyl, C2-C6-alkynyl, or C1-C6 alkyl. In some embodiments, each $R^4$ is independently hydrogen or C3-C6 cycloalkyl. In some embodiments, each $R^4$ is independently hydrogen or C1-C6 haloalkyl. In some embodiments, each $R^4$ is independently hydrogen or —C(=O)$R^6$. In some embodiments, each $R^4$ is independently C1-C6 alkyl. In some embodiments, each $R^4$ is independently methyl, ethyl, isopropyl, n-butyl, or tert-butyl. In some embodiments, each $R^4$ is methyl. In some embodiments, each $R^4$ is hydrogen.

In some embodiments, each $R^5$ is independently hydrogen, C1-C6 alkyl, C1-C6 haloalkyl, C3-C6 cycloalkyl, C2-C6 alkenyl, C2-C6-alkynyl, or —C(=O)$R^6$. In some embodiments, each $R^5$ is independently hydrogen, C2-C6 alkenyl, C2-C6-alkynyl, or C1-C6 alkyl. In some embodiments, each $R^5$ is independently hydrogen or C3-C6 cycloalkyl. In some embodiments, each $R^5$ is independently hydrogen or C1-C6 haloalkyl. In some embodiments, each $R^5$ is independently hydrogen or —C(=O)$R^6$. In some embodiments, each $R^5$ is independently C1-C6 alkyl. In some embodiments, each $R^5$ is independently methyl, ethyl, isopropyl, n-butyl, or tert-butyl. In some embodiments, each $R^5$ is methyl. In some embodiments, each $R^5$ is hydrogen.

In some embodiments, $R^4$ and $R^5$ are the same. In some embodiments, $R^4$ and $R^5$ are different.

In some embodiments, $R^{4A}$ is C1-C6 alkyl, C1-C6 haloalkyl, C2-C6 alkenyl, C2-C6-alkynyl, or C3-C6 cycloalkyl. In some embodiments, $R^{4A}$ is C1-C6 alkyl, C2-C6 alkenyl, or C2-C6-alkynyl. In some embodiments, $R^{4A}$ is C1-C6 alkyl. In some embodiments, $R^{4A}$ is methyl, ethyl, isopropyl, n-butyl, or tert-butyl. In some embodiments, $R^{4A}$ is methyl. In some embodiments, $R^{4A}$ is C1-C6 haloalkyl. In some embodiments, $R^{4A}$ is $CF_3$. In some embodiments, $R^{4A}$ is C3-C6 cycloalkyl.

In some embodiments, $R^{4B}$ is hydrogen, C1-C6 alkyl, C1-C6 haloalkyl, C2-C6 alkenyl, C2-C6-alkynyl, or C3-C6 cycloalkyl. In some embodiments, $R^{4B}$ is hydrogen. In some embodiments, $R^{4B}$ is C1-C6 alkyl, C2-C6 alkenyl, or C2-C6-alkynyl. In some embodiments, $R^{4B}$ is C1-C6 alkyl. In some embodiments, $R^{4B}$ is methyl, ethyl, isopropyl, n-butyl, or tert-butyl. In some embodiments, $R^{4B}$ is methyl. In some embodiments, $R^{4B}$ is C1-C6 haloalkyl. In some embodiments, $R^{4B}$ is $CF_3$. In some embodiments, $R^{4B}$ is C3-C6 cycloalkyl.

In some embodiments, $R^6$ is C1-C6 alkyl, C1-C6 haloalkyl, C2-C6 alkenyl, C2-C6-alkynyl, or C3-C6 cycloalkyl. In some embodiments, $R^6$ is C1-C6 alkyl, C2-C6 alkenyl, or C2-C6-alkynyl. In some embodiments, $R^6$ is C1-C6 alkyl. In some embodiments, $R^6$ is methyl, ethyl, isopropyl, n-butyl, or tert-butyl. In some embodiments, $R^6$ is methyl. In some embodiments, $R^6$ is C1-C6 haloalkyl. In some embodiments, $R^6$ is $CF_3$. In some embodiments, $R^6$ is C3-C6 cycloalkyl.

In some embodiments, m is 2; one $R^4$ is $R^{A1}$ and the other $R^4$ is $R^{A2}$, wherein $R^{A1}$ and $R^{A2}$ are each independently selected from $R^4$, as described herein.

In some embodiments, the compound of Formula (I), or a pharmaceutically acceptable salt thereof is a compound of Formula (I-A), or a pharmaceutically acceptable salt thereof:

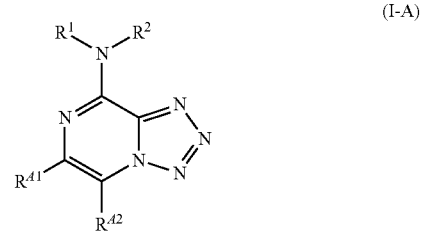

(I-A)

In some embodiments, the compound of Formula (I), or a pharmaceutically acceptable salt thereof is a compound of Formula (I-B), or a pharmaceutically acceptable salt thereof:

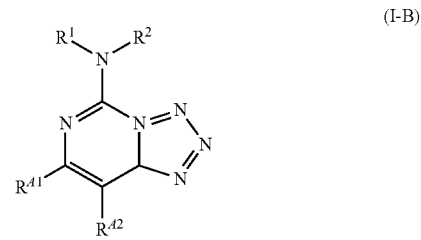

(I-B)

In some embodiments, the compound is selected from a compound in Table 1, or a pharmaceutically acceptable salt thereof.

TABLE 1

| $R^{A1}$ | $R^{A2}$ | X | Y |
|---|---|---|---|
| 4-fluorophenyl | 2-methyl-6-chloropyridin-4-yl | C | N |
| 2-methyl-6-chloropyridin-4-yl | 4-fluorophenyl | C | N |
| 4-fluorophenyl | 3-methyl-5-chlorophenyl | C | N |

TABLE 1-continued
| R^{A1} | R^{A2} | X | Y |
|---|---|---|---|
| 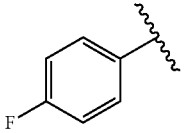 | 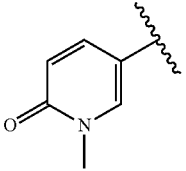 [SMILES: *c1ccc(=O)n(C)c1] | C | N |
| 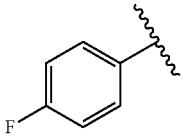 | 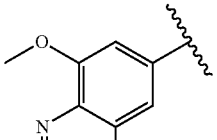 | C | N |
| 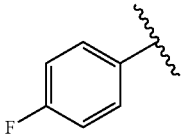 | 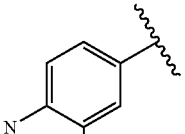 [SMILES: *c1ccc(F)cc1] | C | N |
| 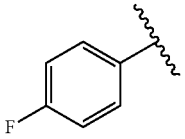 | 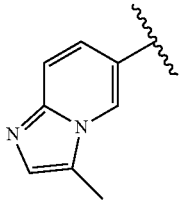 [SMILES: *c1ccc2ncc(C)n2c1] | C | N |
| 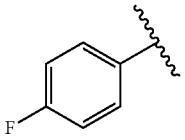 | 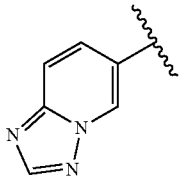 [SMILES: *c1ccc2ncnn2c1] | C | N |
| 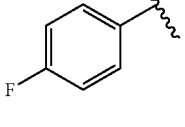 | 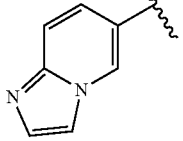 | C | N |
| 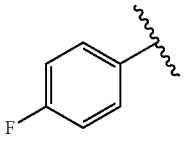 | 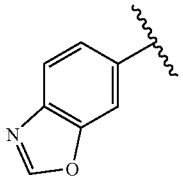 [SMILES: *c1ccc2ncoc2c1] | C | N |
| 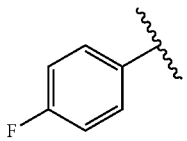 | 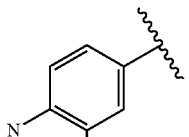 | C | N |
| 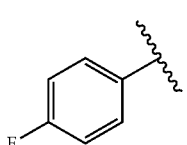 | 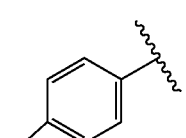 | C | N |
| 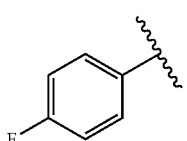 | 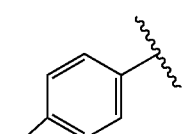 | C | N |
| 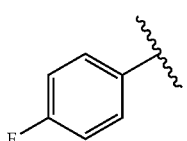 | 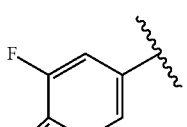 | C | N |
| 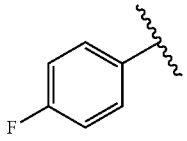 | 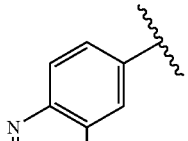 | C | N |
| 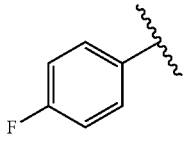 | 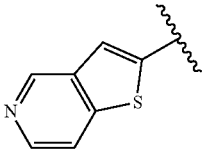 [SMILES: *c1cc2cnccc2s1] | C | N |
| 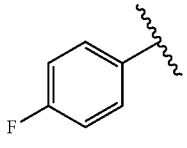 | 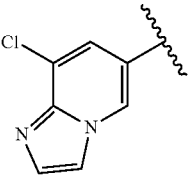 [SMILES: *c1cc(Cl)c2nccn2c1] | C | N |

TABLE 1-continued

| $R^{A1}$ | $R^{A2}$ | X | Y |
|---|---|---|---|
| 4-F-phenyl | [1,2,4]triazolo[1,5-a]pyridin-2-methyl-6-yl | C | N |
| 4-F-phenyl | 8-F-quinolin-6-yl | C | N |
| 4-F-phenyl | 3-(hydroxymethyl)imidazo[1,2-a]pyridin-6-yl | C | N |
| 4-F-phenyl | 8-F-2-methyl-imidazo[1,2-a]pyridin-6-yl | C | N |
| 4-F-phenyl | 3-cyano-imidazo[1,2-a]pyridin-6-yl | C | N |
| 4-F-phenyl | 3-chloro-imidazo[1,2-a]pyridin-6-yl | C | N |
| 4-F-phenyl | 8-chloro-3-methyl-imidazo[1,2-a]pyridin-6-yl | C | N |
| 4-F-phenyl | 3-methyl-imidazo[1,2-a]pyridin-6-yl | N | C |
| 2-F-phenyl | 2-methyl-6-chloro-pyridin-4-yl | C | N |
| 3-F-phenyl | 2-methyl-6-chloro-pyridin-4-yl | C | N |
| 4-F-phenyl | 2,6-dimethyl-pyridin-4-yl | N | C |
| 4-F-phenyl | 1-methyl-2-oxo-pyridin-5-yl | N | C |
| 4-F-phenyl | 1-methyl-benzimidazol-6-yl | N | C |
| 3-cyanophenyl | 4-methyl-quinolin-6-yl | C | N |

TABLE 1-continued
| $R^{41}$ | $R^{42}$ | X | Y |
|---|---|---|---|
| 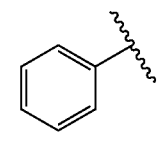 [SMILES: *c1ccccc1] | 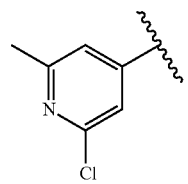 [SMILES: *c1cc(C)nc(Cl)c1] | C | N |
| 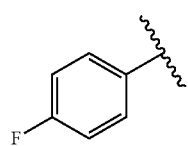 | 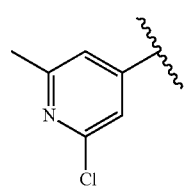 [SMILES: *c1cc(C)nc(Cl)c1] | N | C |
| 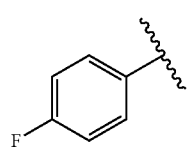 | 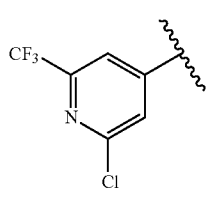 [SMILES: *c1cc(Cl)nc(C(F)(F)F)c1] | C | N |
| 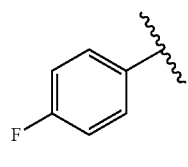 | 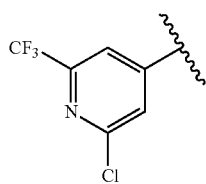 [SMILES: *c1cc(Cl)nc(C(F)(F)F)c1] | N | C |
| 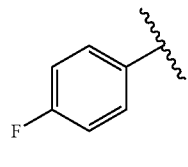 | 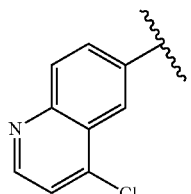 | N | C |
| 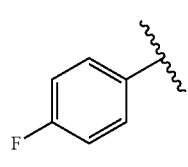 | 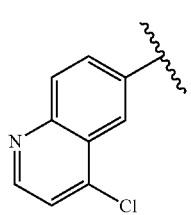 [SMILES: *c1ccc2nccc(Cl)c2c1] | C | N |
| 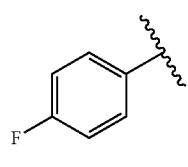 | 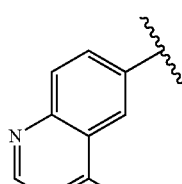 | N | C |
TABLE 1-continued
| $R^{41}$ | $R^{42}$ | X | Y |
|---|---|---|---|
| 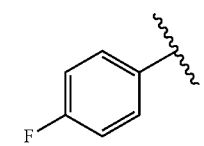 | 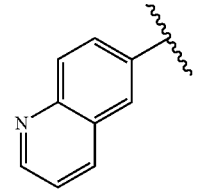 | N | C |
| 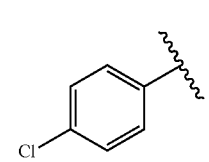 [SMILES: *c1ccc(Cl)cc1] | 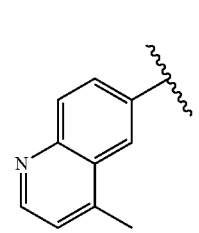 [SMILES: *c1ccc2nccc(C)c2c1] | C | N |
| 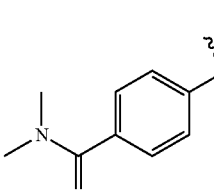 | 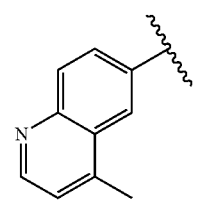 [SMILES: *c1ccc2nccc(C)c2c1] | C | N |
| 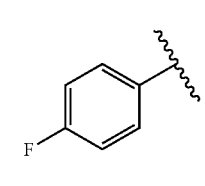 [SMILES: *c1ccc(F)cc1] | 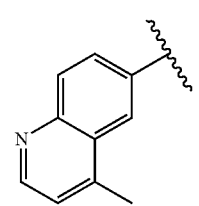 | C | N |
| 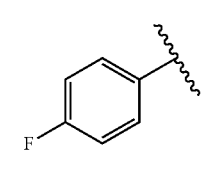 [SMILES: *c1ccc(F)cc1] | 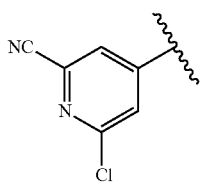 [SMILES: *c1cc(Cl)nc(C#N)c1] | N | C |
| 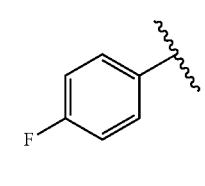 | 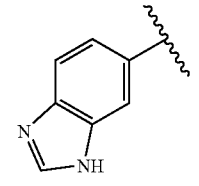 | N | C |
| 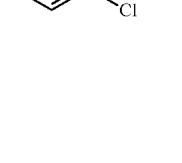 | 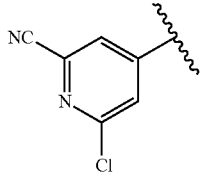 | C | N |

TABLE 1-continued
| R^{A1} | R^{A2} | X | Y |
|---|---|---|---|
| 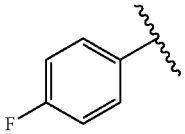 | 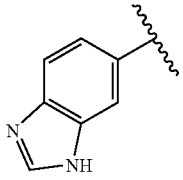 [SMILES: *c1ccc2nc[nH]c2c1] | C | N |
| 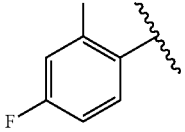 | 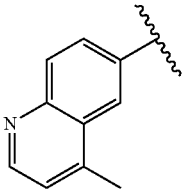 | C | N |
| 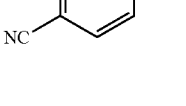 | 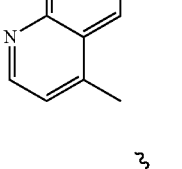 | C | N |
| 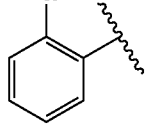 | 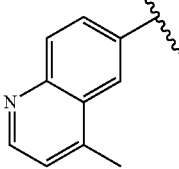 | C | N |
| 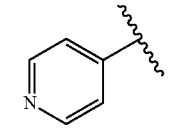 [SMILES: *c1ccncc1] | 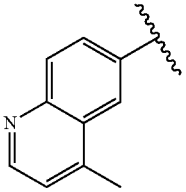 | C | N |
| 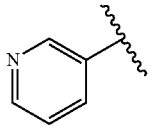 | 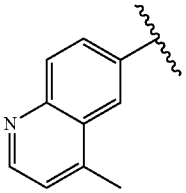 | C | N |
| 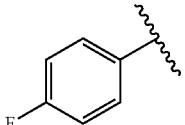 | 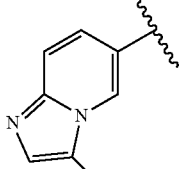 | C | N |
TABLE 1-continued
| R^{A1} | R^{A2} | X | Y |
|---|---|---|---|
|  | 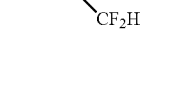 | C | N |
| 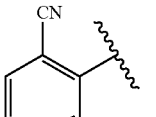 | 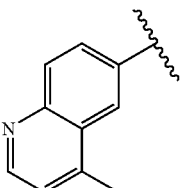 | N | C |
| 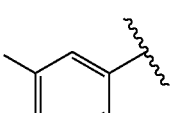 | 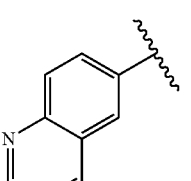 | N | C |
| 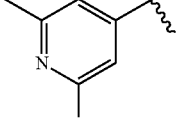 | 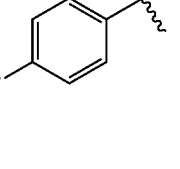 | N | C |
| 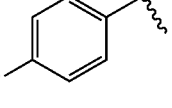 | 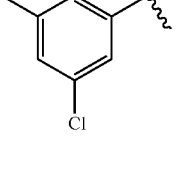 | N | C |
| 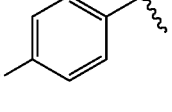 | 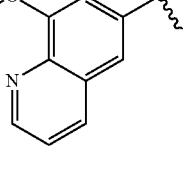 | N | C |
| 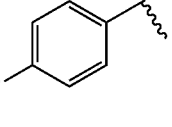 | 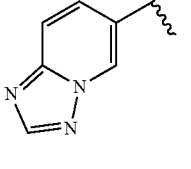 | N | C |

TABLE 1-continued
| R^{A1} | R^{A2} | X | Y |
|---|---|---|---|
| 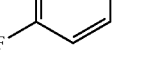 | 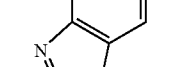 | N | C |
|  |  | N | C |
| 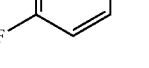 | 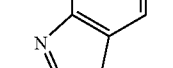 | N | C |
|  |  | N | C |
| 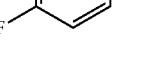 | 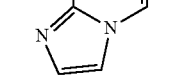 | N | C |
|  | 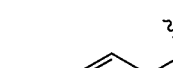 | N | C |
| 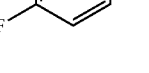 | 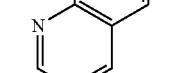 | N | C |
|  |  | N | C |
| 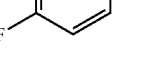 | 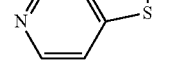 | N | C |
| 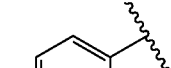 | 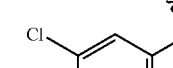 | N | C |
|  |  | N | C |

TABLE 1-continued

| R^{A1} | R^{A2} | X | Y |
|---|---|---|---|
| 3-fluorophenyl | 2-chloro-6-methylpyridin-4-yl | N | C |
| 3-cyanophenyl | 4-methylquinolin-6-yl | N | C |
| phenyl | 2-chloro-6-methylpyridin-4-yl | N | C |
| 4-methoxyphenyl | 4-methylquinolin-6-yl | N | C |
| 4-chlorophenyl | 4-methylquinolin-6-yl | N | C |
| 4-(N,N-dimethylcarbamoyl)phenyl | 4-methylquinolin-6-yl | N | C |
| 2,4-difluorophenyl | 4-methylquinolin-6-yl | N | C |
| 4-cyanophenyl | 4-methylquinolin-6-yl | N | C |
| 2-chlorophenyl | 4-methylquinolin-6-yl | N | C |
| pyridin-4-yl | 4-methylquinolin-6-yl | N | C |
| pyridin-3-yl | 4-methylquinolin-6-yl | N | C |
| 4-fluorophenyl | 3-(difluoromethyl)imidazo[1,2-a]pyridin-6-yl | N | C |
| 2-cyanophenyl | 4-methylquinolin-6-yl | N | C |
| 3-chlorophenyl | 4-methylquinolin-6-yl | C | N |

TABLE 1-continued

| R41 | R42 | X | Y |
|---|---|---|---|
| 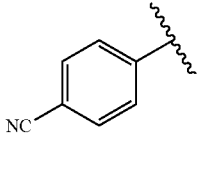 [SMILES: *c1ccc(C#N)cc1] | 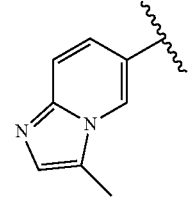 [SMILES: *c1ccc2ncc(C)n2c1] | C | N |
| 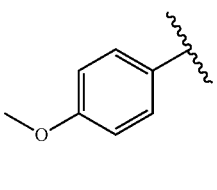 [SMILES: *c1ccc(OC)cc1] | 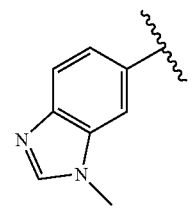 [SMILES: *c1ccc2ncn(C)c2c1] | C | N |
| 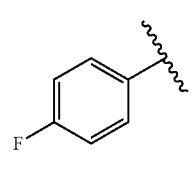 | 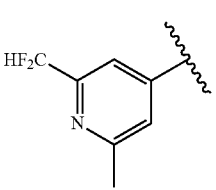 | C | N |
| 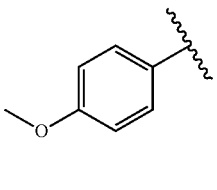 [SMILES: *c1ccc(OC)cc1] | 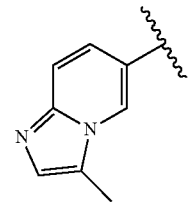 [SMILES: *c1ccc2ncc(C)n2c1] | C | N |
| 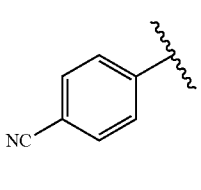 [SMILES: *c1ccc(C#N)cc1] | 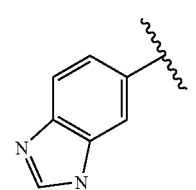 | N | C |
| 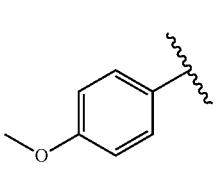 [SMILES: *c1ccc(OC)cc1] | 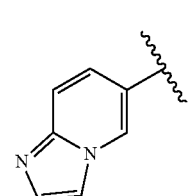 | N | C |
| 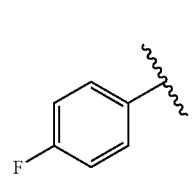 | 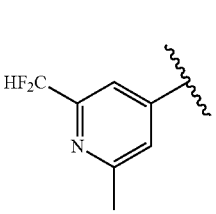 | N | C |

TABLE 1-continued

| R41 | R42 | X | Y |
|---|---|---|---|
| 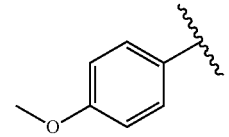 [SMILES: *c1ccc(OC)cc1] | 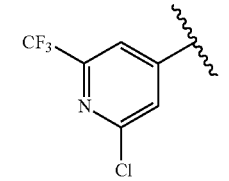 | N | C |

In some embodiments, the compound of Formula (I) is selected from the group of: 5-(2-chloro-6-methylpyridin-4-yl)-6-(4-fluorophenyl)tetrazolo[1,5-a]pyrazin-8-amine, 6-(2-chloro-6-methylpyridin-4-yl)-5-(4-fluorophenyl)tetrazolo[1,5-a]pyrazin-8-amine, 5-(3-chloro-5-methylphenyl)-6-(4-fluorophenyl)tetrazolo[1,5-a]pyrazin-8-amine, 5-(8-amino-6-(4-fluorophenyl)tetrazolo[1,5-a]pyrazin-5-yl)-1-methylpyridin-2(1H)-one, 6-(4-fluorophenyl)-5-(8-methoxyquinolin-6-yl)tetrazolo[1,5-a]pyrazin-8-amine, 6-(4-fluorophenyl)-5-(4-methylquinolin-6-yl)tetrazolo[1,5-a]pyrazin-8-amine, 6-(4-fluorophenyl)-5-(3-methylimidazo[1,2-a]pyridin-6-yl)tetrazolo[1,5-a]pyrazin-8-amine, 5-([1,2,4]triazolo[1,5-a]pyridin-6-yl)-6-(4-fluorophenyl)tetrazolo[1,5-a]pyrazin-8-amine, 6-(4-fluorophenyl)-5-(imidazo[1,2-a]pyridin-6-yl)tetrazolo[1,5-a]pyrazin-8-amine, 5-(benzo[d]oxazol-6-yl)-6-(4-fluorophenyl)tetrazolo[1,5-a]pyrazin-8-amine, 6-(4-fluorophenyl)-5-(quinolin-6-yl)tetrazolo[1,5-a]pyrazin-8-amine, 5-(benzo[d]thiazol-6-yl)-6-(4-fluorophenyl)tetrazolo[1,5-a]pyrazin-8-amine, 6-(4-fluorophenyl)-5-(1-methyl-1H-benzo[d]imidazol-6-yl)tetrazolo[1,5-a]pyrazin-8-amine, 5-(8-fluoroimidazo[1,2-a]pyridin-6-yl)-6-(4-fluorophenyl)tetrazolo[1,5-a]pyrazin-8-amine, 6-(4-fluorophenyl)-5-(quinazolin-6-yl)tetrazolo[1,5-a]pyrazin-8-amine, 6-(4-fluorophenyl)-5-(thieno[3,2-c]pyridin-2-yl)tetrazolo[1,5-a]pyrazin-8-amine, 5-(8-chloroimidazo[1,2-a]pyridin-6-yl)-6-(4-fluorophenyl)tetrazolo[1,5-a]pyrazin-8-amine, 6-(4-fluorophenyl)-5-(2-methyl-[1,2,4]triazolo[1,5-a]pyridin-6-yl)tetrazolo[1,5-a]pyrazin-8-amine, 6-(4-fluorophenyl)-5-(8-fluoroquinolin-6-yl)tetrazolo[1,5-a]pyrazin-8-amine, (6-(8-amino-6-(4-fluorophenyl)tetrazolo[1,5-a]pyrazin-5-yl)imidazo[1,2-a]pyridin-3-yl)methanol, 5-(8-fluoro-2-methylimidazo[1,2-a]pyridin-6-yl)-6-(4-fluorophenyl)tetrazolo[1,5-a]pyrazin-8-amine, 6-(8-amino-6-(4-fluorophenyl)tetrazolo[1,5-a]pyrazin-5-yl)imidazo[1,2-a]pyridine-3-carbonitrile, 5-(3-chloroimidazo[1,2-a]pyridin-6-yl)-6-(4-fluorophenyl)tetrazolo[1,5-a]pyrazin-8-amine, 5-(8-chloro-3-methylimidazo[1,2-a]pyridin-6-yl)-6-(4-fluorophenyl)tetrazolo[1,5-a]pyrazin-8-amine, 7-(4-fluorophenyl)-8-(3-methylimidazo[1,2-a]pyridin-6-yl)tetrazolo[1,5-c]pyrimidin-5-amine, 5-(2-chloro-6-methylpyridin-4-yl)-6-(2-fluorophenyl)tetrazolo[1,5-a]pyrazin-8-amine, 5-(2-chloro-6-methylpyridin-4-yl)-6-(3-fluorophenyl)tetrazolo[1,5-a]pyrazin-8-amine, 8-(2,6-dimethylpyridin-4-yl)-7-(4-fluorophenyl)tetrazolo[1,5-c]pyrimidin-5-amine, 5-(5-amino-7-(4-fluorophenyl)tetrazolo[1,5-c]pyrimidin-8-yl)-1-methylpyridin-2(1H)-one, 7-(4-fluorophenyl)-8-(1-methyl-1H-benzo[d]imidazol-6-yl)tetrazolo[1,5-c]pyrimidin-5-amine, 3-(8-amino-5-(4-methylquinolin-6-yl)tetrazolo[1,5-a]pyrazin-6-yl)benzonitrile, 5-(2-chloro-6-methylpyridin-4-yl)-6-phenyltetrazolo[1,5-a]pyrazin-8-amine, 8-(2-chloro-6-methylpyridin-4-yl)-7-(4-fluorophenyl)tetrazolo[1,5-c]pyrimidin-5-amine, 8-(2-chloro-6-(trifluoromethyl)pyridin-4-yl)-7-(4-fluorophenyl)tetrazolo[1,5-c]pyrimidin-5-amine, 8-(4-chloroquinolin-6-yl)-7-(4-fluorophenyl)tetrazolo[1,5-c]pyrimidin-5-amine, 7-(4-fluorophenyl)-8-(4-methylquinolin-6-yl)tetrazolo[1,5-c]pyrimidin-5-amine, 7-(4-fluorophenyl)-8-(quinolin-6-yl)tetrazolo[1,5-c]pyrimidin-5-amine, 5-(3-(difluoromethyl)imidazo[1,2-a]pyridin-6-yl)-6-(4-fluorophenyl)tetrazolo[1,5-a]pyrazin-8-amine, 5-(2-chloro-6-methylpyridin-4-yl)-6-phenyltetrazolo[1,5-a]pyrazin-8-amine, 6-(2,4-difluorophenyl)-5-(4-methylquinolin-6-yl)tetrazolo[1,5-a]pyrazin-8-amine, 2-(8-amino-5-(4-methylquinolin-6-yl)tetrazolo[1,5-a]pyrazin-6-yl)benzonitrile, 4-(8-amino-5-(4-methylquinolin-6-yl)tetrazolo[1,5-a]pyrazin-6-yl)benzonitrile, 6-(4-methoxyphenyl)-5-(4-methylquinolin-6-yl)tetrazolo[1,5-a]pyrazin-8-amine, 6-(4-chlorophenyl)-5-(4-methylquinolin-6-yl)tetrazolo[1,5-a]pyrazin-8-amine, 6-(3-chlorophenyl)-5-(4-methylquinolin-6-yl)tetrazolo[1,5-a]pyrazin-8-amine, 6-(2-chlorophenyl)-5-(4-methylquinolin-6-yl)tetrazolo[1,5-a]pyrazin-8-amine, 5-(4-methylquinolin-6-yl)-6-(pyridin-3-yl)tetrazolo[1,5-a]pyrazin-8-amine, 5-(4-methylquinolin-6-yl)-6-(pyridin-4-yl)tetrazolo[1,5-a]pyrazin-8-amine, 4-(8-amino-5-(4-methylquinolin-6-yl)tetrazolo[1,5-a]pyrazin-6-yl)-N,N-dimethylbenzamide, 4-(5-amino-7-(4-fluorophenyl)tetrazolo[1,5-c]pyrimidin-8-yl)-6-chloropicolinonitrile, and 8-(1H-benzo[d]imidazol-6-yl)-7-(4-fluorophenyl)tetrazolo[1,5-c]pyrimidin-5-amine, or a pharmaceutically acceptable salt of any of the foregoing.

In some embodiments, the compound of Formula (I) is selected from the group of: 5-(2-chloro-6-methylpyridin-4-yl)-6-(4-fluorophenyl)tetrazolo[1,5-a]pyrazin-8-amine, 6-(2-chloro-6-methylpyridin-4-yl)-5-(4-fluorophenyl)tetrazolo[1,5-a]pyrazin-8-amine, 5-(3-chloro-5-methylphenyl)-6-(4-fluorophenyl)tetrazolo[1,5-a]pyrazin-8-amine, 5-(8-amino-6-(4-fluorophenyl)tetrazolo[1,5-a]pyrazin-5-yl)-1-methylpyridin-2(1H)-one, 6-(4-fluorophenyl)-5-(8-methoxyquinolin-6-yl)tetrazolo[1,5-a]pyrazin-8-amine, 6-(4-fluorophenyl)-5-(4-methylquinolin-6-yl)tetrazolo[1,5-a]pyrazin-8-amine, 6-(4-fluorophenyl)-5-(3-methylimidazo[1,2-a]pyridin-6-yl)tetrazolo[1,5-a]pyrazin-8-amine, 5-([1,2,4]triazolo[1,5-a]pyridin-6-yl)-6-(4-fluorophenyl)tetrazolo[1,5-a]pyrazin-8-amine, 6-(4-fluorophenyl)-5-(imidazo[1,2-a]pyridin-6-yl)tetrazolo[1,5-a]pyrazin-8-amine, 5-(benzo[d]oxazol-6-yl)-6-(4-fluorophenyl)tetrazolo[1,5-a]pyrazin-8-amine, 6-(4-fluorophenyl)-5-(quinolin-6-yl)tetrazolo[1,5-a]pyrazin-8-amine, 5-(benzo[d]thiazol-6-yl)-6-(4-fluorophenyl)tetrazolo[1,5-a]pyrazin-8-amine, 6-(4-fluorophenyl)-5-(1-methyl-1H-benzo[d]imidazol-6-yl)tetrazolo[1,5-a]pyrazin-8-amine, 5-(8-fluoroimidazo[1,2-a]pyridin-6-yl)-6-(4-fluorophenyl)tetrazolo[1,5-a]pyrazin-8-amine, 6-(4-fluorophenyl)-5-(quinazolin-6-yl)tetrazolo[1,5-a]pyrazin-8-amine, 6-(4-fluorophenyl)-5-(thieno[3,2-c]pyridin-2-yl)tetrazolo[1,5-a]pyrazin-8-amine, 5-(8-chloroimidazo[1,2-a]pyridin-6-yl)-6-(4-fluorophenyl)tetrazolo[1,5-a]pyrazin-8-amine, 6-(4-fluorophenyl)-5-(2-methyl-[1,2,4]triazolo[1,5-a]pyridin-6-yl)tetrazolo[1,5-a]pyrazin-8-amine, 6-(4-fluorophenyl)-5-(8-fluoroquinolin-6-yl)tetrazolo[1,5-a]pyrazin-8-amine, (6-(8-amino-6-(4-fluorophenyl)tetrazolo[1,5-a]pyrazin-5-yl)imidazo[1,2-a]pyridin-3-yl)methanol, 5-(8-fluoro-2-methylimidazo[1,2-a]pyridin-6-yl)-6-(4-fluorophenyl)tetrazolo[1,5-a]pyrazin-8-amine, 6-(8-amino-6-(4-fluorophenyl)tetrazolo[1,5-a]pyrazin-5-yl)imidazo[1,2-a]pyridine-3-carbonitrile, 5-(3-chloroimidazo[1,2-a]pyridin-6-yl)-6-(4-fluorophenyl)tetrazolo[1,5-a]pyrazin-8-amine, 5-(8-chloro-3-methylimidazo[1,2-a]pyridin-6-yl)-6-(4-fluorophenyl)tetrazolo[1,5-a]pyrazin-8-amine, 7-(4-fluorophenyl)-8-(3-methylimidazo[1,2-a]pyridin-6-yl)tetrazolo[1,5-c]pyrimidin-5-amine, 5-(2-chloro-6-methylpyridin-4-yl)-6-(2-fluorophenyl)tetrazolo[1,5-a]pyrazin-8-amine, 5-(2-chloro-6-methylpyridin-4-yl)-6-(3-fluorophenyl)tetrazolo[1,5-a]pyrazin-8-amine, 8-(2,6-dimethylpyridin-4-yl)-7-(4-fluorophenyl)tetrazolo[1,5-c]pyrimidin-5-amine, 5-(5-amino-7-(4-fluorophenyl)tetrazolo[1,5-c]pyrimidin-8-yl)-1-methylpyridin-2(1H)-one, 7-(4-fluorophenyl)-8-(1-methyl-1H-benzo[d]imidazol-6-yl)tetrazolo[1,5-c]pyrimidin-5-amine, 3-(8-amino-5-(4-methylquinolin-6-yl)tetrazolo[1,5-a]pyrazin-6-yl)benzonitrile, 5-(2-chloro-6-methylpyridin-4-yl)-6-phenyltetrazolo[1,5-a]pyrazin-8-amine, 8-(2-chloro-6-methylpyridin-4-yl)-7-(4-fluorophenyl)tetrazolo[1,5-c]pyrimidin-5-amine, 8-(2-chloro-6-(trifluoromethyl)pyridin-4-yl)-7-(4-fluorophenyl)tetrazolo[1,5-c]pyrimidin-5-amine, 8-(4-chloroquinolin-6-yl)-7-(4-fluorophenyl)tetrazolo[1,5-c]pyrimidin-5-amine, 7-(4-fluorophenyl)-8-(4-methylquinolin-6-yl)tetrazolo[1,5-c]pyrimidin-5-amine, 7-(4-fluorophenyl)-8-(quinolin-6-yl)tetrazolo[1,5-c]pyrimidin-5-amine, 5-(3-(difluoromethyl)imidazo[1,2-a]pyridin-6-yl)-6-(4-fluorophenyl)tetrazolo[1,5-a]pyrazin-8-amine, 5-(2-chloro-6-methylpyridin-4-yl)-6-phenyltetrazolo[1,5-a]pyrazin-8-amine, 6-(2,4-difluorophenyl)-5-(4-methylquinolin-6-yl)tetrazolo[1,5-a]pyrazin-8-amine, 2-(8-amino-5-(4-methylquinolin-6-yl)tetrazolo[1,5-a]pyrazin-6-yl)benzonitrile, 4-(8-amino-5-(4-methylquinolin-6-yl)tetrazolo[1,5-a]pyrazin-6-yl)benzonitrile, 6-(4-methoxyphenyl)-5-(4-methylquinolin-6-yl)tetrazolo[1,5-a]pyrazin-8-amine, 6-(4-chlorophenyl)-5-(4-methylquinolin-6-yl)tetrazolo[1,5-a]pyrazin-8-amine, 6-(3-chlorophenyl)-5-(4-methylquinolin-6-yl)tetrazolo[1,5-a]pyrazin-8-amine, 6-(2-chlorophenyl)-5-(4-methylquinolin-6-yl)tetrazolo[1,5-a]pyrazin-8-amine, 5-(4-methylquinolin-6-yl)-6-(pyridin-3-yl)tetrazolo[1,5-a]pyrazin-8-amine, 5-(4-methylquinolin-6-yl)-6-(pyridin-4-yl)tetrazolo[1,5-a]pyrazin-8-amine, 4-(8-amino-5-(4-methylquinolin-6-yl)tetrazolo[1,5-a]pyrazin-6-yl)-N,N-dimethylbenzamide, 4-(5-amino-7-(4-fluorophenyl)tetrazolo[1,5-c]pyrimidin-8-yl)-6-chloropicolinonitrile, 8-(1H-benzo[d]imidazol-6-yl)-7-(4-fluorophenyl)tetrazolo[1,5-c]pyrimidin-5-amine, 5-(3-(difluoromethyl)imidazo[1,2-a]pyridin-6-yl)-6-(4-fluorophenyl)tetrazolo[1,5-a]pyrazin-8-amine, 2-(8-amino-5-(4-methylquinolin-6-yl)tetrazolo[1,5-a]pyrazin-6-yl)benzonitrile, 6-(3-chlorophenyl)-5-(4-methylquinolin-6-yl)tetrazolo[1,5-a]pyrazin-8-amine, 4-(8-amino-5-(3-methylimidazo[1,2-a]pyridin-6-yl)tetrazolo[1,5-a]pyrazin-6-yl)benzonitrile, 5-(2-(difluoromethyl)-6-methylpyridin-4-yl)-6-(4-fluorophenyl)tetrazolo[1,5-a]pyrazin-8-amine, 6-(4-methoxyphenyl)-5-(1-methyl-1H-benzo[d]imidazol-6-yl)tetrazolo[1,5-a]pyrazin-8-amine, 5-(2-chloro-6-(trifluoromethyl)pyridin-4-yl)-6-(4-fluorophenyl)tetrazolo[1,5-a]pyrazin-8-amine, 6-(4-methoxyphenyl)-5-(3-methylimidazo[1,2-a]pyridin-6-yl)tetrazolo[1,5-a]pyrazin-8-amine, 4-(5-amino-8-(1-methyl-1H-benzo[d]imidazol-6-yl)tetrazolo[1,5-c]pyrimidin-7-yl)benzonitrile, 7-(4-methoxyphenyl)-8-(3-methylimidazo[1,2-a]pyridin-6-yl)tetrazolo[1,5-c]pyrimidin-5-amine, 8-(2-(difluoromethyl)-6-methylpyridin-4-yl)-7-(4-fluorophenyl)tetrazolo[1,5-c]pyrimidin-5-amine, and 8-(2-chloro-6-(trifluoromethyl)pyridin-4-yl)-7-(4-methoxyphenyl)tetrazolo[1,5-c]pyrimidin-5-amine, or a pharmaceutically acceptable salt of any of the foregoing.

Definitions

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

The term "subject" means a vertebrate, including any member of the class mammalia, including humans and animals, such as horse or dog, and higher primates. In preferred embodiments, the subject is a human.

The term "treating" or "treatment" means an improvement in the condition of a subject having a disease or disorder described herein. For example, treating cancer can refer to one or more of a decrease in the size of one or more tumor(s) in a subject, a decrease or no substantial change in the growth rate of one or more tumor(s) in a subject, a decrease in metastasis in a subject, and an increase in the period of remission for a subject (e.g., as compared to the one or more metric(s) in a subject having a similar cancer receiving no treatment or a different treatment, or as compared to the one or more metric(s) in the same subject prior to treatment). Additional metrics for assessing response to a treatment in a subject having a disease or disorder described herein are known in the art.

To provide a more concise description, some of the quantitative expressions given herein are not qualified with the term "about."" It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. In some embodiments, the term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "alkyl" refers to straight chained and branched saturated hydrocarbon groups containing one to twenty-two carbon atoms, for example, one to twenty carbon atoms, or one to ten carbon atoms, or one to four carbon atoms. The term Cn means the alkyl group has "n" carbon atoms. For example, C4 alkyl refers to an alkyl group that has 4 carbon atoms. C1-C6 alkyl and C1-C6 alkyl refer to an alkyl group having a number of carbon atoms encompassing the entire range (i.e., 1 to 6 carbon atoms), as well as all subgroups (e.g., 1-6, 2-5, 1-5, 3-4, 1, 2, 3, 4, 5, and 6 carbon atoms). Nonlimiting examples of alkyl groups include methyl, ethyl, n-propyl, isopropyl, n-butyl, sec-butyl (2-methylpropyl), tert-butyl (1,1-dimethylethyl), 3,3-dimethylpentyl, and 2-ethylhexyl.

As used herein, the term "haloalkyl" refers to an alkyl group, as described herein, wherein one or more hydrogen atoms are replaced with halogen (e.g., fluoro, chloro, bromo, or iodo). Representative examples of haloalkyl include, but are not limited to, difluoromethyl, trifluoromethyl, 2,2,2-trifluoroethyl, and 1,1-difluoroethyl.

As used herein, the term "alkenyl" refers to an "alkyl" group as defined hereinabove containing 2 to 22 carbon atoms and containing at least one double bond. Representative examples of alkenyl include, but are not limited to, allyl, vinyl, and the like.

As used herein, the term "alkynyl" refers to an "alkyl" group as defined above containing 2 to 22 carbon atoms and containing at least one triple bond.

As used herein, the term "cycloalkyl" refers to a saturated or partially unsaturated (but not aromatic) cyclic hydrocarbon group containing five to seven carbon atoms (e.g., 5, 6, or 7 carbon atoms). The term Cn means the cycloalkyl group has "n" carbon atoms. For example, C5 cycloalkyl refers to a cycloalkyl group that has 5 carbon atoms in the ring. C5-C8 cycloalkyl and C5-C8 cycloalkyl refer to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Cycloalkyl groups include fused, bridged, and spiro ring systems. Nonlimiting examples of cycloalkyl groups include cyclopentyl, cyclohexyl, cycloheptyl, and cyclooctyl.

As used herein, the term "heterocyclyl" is defined similarly as cycloalkyl, except the ring contains one to three heteroatoms independently selected from oxygen, nitrogen, and sulfur. In particular, the term "heterocyclyl" refers to a ring containing a total of four to ten ring atoms, of which 1, 2, or 3 of those atoms are heteroatoms independently selected from the group consisting of oxygen, nitrogen, and sulfur, and the remaining atoms in the ring are carbon atoms. Nonlimiting examples of heterocyclyl groups include tetrahydropyran, azetidinyl, azepanyl, azirldinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyt, piperazinyl, piperidinyl, pyranyl, pyrazolinyl, pyrazolidinyl. pyrrolinyl, pyrrotidinyl, ditetrahydrofuranyl, tetrahydrofuranyl, tetrahydrothienyl, thiadiazolinyl, thiadiazolidinyl, thiazolinyl, thiazolidinyl, thiomorpholinyl, 1.1-dioxidothlomorpholinyl and the like. Heterocyclyl groups can be saturated or partially unsaturated ring systems but not aromatic, and include groups where carbon, nitrogen, and/or sulfurs atoms are oxidized, e.g., to form an oxo (C=O) group, an N-oxide, or a sulfone. Heterocyclyl groups include fused, bridged, and spiro ring systems.

As used herein, the term "heteroaryl" refers to a mono or bicyclic aromatic ring having five to twelve total ring atoms (e.g., a monocyclic aromatic ring with 5-6 total ring atoms), and containing one to five heteroatoms selected from nitrogen, oxygen, and sulfur in the aromatic ring. Heteroaryl rings include groups where carbon, nitrogen, and/or sulfurs atoms are oxidized, e.g., to form an oxo (C=O) group, an N-oxide, or a sulfone. Examples of heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein, the term "hydroxy" or "hydroxyl" refers to an "—OH" group.

As used herein, the term "cyano" refers to a carbon atom triple bonded to a nitrogen atom ("—CN").

Pharmaceutical Compositions

Further disclosed herein are pharmaceutical compositions. Pharmaceutical compositions typically include a pharmaceutically acceptable excipient. Thus, provided herein are pharmaceutical formulations that include a compound described herein and one or more pharmaceutically acceptable excipients.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods of Inhibiting Receptor Activity

Some embodiments provide a method of inhibiting the activity of one or more adenosine receptors selected from the group consisting of A2a, A2b, and A1, comprising contacting one or more of the receptors with a compound of Formula (I), in an amount sufficient to inhibit the activity of the receptor.

In some embodiments, the activity of one or more adenosine receptors selected from the group consisting of A2a, A2b, and A1 is reduced by about 10% to about 95%, for example, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or any value in between. In some embodiments, the activity of one or more adenosine receptors selected from the group consisting of A2a, A2b, and A1 is reduced by about 10% to about 30%. In some embodiments, the activity of one or more adenosine receptors selected from the group consisting of A2a, A2b, and A1 is reduced by about 20% to about 40%. In some embodiments, the activity of one or more adenosine receptors selected from the group consisting of A2a, A2b, and A1 is reduced by about 30% to about 50%. In some embodiments, the activity of one or more adenosine receptors selected from the group consisting of A2a, A2b, and A1 is reduced by about 40% to about 60%. In some embodiments, the activity of one or more adenosine receptors selected from the group consisting of A2a, A2b, and A1 is reduced by about 50% to about 70%. In some embodiments, the activity of one or more adenosine receptors selected from the group consisting of A2a, A2b, and A1 is reduced by about 60% to about 80%. In some embodiments, the activity of one or more adenosine receptors selected from the group consisting of A2a, A2b, and A1 is reduced by about 70% to about 95%.

In some embodiments, the contacting occurs in vitro. In some embodiments, the contacting occurs in vivo.

Methods of Treatment

Some embodiments provide a method of treating cancer in a subject in need thereof, comprising administering to the subject a therapeutically effective amount of a compound of Formula (I), or a pharmaceutically acceptable salt thereof.

In some embodiments, the cancer is a solid tumor.

In some embodiments, the cancer is cancer of the prostate cancer, colon cancer, rectal cancer, colorectal cancer, pancreatic cancer, cervical cancer, stomach cancer, endometrial cancer, brain cancer, liver cancer, bladder cancer, ovarian cancer, testicular cancer, head cancer, neck cancer, skin cancer (including melanoma and basal carcinoma), mesothelial lining cancer, white blood cell cancer (including lymphoma and leukemia), esophageal cancer, breast cancer, muscle cancer, connective tissue cancer, lung cancer (including small-cell lung carcinoma and non-small-cell lung carcinoma), adrenal gland cancer, thyroid cancer, kidney cancer, bone cancer, glioblastoma, mesothelioma, renal cell carcinoma, gastric carcinoma, sarcoma (including Kaposi's sarcoma), choriocarcinoma, cutaneous basocellular carcinoma, or testicular seminoma.

In some embodiments, the cancer is cancer of the prostate cancer, colon cancer, rectal cancer, colorectal cancer, pancreatic cancer, cervical cancer, stomach cancer, endometrial cancer, brain cancer, liver cancer, bladder cancer, ovarian cancer, testicular cancer, head cancer, neck cancer, mesothelial lining cancer, esophageal cancer, breast cancer, muscle cancer, connective tissue cancer, small-cell lung carcinoma, non-small-cell lung carcinoma, adrenal gland cancer, thyroid cancer, kidney cancer, bone cancer, glioblastoma, mesothelioma, renal cell carcinoma, gastric carcinoma, choriocarcinoma, cutaneous basocellular carcinoma, or testicular seminoma.

In some embodiments, the cancer is selected from the group consisting of melanoma, colorectal cancer, pancreatic cancer, breast cancer, prostate cancer, lung cancer, leukemia, a brain tumor, lymphoma, ovarian cancer, Kaposi's sarcoma, renal cell carcinoma, head and neck cancer, and esophageal cancer.

Some embodiments provide a method of treating an immune disease or disorder in a subject in need thereof, comprising administering to the subject a therapeutically effective amount of a compound of Formula (I), or a pharmaceutically acceptable salt thereof.

In some embodiments, the immune disease or disorder is selected from the group consisting ADA-deficiency associated SCID, immune-related kidney failure, asthma, psoriasis, colitis, pancreatitis, allergies, fibrosis, anemia, fibromyalgia, Alzheimer's disease, congestive heart failure, stroke, aortic valve stenosis, arteriosclerosis, osteoporosis, Parkinson's disease, infections, ulcerative colitis, allergic contact dermatitis and other eczemas, systemic sclerosis, and multiple sclerosis.

In some embodiments, the immune disease or disorder is ADA-deficiency associated SCID.

Process for Preparing Compounds of Formula (I)

In some embodiments, compound 3 described herein is prepared as described in Scheme A.

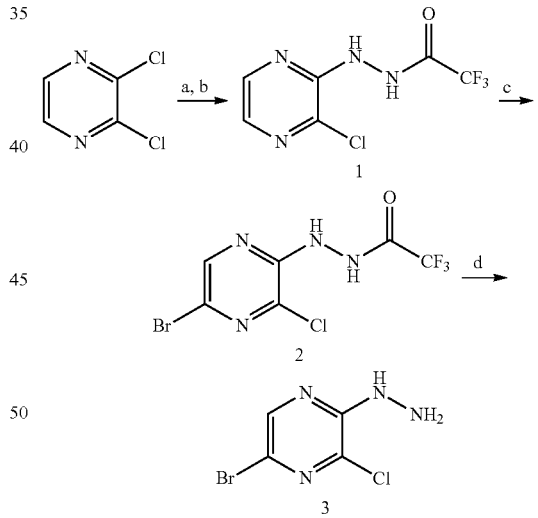

Scheme A a) NH$_2$NH$_2$ EtOH, b) (CF$_3$CO)$_2$O, c) NBS, d) HCl

Intermediate 3 can be prepared via the synthetic route described in Scheme A. Commercially available 2,3-dichloropyrazine undergoes a nucleophilic aromatic substitution (SNAr) reaction with hydrazine in the presence of an organic base such as N,N-diisopropylethylamine to afford the hydrazinylpyrazine adduct which is subsequently converted to compound 1 by treating with trifluoroacetic anhydride. Bromination of 1 with NBS regioselectively undergoes to the para position of an electron-donating group. Removal of the trifluoroacetyl group in 2 by treating with HCl produces compound 3.

In some embodiments, compounds described herein are prepared as described in Scheme B.

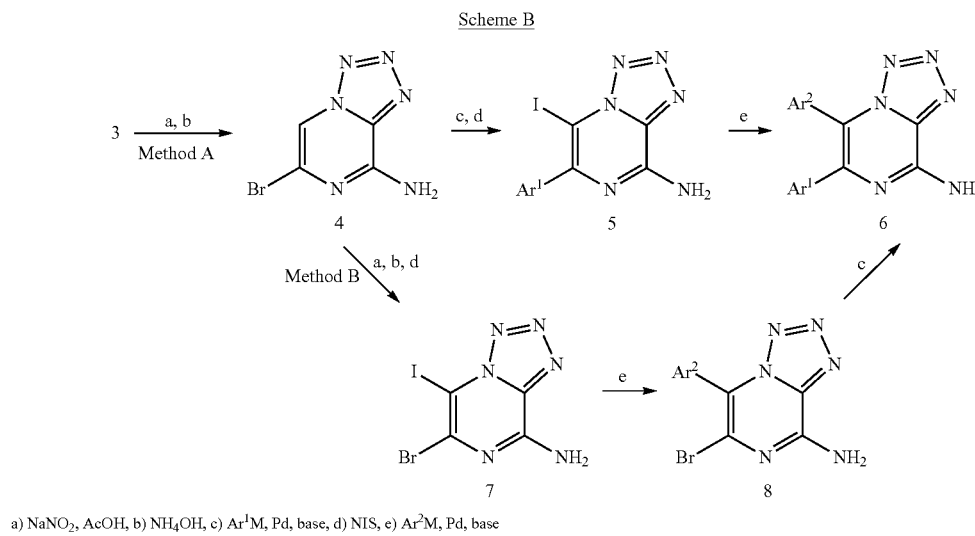

Scheme B a) NaNO₂, AcOH, b) NH₄OH, c) Ar¹M, Pd, base, d) NIS, e) Ar²M, Pd, base

Compound 6 can be prepared via the synthetic route described in Scheme B. A condensation reaction of 3 with NaNO₂ in the presence of AcOH generates 6-bromo-8-chlorotetrazolo[1,5-a]pyrazine that is subsequently converted to compound 4 by a nucleophilic aromatic substitution (SNAr) reaction with NH₄OH. Successively, Ar¹ group is introduced by a cross-coupling reaction such as standard Suzuki (M is B(OR)₂), Stille (M is Sn(alkyl)₃), or Negishi (M is Zn-hal) reaction, and then an iodine is inserted by treating with NIS. Finally, compound 6 is obtained from one of cross-coupling reactions described in step c. Compound 6 can be also synthesized by the alternative sequence as outlined in Method B.

In some embodiments, compounds described herein are prepared as described in Scheme C.

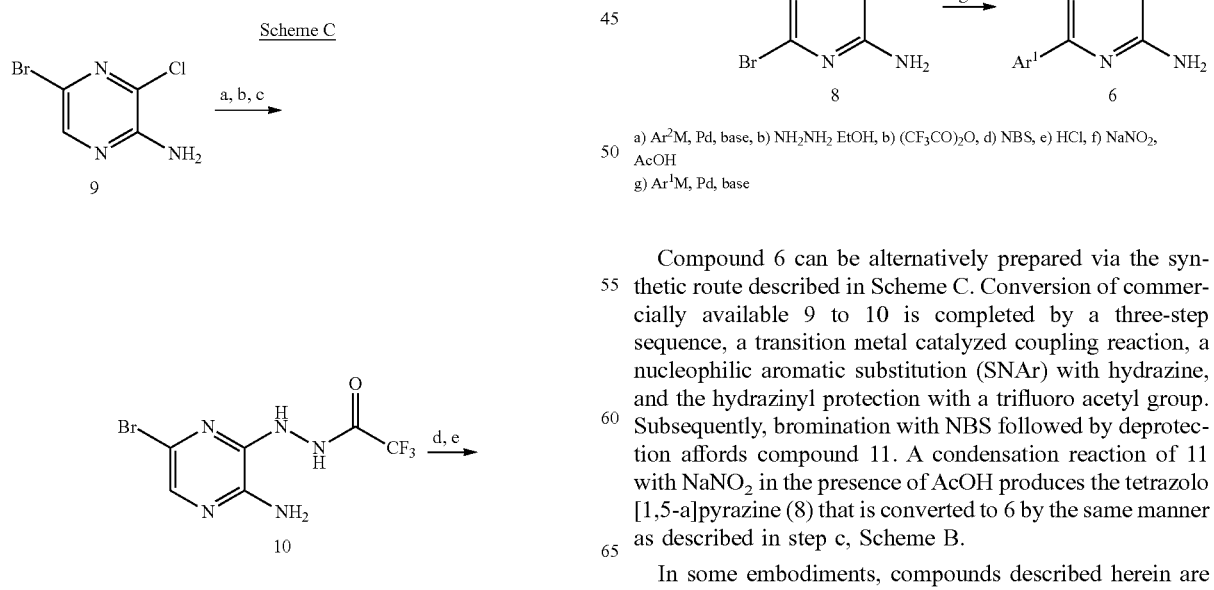

Scheme C a) Ar²M, Pd, base, b) NH₂NH₂ EtOH, b) (CF₃CO)₂O, d) NBS, e) HCl, f) NaNO₂, AcOH
g) Ar¹M, Pd, base Compound 6 can be alternatively prepared via the synthetic route described in Scheme C. Conversion of commercially available 9 to 10 is completed by a three-step sequence, a transition metal catalyzed coupling reaction, a nucleophilic aromatic substitution (SNAr) with hydrazine, and the hydrazinyl protection with a trifluoro acetyl group. Subsequently, bromination with NBS followed by deprotection affords compound 11. A condensation reaction of 11 with NaNO₂ in the presence of AcOH produces the tetrazolo[1,5-a]pyrazine (8) that is converted to 6 by the same manner as described in step c, Scheme B.

In some embodiments, compounds described herein are prepared as described in Scheme D.

Scheme D

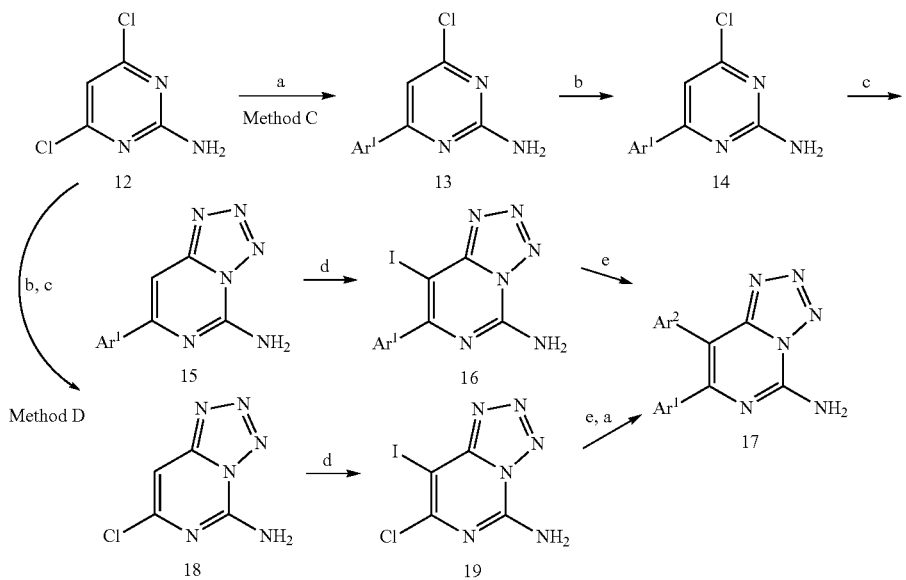

a) Ar¹M, Pd, base, b) N₂H₄, BuOH, c) NaNO₂, AcOH, d) NIS, e) Ar²M, Pd, base

Compound 17 can be prepared via the synthetic route described in Scheme D. Conversion of commercially available 12 to 13 is achieved by a transition metal catalyzed coupling reaction as described in step c, Scheme B. A nucleophilic aromatic substitution (SNAr) reaction of 13 with hydrazine in the presence of an organic base affords compound 14. This adduct undergoes a condensation reaction with NaNO₂ in the presence of AcOH to produce the tetrazolo[1,5-c]pyrimidine (15), followed by iodination to 16 by treating NIS. Subsequently, 17 can be obtained from the same manner as described in step e, Scheme B. Compound 17 can be also synthesized by the alternative sequence as outlined in Method D.

In some embodiments, compounds described herein are prepared as described in Scheme E.

Scheme E

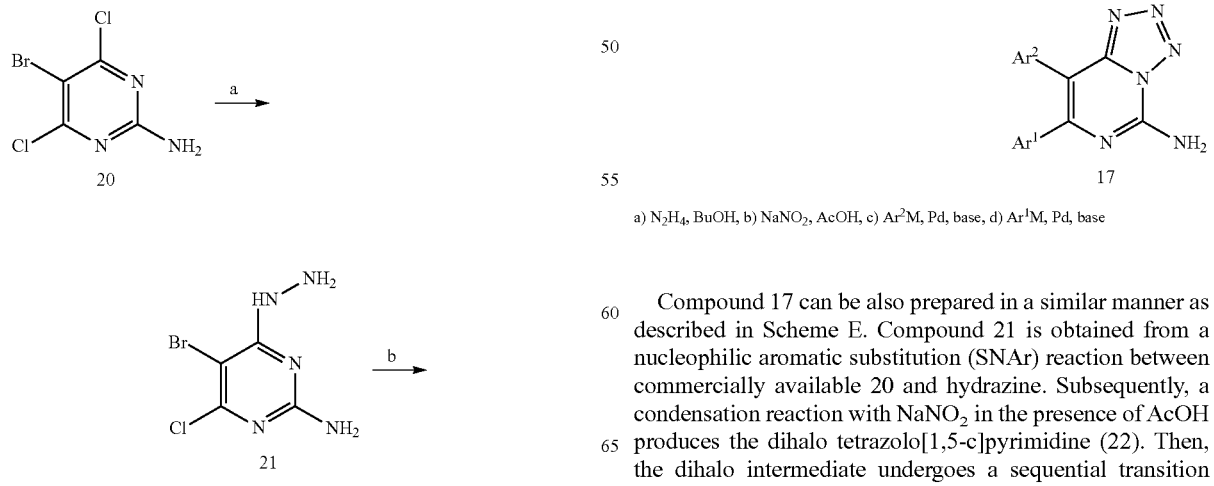

a) N₂H₄, BuOH, b) NaNO₂, AcOH, c) Ar²M, Pd, base, d) Ar¹M, Pd, base

Compound 17 can be also prepared in a similar manner as described in Scheme E. Compound 21 is obtained from a nucleophilic aromatic substitution (SNAr) reaction between commercially available 20 and hydrazine. Subsequently, a condensation reaction with NaNO₂ in the presence of AcOH produces the dihalo tetrazolo[1,5-c]pyrimidine (22). Then, the dihalo intermediate undergoes a sequential transition metal catalyzed coupling reaction to afford 17.

EXAMPLES

Abbreviations

DIEA: N,N-diisopropylethylamine;
DMSO: dimethyl sulfoxide;
Pd(PPh$_3$)$_4$: tetrakis(triphenylphosphine)palladium(0)
Pd(dppf)Cl$_2$: [1,1'-bis(diphenylphosphino)ferrocene]palladium(II) dichloride;
Pd(PPh$_3$)$_2$Cl$_2$: bis(triphenylphosphine)palladium(II) dichloride;
Pd$_2$(dba)$_3$ CHCl$_3$: tris(dibenzylideneacetone)dipalladium (0)-chloroform
CuCl: copper(I) chloride;
PdAMphos: bis(di-tert-butyl(4-dimethylaminophenyl)phosphine)dichloropalladium(II);
TBAF: tetra-n-butylammonium fluoride;
P(t-Bu)$_3$: tri-tert-buytlphosphine;
HBF$_4$: tetrafluoroboric acid;
DBU: 1,8-diazabicyclo[5.4.0]undec-7-ene;
Prep-HPLC: preparative high performance liquid chromatography;
TLC: thin layer chromatography
TFA: trifluoroacetic acid;
CH$_3$CN: acetonitrile;
MeOD: deuterated methanol;
CDCl$_3$: deuterated chloroform
DME: 1,2-dimethoxyethane;
EtOAc/EA: ethyl acetate;
NaOAc: sodium acetate;
Cs$_2$CO$_3$: cesium carbonate
Na$_2$CO$_3$: sodium carbonate
K$_2$CO$_3$: potassium carbonate
Na$_2$SO$_4$: sodium sulfate
K$_3$PO$_4$: tripotassium phosphate
P-TsOH: p-toluenesulfonic acid;
NaNO$_2$: sodium nitrate;
KI: potassium iodide;
THF: tetrahydrofuran;
NBS: N-bromosuccinimide;
NIS: N-iodosuccinimide;
NH$_4$OH: ammonium hydroxide
Br$_2$: bromine;
LiAlH$_4$: lithium aluminium hydride;
NaBH$_4$: Sodium borohydride
TEA: trimethylamine;
EDCI 1-ethyl-3-(3-dimethylaminopropyl)carbodiimide;
hrs: hours;
h or hr: hour.

Synthesis of Compounds

Example 1: 5-(2-chloro-6-methylpyridin-4-yl)-6-(4-fluorophenyl)tetrazolo[1,5-a]pyrazin-8-amine (1-1)

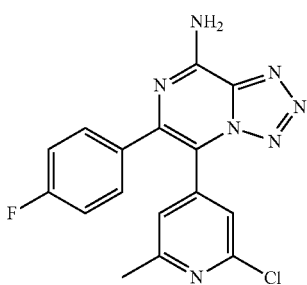

Step 1-1, preparation of 2-chloro-3-hydrazineylpyrazine: A 100 mL round bottom flask was charged with 2,3-dichloropyrazine (10 g, 67.6 mmol), hydrazine hydrate (6.76 g, 135 mmol) and ethanol (40 mL). The resulting mixture was stirred at reflux for 3 h. Reaction progress was monitored by TLC (EtOAc/petroleum ether=2:1). The reaction mixture was cooled to room temperature. The solid was collected by filtration, washed with water (30 mL×2) and dried to afford 8.4 g (86%) of the title compound as a yellow solid. LCMS (M+H)$^+$: 145.0.

Step 1-2, preparation of N'-(3-chloropyrazin-2-yl)-2,2,2-trifluoroacetohydrazide: A 500 mL round bottom flask was charged with 2-chloro-3-hydrazinylpyrazine (20 g, 140 mmol) and THF (180 mL). To the above solution in an ice bath was added dropwise a solution of trifluoroacetic anhydride (35 g, 170 mmol) in THF (20 mL) under anhydrous N$_2$. The resulting solution was stirred for 3 h at 0° C. Reaction progress was monitored by TLC (EtOAc/petroleum ether=1/2). The reaction mixture was diluted with water and then extracted with CH$_2$Cl$_2$ (50 mL×3). The combined organic layers were washed with brine (40 mL), dried over anhydrous Na$_2$SO$_4$ and concentrated in vacuo to afford 29.7 g (89%) of the title compound as a yellow solid. LCMS (M+H)$^+$: 241.0.

Step 1-3, preparation of N'-(5-bromo-3-chloropyrazin-2-yl)-2,2,2-trifluoroacetohydrazide: A 500 mL round bottom flask was charged with N'-(3-chloropyrazin-2-yl)-2,2,2-trifluoroacetohydrazide (17 g, 71 mmol) and CHCl$_3$ (200 mL). To the above solution was added NBS (19 g, 110 mmol) at 0° C. The resulting mixture was warmed to rt and stirred for 1 h. Reaction progress was monitored by TLC (EtOAc/petroleum ether=1/2). The reaction mixture was concentrated in vacuo. The residue was purified by flash column chromatography on silica gel with 20% EtOAc in petroleum ether to afford 17.7 g (76%) of the title compound as a light yellow solid. LCMS (M+H)$^+$: 319.0.

Step 1-4, preparation of 5-bromo-3-chloro-2-hydrazineylpyrazine: A 250 mL round bottom flask was charged with N'-(5-bromo-3-chloropyrazin-2-yl)-2,2,2-trifluoroacetohydrazide (17 g, 53 mmol), concentrated HCl (35 mL) and ethanol (100 mL). The resulting mixture was heated at 80° C. for 4 h. The reaction mixture was then allowed to cool to room temperature and neutralized with Na$_2$CO$_3$. It was then diluted with water and extracted with EtOAc (50 mL×3). The combined organic layers were dried over anhydrous Na$_2$SO$_4$ and concentrated in vacuo. The residue was further purified by flash column chromatography on silica gel with 20% EtOAc in petroleum ether to afford 9.0 g (72%) of the title compound as a yellow solid. LCMS (M+H)$^+$: 222.9.

Step 1-5, preparation of 6-bromo-8-chlorotetrazolo[1,5-a]pyrazine: A 100 mL round bottom flask was charged with 5-bromo-3-chloro-2-hydrazineylpyrazine (200 mg, 0.895 mmol) and AcOH (1 mL). To the above was added dropwise a solution of NaNO$_2$ (68 mg, 0.985 mmol) in water (0.5 mL) at 10° C. The resulting mixture was stirred at 10° C. for 1 h, and the product was precipitated during the stirring. The crystalline solid was collected by filtration, washed with EtOH (10 mL), and dried to afford 150 mg (70%) of the title compound as a red solid. LCMS (M+H)$^+$: 234.0.

Step 1-6, preparation of 6-bromotetrazolo[1,5-a]pyrazin-8-amine: A 50 mL round bottom flask was charged with 6-bromo-8-chlorotetrazolo[1,5-a]pyrazine (20 mg, 85 µmol) and NH$_4$OH (5 mL). The resulting mixture was stirred at 50° C. for 2 h, and the product was formed as solid during the reaction. The reaction was cooled to rt and filtered to afford 10 mg (53%) of the title compound as a grey solid. LCMS (M+H)$^+$: 215.0.

Step 1-7, preparation of 6-(4-fluorophenyl)tetrazolo[1,5-a]pyrazin-8-amine: To a solution of 6-bromotetrazolo[1,5-a]pyrazin-8-amine (2.16 g, 10.1 mmol) in 1,4-dioxane/H$_2$O (3:1, 16 mL) was added (4-fluorophenyl)boronic acid (1.41 g, 10.1 mmol, 1 eq.), Pd(PPh$_3$)$_4$ (1.17 g, 1.01 mmol, 0.1 eq.), and Potassium carbonate (2.79 g, 20.2 mmol, 2 eq.). The reaction mixture was purged with anhydrous N$_2$ for 5 min and stirred at 80° C. for 2 h. The reaction was cooled to rt, quenched with water (50 mL) and extracted with EtOAc (50 mL×3). The combined organic extracts were washed with brine, dried over anhydrous Na$_2$SO$_4$, filtered and concentrated to dryness under reduced pressure to provide the crude product, which was purified by silica gel chromatography to afford the title compound as light yellow solid (2.0 g, 87% yield). LCMS (M+H)$^{3O}$: 231.0.

Step 1-8, preparation of 6-(4-fluorophenyl)-5-iodotetrazolo[1,5-a]pyrazin-8-amine: A 50 mL round bottom flask was charged with 6-(4-fluorophenyl)-[1,2,4]triazolo[4,3-a]pyrazin-8-amine (280 mg, 1.22 mmol) and DMF (5 mL). After cooling to 0° C., the reaction was treated with NIS (231 mg, 1.34 mmol) in one portion. It was slowly warmed to rt and stirred for an additional 2 h. The reaction was quenched with water (50 mL) and extracted with EtOAc (50 mL×3). The combined organic extracts were washed with brine, dried over anhydrous Na$_2$SO$_4$, and concentrated to dryness under reduced pressure to provide the crude product, which was purified by silica gel chromatography to afford the title compound as a light yellow solid (310 mg, 66% yield). LCMS (M+H)$^+$: 357.3.

Step 1-9, preparation of 5-(2-chloro-6-methylpyridin-4-yl)-6-(4-fluorophenyl)tetrazolo[1,5-a]pyrazin-8-amine: To a solution of 6-(4-fluorophenyl)-5-iodotetrazolo[1,5-a]pyrazin-8-amine (300 mg, 842 µmol, 1 equiv.) in 1,4-Dixane/H$_2$O (3:1, 16 mL) was added 2-chloro-6-methyl-4-(4,4,5,5-tetramethyl-1,3,2-dioxaborolan-2-yl)pyridine (320 mg, 1.26 mmol, 1.5 eq.), Pd(dtbpf)Cl$_2$ (54.8 mg, 84.2 µmol, 0.1 eq.), and cesium carbonate (233 mg, 1.68 mmol, 2 eq.). The reaction mixture was purged with N$_2$ for 5 min and stirred at 80° C. for 2 h under N$_2$. The reaction was cooled to rt, quenched with water (50 mL) and extracted with EtOAc (50 mL×3). The combined organic extracts were washed with brine, dried over anhydrous Na$_2$SO$_4$, filtered and concentrated. The residue was purified by silica gel chromatography to afford the crude product. It was further purified by preparative HPLC using a Xselect CSH OBD C18 150 mm×30 mm×5 µm column (eluent: 17% to 4700 (v/v) CH$_3$CN and H$_2$O with 10 mmol/L, NH$_4$HCO$_3$) to give the title compound as a white solid (25.4 mg, 8.5% yield). LCMS (M+H): 356.05. $^1$H NMR (400 MHz, DMSO-d$_6$) δ 8.43 (s, 2H), 7.43-7.37 (m, 2H), 7.34 (d, J=7.9 Hz, 2H), 7.26-7.15 (i, 2H), 2.43 (s, 3H).

The following compounds were prepared similarly to Example 1 with appropriate substituting reagents and substrates at different steps:

| Cmpd No. | Cmpd Structure | MS (M + H)$^+$ | $^1$H NMR |
| --- | --- | --- | --- |
| 1-2 | 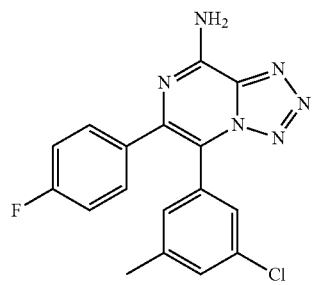 [SMILES: Cc1cc(Cl)cc(-c2c(-c3ccc(F)cc3)nc(N)c3nnnn23)c1] | 356.0 | (300 MHz, DMSO-d$_6$) δ 8.31 (s, 2H), 7.59-7.46 (m, 2H), 7.40-7.26 (m, 2H), 7.15 (s, 1H), 7.08 (s, 1H), 2.34 (s, 3H). |
| 1-3 | | 355.0 | (400 MHz, DMSO-d$_6$) δ 8.24 (s, 2H), 7.44-7.29 (m, 4H), 7.26-7.11 (m, 3H), 2.28 (s, 3H). |

| Cmpd No. | Cmpd Structure | MS (M + H)+ | 1H NMR |
|---|---|---|---|
| 1-8 | | 348.1 | (300 MHz, DMSO-d6) δ 9.13 (s, 1H), 8.59 (s, 1H), 8.38 (s, 2H), 7.94 (d, J = 9.2 Hz, 1H), 7.74-7.64 (m, 1H), 7.52-7.41 (m, 2H), 7.16 (t, J = 8.7 Hz, 2H). |
| 1-9 | | 347.0 | (300 MHz, DMSO-d6) δ 8.70 (s, 1H), 8.28 (s, 2H), 8.01 (s, 1H), 7.69-7.60 (m, 2H), 7.53-7.43 (m, 2H), 7.27-7.12 (m, 3H). |
| 1-10 | | 348.0 | (400 MHz, DMSO-d6) δ 8.85 (s, 1H), 8.24 (s, 2H), 7.95 (s, 1H), 7.85 (d, J = 8.3 Hz, 1H), 7.45-7.35 (m, 3H), 7.15-7.05 (m, 2H). |
| 1-11 | | 358.0 | (300 MHz, DMSO-d6) δ 8.97 (dd, J = 4.2, 1.7 Hz, 1H), 8.35 (d, J = 8.3 Hz, 1H), 8.27 (s, 2H), 8.13 (d, J = 1.9 Hz, 1H), 8.06 (d, J = 8.8 Hz, 1H), 7.76 (dd, J = 8.8, 2.0 Hz, 1H), 7.58 (dd, J = 8.3, 2.4 Hz, 1H), 7.46-7.35 (m, 2H), 7.15-7.04 (m, 2H). |

-continued

| Cmpd No. | Cmpd Structure | MS (M + H)+ | 1H NMR |
|---|---|---|---|
| 1-12 | | 363.9 | (300 MHz, DMSO-d6) δ 9.50 (s, 1H), 8.32 (s, 1H), 8.24 (s, 2H), 8.13 (d, J = 8.5 Hz, 1H), 7.56 (d, J = 8.5 Hz, 1H), 7.44-7.34 (m, 2H), 7.10 (t, J = 8.8 Hz, 2H). |
| 1-14 | | 365.0 | (300 MHz, DMSO-d6) δ 8.54 (s, 1H), 8.34 (s, 2H), 8.14 (d, J = 3.1 Hz, 1H), 7.69 (d, J = 1.2 Hz, 1H), 7.56-7.43 (m, 2H), 7.29 (dd, J = 11.8, 1.3 Hz, 1H), 7.24-7.11 (m, 2H). |
| 1-15 | | 359.0 | (300 MHz, DMSO-d6) δ 9.62 (s, 1H), 9.37 (s, 1H), 8.36-8.30 (m, 3H), 8.11-7.96 (m, 2H), 7.46-7.34 (m, 2H), 7.16-7.03 (m, 2H). |
| 1-16 | | 364.0 | (300 MHz, DMSO-d6) δ 9.45 (bs, 1H), 8.71-8.41 (m, 2H), 8.50 (s, 2H), 8.16 (s, 1H), 7.60-7.48 (m, 2H), 7.31-7.14 (m, 2H). |

-continued

| Cmpd No. | Cmpd Structure | MS (M + H)+ | 1H NMR |
|---|---|---|---|
| 1-17 | | 380.9 | (300 MHz, DMSO-d$_6$) δ 8.64 (s, 1H), 8.30 (s, 2H), 8.10 (s, 1H), 7.67 (d, J = 1.2 Hz, 1H), 7.53 (d, J = 1.2 Hz, 1H), 7.40-7.49 (m, 2H), 7.15 (t, J = 9.0 Hz, 2H) |
| 1-18 | | 362.0 | (300 MHz, DMSO-d$_6$) δ 8.98 (s, 1H), 8.35 (s, 2H), 7.79 (d, J = 9.2 Hz, 1H), 7.63 (d, J = 9.3 Hz, 1H), 7.50-7.40 (m, 2H), 7.16 (t, J = 8.9 Hz, 2H), 2.49 (s, 3H). |
| 1-19 | | 376.1 | (300 MHz, DMSO-d$_6$) δ 9.02 (dd, J = 4.2, 1.6 Hz, 1H), 8.41 (d, J = 8.4 Hz, 1H), 8.33 (s, 2H), 7.92 (s, 1H), 7.76-7.62 (m, 2H), 7.49-7.36 (m, 2H), 7.12 (t, J = 9.9 Hz, 2H). |
| 1-21 | | 379.1 | (300 MHz, DMSO-d$_6$) δ 8.42 (s, 1H), 8.32 (s, 2H), 7.84 (d, J = 3.1 Hz, 1H), 7.52-7.42 (m, 2H), 7.28-7.11 (m, 3H), 2.35 (s, 3H). |

-continued

| Cmpd No. | Cmpd Structure | MS (M + H)+ | 1H NMR |
|---|---|---|---|
| 1-24 | | 395.0 | (300 MHz, DMSO-d6) δ 8.41 (s, 1H), 8.32 (s, 2H), 7.54-7.42 (m, 4H), 7.15 (t, J = 8.9 Hz, 2H), 2.32 (s, 3H). |
| 1-31 | | 379.0 | (300 MHz, DMSO-d6) δ 8.86-8.76 (m, 1H), 8.35 (s, 2H), 8.20 (s, 1H), 8.06 (dd, J = 8.8, 3.0 Hz, 1H), 7.91-7.70 (m, 3H), 7.6-7.54 (m, 1H), 7.51-7.32 (m, 2H), 2.50 (s, 3H). |
| 1-32 | | 338.0 | (300 MHz, DMSO-d6) δ 8.41 (s, 2H), 7.39-7.30 (m, 7H), 2.42 (s, 3H). |
| 1-38 | | 384.1 | (300 MHz, DMSO-d6) δ 8.81 (d, J = 4.4 Hz, 1H), 8.27-8.16 (m, 3H), 8.03 (d, J = 8.7 Hz, 1H), 7.77 (dd, J = 8.7, 1.9 Hz, 1H), 7.45-7.37 (m, 1H), 7.37-7.26 (m, 2H), 6.85-6.75 (m, 2H), 3.69 (s, 3H), 2.53 (s, 3H). |

| Cmpd No. | Cmpd Structure | MS (M + H)+ | 1H NMR |
| --- | --- | --- | --- |
| 1-39 | | 388.0 | (300 MHz, DMSO d6) δ 8.79 (s, 1H), 8.27 (s, 2H), 8.19 (s, 1H), 8.02 (d, J = 8.7 Hz, 1H), 7.82-7.73 (m, 1H), 7.44-7.26 (m, 5H), 2.50 (s, 3H). |
| 1-40 | | 425.1 | (300 MHz, DMSO-d6) δ 8.82-8.77 (m, 1H), 8.27 (s, 2H), 8.13 (s, 1H), 8.02 (d, J = 8.7 Hz, 1H), 7.87-7.78 (m, 1H), 7.43-7.34 (m, 3H), 7.25-7.12 (m, 2H), 2.91 (s, 3H), 2.78 (s, 3H), 2.44 (s, 3H). |
| 1-44 | | 379.0 | (300 MHz, DMSO-d6) δ 8.82 (d, J = 4.3 Hz, 1H), 8.35 (s, 2H), 8.20 (d, J = 1.9 Hz, 1H), 8.05 (d, J = 8.7 Hz, 1H), 7.81 (dd, J = 8.7, 1.9 Hz, 1H), 7.78-7.69 (m, 2H), 7.59-7.49 (m, 2H), 7.42 (d, J = 4.4 Hz, 1H), 2.50 (s, 3H). |
| 1-45 | | 388.0 | (300 MHz, DMSO-d6) δ 8.77 (d, J = 4.4 Hz, 1H), 8.36 (s, 2H), 8.07-7.89 (m, 3H), 7.38-7.15 (m, 5H), 2.43 (s, 3H). |

-continued

| Cmpd No. | Cmpd Structure | MS (M + H)+ | 1H NMR |
|---|---|---|---|
| 1-46 | | 355.0 | (300 MHz, DMSO-d$_6$) δ 8.82 (d, J = 4.3 Hz, 1H), 8.49-8.41 (m, 2H), 8.40-8.34 (m, 2H), 8.21 (s, 1H), 8.07 (d, J = 8.7 Hz, 1H), 7.88-7.79 (m, 1H), 7.46-7.38 (m, 1H), 7.37-7.29 (m, 2H), 2.49 (s, 3H). |
| 1-47 | | 355.0 | (300 MHz, DMSO-d$_6$) δ 8.81 (d, J = 4.3 Hz, 1H), 8.51-8.39 (m, 2H), 8.38-8.32 (m, 2H), 8.19 (d, J = 2.0 Hz, 1H), 8.05 (d, J = 8.7 Hz, 1H), 7.88-7.73 (m, 2H), 7.45-7.37 (m, 1H), 7.37-7.26 (m, 1H), 2.49 (s, 3H). |
| 1-48 | | 397.0 | (300 MHz, DMSO-d$_6$) δ 8.59 (s, 1H), 8.33 (s, 2H), 8.03-7.95 (m, 1H), 7.82 (d, J = 9.4 Hz, 1H), 7.58-7.38 (m, 4H), 7.22-7.10 (m, 2H). |
| 1-49 | | 379.0 | (300 MHz, DMSO-d$_6$) δ 8.79 (d, J = 4.4 Hz, 1H), 8.48 (s, 2H), 8.08-7.97 (m, 2H), 7.91-7.77 (m, 2H), 7.68-7.46 (m, 3H), 7.39 (d, J = 4.4 Hz, 1H), 2.43 (s, 3H). |

| Cmpd No. | Cmpd Structure | MS (M + H)+ | 1H NMR |
|---|---|---|---|
| 1-50 | 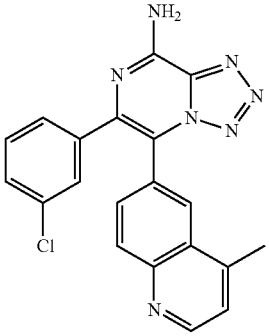 [SMILES: Cc1ccnc2ccc(-c3c(-c4cccc(Cl)c4)nc(N)c4nnnn34)cc12] | 388.0 | (300 MHz, DMSO-d6) δ 8.81 (d, J = 4.4 Hz, 1H), 8.32 (s, 2H), 8.22 (s, 1H), 8.05 (d, J = 8.7 Hz, 1H), 7.87-7.78 (m, 1H), 7.56-7.49 (m, 1H), 7.42 (d, J = 4.4 Hz, 1H), 7.38-7.29 (m, 1H), 7.28-7.16 (m, 2H), 2.49 (s, 3H). |
| 1-51 | 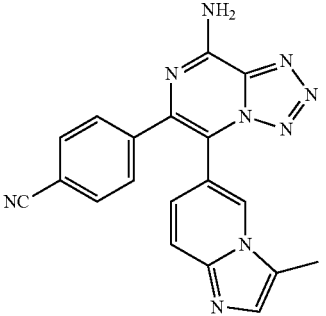 [SMILES: Cc1cnc2ccc(-c3c(-c4ccc(C#N)cc4)nc(N)c4nnnn34)cn12] | 368.1 | (400 MHz, DMSO-d6) δ 8.44 (s, 1H), 8.37 (s, 2H), 7.79 (d, J = 8.1 Hz, 2H), 7.62 (dd, J = 8.6, 2.8 Hz, 3H), 7.45 (s, 1H), 7.23 (d, J = 9.3 Hz, 1H), 2.34 (s, 3H). |
| 1-53 | 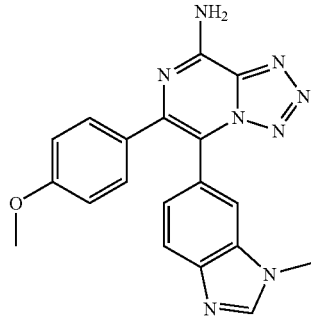 [SMILES: COc1ccc(-c2nc(N)c3nnnn3c2-c2ccc3ncn(C)c3c2)cc1] | 373.1 | (300 MHz, DMSO-d6) δ 8.29 (s, 1H), 8.09 (s, 2H), 7.81 (s, 1H), 7.67 (d, J = 8.3 Hz, 1H), 7.36-7.26 (m, 2H), 7.18 (dd, J = 8.3, 1.6 Hz, 1H), 6.83-6.74 (m, 2H), 3.80 (s, 3H), 3.68 (s, 3H). |
| 1-54 | 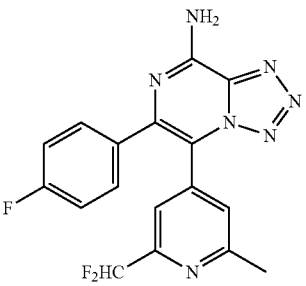 [SMILES: Cc1cc(-c2c(-c3ccc(F)cc3)nc(N)c3nnnn23)cc(C(F)F)n1] | 372.0 | (300 MHz, DMSO-d6) δ 8.43 (s, 2H), 7.51 (d, J = 14.9 Hz, 2H), 7.42-7.31 (m, 2H), 7.25-7.14 (m, 2H), 6.82 (t, J = 54.8 Hz, 1H), 3.34 (s, 3H). |

| Cmpd No. | Cmpd Structure | MS (M + H)+ | 1H NMR |
|---|---|---|---|
| 1-55 | | 410.0 | (300 MHz, DMSO-d$_6$) δ 8.64 (s, 2H), 7.94 (s, 1H), 7.86 (s, 1H), 7.48-7.35 (m, 2H), 7.31-7.18 (m, 2H). |
| 1-56 | | 373.1 | (300 MHz, DMSO-d$_6$) δ 8.46 (s, 1H), 8.21 (s, 2H), 7.60 (d, J = 9.3 Hz, 1H), 7.51-7.36 (m, 3H), 7.20 (d, J = 9.3 Hz, 1H), 6.86 (d, J = 8.3 Hz, 2H), 3.71 (s, 3H), 2.27 (s, 3H). |

Example 2: 5-(8-amino-6-(4-fluorophenyl)tetrazolo[1,5-a]pyrazin-5-yl)-1-methylpyridin-2(1H)-one (1-4)

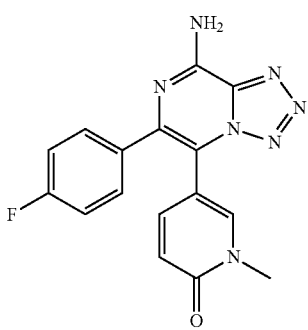 [SMILES: Cn1cc(-c2c(-c3ccc(F)cc3)nc(N)c3nnnn23)ccc1=O]

Step 2-1, preparation of 5-(8-amino-6-(4-fluorophenyl)tetrazolo[1,5-a]pyrazin-5-yl)-1-methylpyridin-2(1H)-one: The title compound was prepared by using the same procedure as described in step 1-9, Example 1. The crude product was purified by preparative HPLC using a YMC-Actus Triart C18 ExRS 150 mm×30 mm×5 m column (eluent: 49% to 79% (v/v) CH$_3$CN and H$_2$O with 10 mmol/L NH$_4$HCO$_3$) to give the desired product as a white solid. LCMS (M+H)$^{30}$: 338.0. $^1$H NMR (400 MHz, DMSO-d$_6$) δ 8.21 (s, 2H), 7.89 (d, J=2.5 Hz, 1H), 7.56-7.46 (m, 2H), 7.39 (dd, J=9.4, 2.6 Hz, 1H), 7.23 (t, 2H), 6.45 (d, J=9.4 Hz, 1H), 3.40 (s, 3H).

Example 3: 6-(4-fluorophenyl)-5-(8-methoxyquinolin-6-yl)tetrazolo[1,5-a]pyrazin-8-amine (1-5)

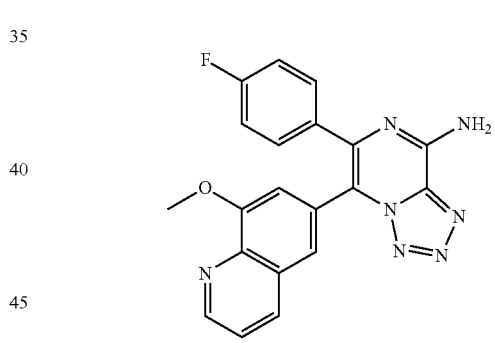

Step 3-1, preparation of (8-methoxyquinolin-6-yl)boronic acid: A flame-dried 100 mL round bottom flask was charged with triisopropyl borate (94.8 mg, 504 μmol), 6-bromo-8-methoxyquinoline (100 mg, 420 μmol) and THF (10 mL). The mixture was cooled to −78° C., and 1.6 M n-BuLi (0.32 mL, 504 μmol) was added dropwise to the reaction over 1 h under an inert atmosphere. The mixture was stirred for 0.5 h at −78° C. and then warmed to −20° C. The reaction was treated with 2.0 N HCl (5 mL), warmed to rt, and concentrated under reduced pressure until a precipitate formed. The crude product as HCl salt was obtained by filtration. It was further purified by C18 reverse column (eluent: 5% to 10% (v/v) CH$_3$CN and H$_2$O) to give the title compound as a white solid (60 mg, 70% yield). LCMS (M+H)$^+$: 204.05.

Step 3-2, preparation of 6-(4-fluorophenyl)-5-(8-methoxyquinolin-6-yl)tetrazolo[1,5-a]pyrazin-8-amine: The title compound was prepared by using the same procedure as described in step 1-9, Example 1. The crude product was purified by preparative HPLC using a YMC-Actus Triart C18 ExRS 150 mm×30 mm×5 m column (eluent: 49% to 79% (v/v) CH₃CN and H₂O with 10 mmol/L NH₄HCO₃) to afford the desired product as a white solid. LCMS (M+H)⁺: 388.1. ¹H NMR (400 MHz, DMSO-d₆) δ 8.90 (s, 1H), 8.32-8.24 (m, 3H), 7.66 (s, 1H), 7.61-7.54 (m, 1H), 7.48-7.40 (m, 2H), 7.21 (s, 1H), 7.11 (t, J=8.7 Hz, 2H), 3.78 (s, 3H).

Example 4: 6-(4-fluorophenyl)-5-(4-methylquinolin-6-yl)tetrazolo[1,5-a]pyrazin-8-amine (1-6)

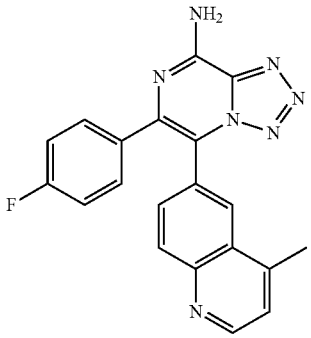 [SMILES: Cc1ccnc2ccc(-c3c(-c4ccc(F)cc4)nc(N)c4nnnn34)cc12]

Step 4-1, preparation of 6-(4-fluorophenyl)-5-(4-methylquinolin-6-yl)tetrazolo[1,5-a]pyrazin-8-amine: (4-methylquinolin-6-yl)boronic acid was synthesized starting from 6-bromo-4-methylquinoline as described in step 3-1, Example 3. The title compound was prepared by using the same procedure as described in step 1-9, Example 1. The crude product was purified by preparative HPLC using a YMC-Actus Triart C18 ExRS 150 mm×30 mm×5 m column (eluent: 49% to 79% (v/v) CH₃CN and H₂O with 10 mmol/L NH₄HCO₃) to give the desired product as a white solid. LCMS (M+H)⁺: 372.05. ¹H NMR (400 MHz, DMSO-d₆) δ 8.83-8.74 (m, 1H), 8.21-8.13 (m, 1H), 8.06-7.98 (m, 1H), 7.83-7.76 (m, 1H), 7.44-7.35 (m, 3H), 7.14-7.02 (m, 2H), 2.48 (s, 3H), —NH₂ was not observed.

Example 5: 6-(4-fluorophenyl)-5-(3-methylimidazo[1,2-a]pyridin-6-yl)tetrazolo[1,5-a]pyrazin-8-amine (1-7)

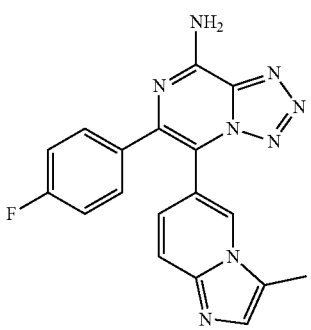 [SMILES: Cc1cnc2ccc(-c3c(-c4ccc(F)cc4)nc(N)c4nnnn34)cn12]

Step 5-1, preparation of 6-(4-fluorophenyl)-5-(3-methylimidazo[1,2-a]pyridin-6-yl)tetrazolo[1,5-a]pyrazin-8-amine: The title compound was prepared by using the same procedure as described in step 1-9, Example 1. The crude product was purified by preparative HPLC using a XBridge Prep OBD C18 150 mm×30 mm×5 m column (eluent: 19% to 49% (v/v) CH₃CN and H₂O with 10 mmol/L NH₄HCO₃) to give the desired product as a white solid. LCMS (M+H)⁺: 361.1. ¹H NMR (400 MHz, DMSO-d₆) δ 8.42 (s, 1H), 8.27 (s, 2H), 7.59 (d, J=9.4 Hz, 1H), 7.52-7.39 (m, 3H), 7.26-7.07 (m, 3H), 2.33 (s, 3H).

Example 6: 6-(4-fluorophenyl)-5-(1-methyl-1H-benzo[d]imidazol-6-yl)tetrazolo[1,5-a]pyrazin-8-amine (1-13)

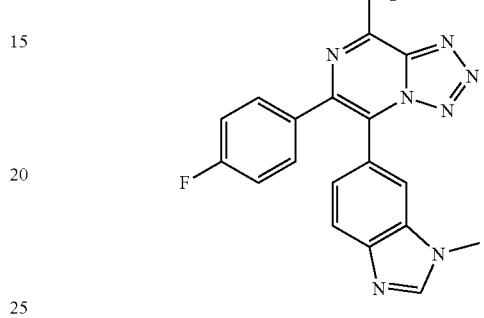

Step 6-1, preparation of 6-(4-fluorophenyl)-5-(1-methyl-1H-benzo[d]imidazol-6-yl)tetrazolo[1,5-a]pyrazin-8-amine: The title compound was prepared by using the same procedure as described in step 1-9, Example 1. The crude product purified by C18 reverse column (eluent: 30% to 50% (v/v) ACN and Water with 10 mmol/L NH₄HCO₃) to give the desired product as a white solid. LCMS (M+H)⁺: 361.05. ¹H NMR (300 MHz, DMSO-d₆) δ 8.29 (s, 1H), 8.15 (s, 2H), 7.76 (s, 1H), 7.67 (d, J=8.4 Hz, 1H), 7.46-7.33 (m, 2H), 7.19 (dd, J=8.3, 1.6 Hz, 1H), 7.15-7.00 (m, 2H), 3.79 (s, 3H).

Example 7: (6-(8-amino-6-(4-fluorophenyl)tetrazolo[1,5-a]pyrazin-5-yl)imidazo[1,2-a]pyridin-3-yl)methanol (1-20)

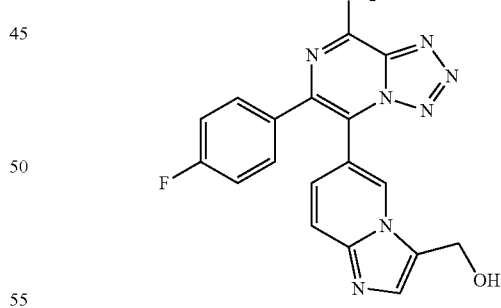

Step 7-1, preparation of (6-bromoimidazo[1,2-a]pyridin-3-yl)methanol: To a solution of 6-bromoimidazo[1,2-a]pyridine-3-carbaldehyde (900 mg, 4 mmol) in MeOH/DCM/H₂O (8/2/2 mL) was dropwisely added NaBH₄ (302 mg, 8 mmol) at 0° C. under anhydrous N₂. The reaction mixture was stirred at 0° C. for 2 h under N₂. The reaction progress was monitored by LCMS and TLC. The reaction was quenched with water and extracted with EtOAc (3×50 mL). The combined organic layers were washed with brine, dried over anhydrous sodium sulfate, filtered and concentrated. The residue was purified by silica gel column chromatography to afford the title compound as a white solid (800 mg, 88% yield). LCMS (M+H)⁺: 227.1.

Step 7-2, preparation of (3-(hydroxymethyl)imidazo[1,2-a]pyridin-6-yl)boronic acid: To a solution of (6-bromoimidazo[1,2-a]pyridin-3-yl)methanol (200 mg, 881 µmol) in 1,4-dioxane (10 mL) was added 4,4,4',4',5,5,5',5'-octamethyl-2,2'-bi(1,3,2-dioxaborolane) (447 mg, 1.76 mmol), PdCl₂ (64.4 mg, 88.1 µmol) and KOAc (170 mg, 1.76 mmol). The reaction was purged with anhydrous N₂ and stirred at 90° C. for 2 h under N₂. The reaction was cooled to rt, filtered and extracted with EtOAc (50 mL×3). The combined organic extracts were washed with brine, dried over anhydrous Na₂SO₄, filtered and concentrated to afford the title compound as a off-white solid (119 mg, 70% yield). LCMS (M+H)⁺: 193.2.

Step 7-3, preparation of (6-(8-amino-6-(4-fluorophenyl)tetrazolo[1,5-a]pyrazin-5-yl)imidazo[1,2-a]pyridin-3-yl)methanol: The title compound was prepared by using the same procedure as described in step 1-9, Example 1. The crude product was purified by preparative HPLC using a XBridge Prep OBD C18 150 mm×30 mm×5 m column (eluent: 15% to 41% (v/v) CH₃CN and H₂O with 10 mmol/L NH₄HCO₃) to give the desired product as an off-white solid. LCMS (M+H)⁺: 377.1. ¹H NMR (400 MHz, DMSO-d₆) δ 8.54 (s, 1H), 7.64 (d, J=9.4 Hz, 1H), 7.56 (s, 1H), 7.43-7.52 (m, 2H), 7.29 (dd, J=9.3, 1.7 Hz, 1H), 7.14 (t, J=9.0, 2.5 Hz, 2H), 4.67 (s, 2H), —NH₂ was not observed.

Example 8: 6-(8-amino-6-(4-fluorophenyl)tetrazolo[1,5-a]pyrazin-5-yl)imidazo[1,2-a]pyridine-3-carbonitrile (1-22)

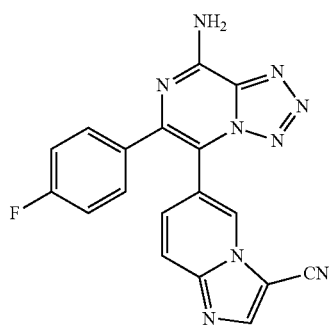 [SMILES: N#Cc1cnc2ccc(-c3c(-c4ccc(F)cc4)nc(N)c4nnnn34)cn12]

Step 8-1, preparation of 6-(8-amino-6-(4-fluorophenyl)tetrazolo[1,5-a]pyrazin-5-yl)imidazo[1,2-a]pyridine-3-carbonitrile: The title compound was prepared by using the same procedure as described in step 1-9, Example 1. The crude product was purified by preparative HPLC using a XBridge Prep OBD C18 150 mm×30 mm×5 m column (eluent: 15% to 41% (v/v) CH₃CN and H₂O with 10 mmol/L NH₄HCO₃) to afford the desired product as a white solid. LCMS (M+H)⁺: 372.1. ¹H NMR (300 MHz, DMSO-d₆) δ 8.91 (s, 1H), 8.53 (s, 1H), 8.36 (s, 2H), 7.91 (dd, J=9.2, 1.0 Hz, 1H), 7.56-7.44 (m, 3H), 7.21-7.10 (m, 2H).

Example 9: 5-(3-chloroimidazo[1,2-a]pyridin-6-yl)-6-(4-fluorophenyl)tetrazolo[1,5-a]pyrazin-8-amine (1-23)

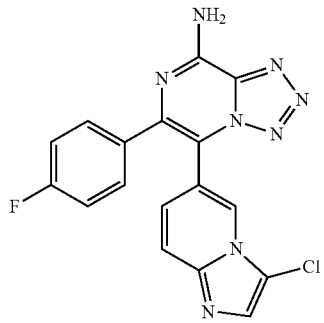 [SMILES: Nc1nc(-c2ccc(F)cc2)c(-c2ccc3ncc(Cl)n3c2)n2nnnc12]

Step 9-1, preparation of 5-(3-chloroimidazo[1,2-a]pyridin-6-yl)-6-(4-fluorophenyl)tetrazolo[1,5-a]pyrazin-8-amine: (3-Chloroimidazo[1,2-a]pyridin-6-yl)boronic acid was synthesized starting from 6-bromo-3-chloroimidazo[1,2-a]pyridine as described in step 3-1, Example 3. The title compound was prepared by using the same procedure as described in step 1-9, Example 1. The crude product was further by preparative HPLC using a XBridge Prep OBD C18 Column 150 mm×30 mm×5 m column (eluent: 31% to 43% (v/v) CH₃CN and H₂O with 10 mmol/L NH₄HCO₃) to give the desired product as a white solid. LCMS (M+H)⁺: 381.0. ¹H NMR (300 MHz, DMSO-d₆) δ 8.55 (s, 1H), 8.31 (s, 2H), 7.80 (s, 1H), 7.72 (d, J=9.3 Hz, 1H), 7.47 (dd, J=8.6, 5.7 Hz, 2H), 7.37-7.28 (m, 1H), 7.15 (t, J=8.8 Hz, 2H).

Example 10: 5-(2-chloro-6-methylpyridin-4-yl)-6-(2-fluorophenyl)tetrazolo[1,5-a]pyrazin-8-amine (1-26)

Step 10-1, preparation of 5-(2-chloro-6-methylpyridin-4-yl)-6-(2-fluorophenyl)tetrazolo[1,5-a]pyrazin-8-amine: The title compound was prepared by using the similar procedures as described in the synthesis of Example 1. The crude product was purified by preparative HPLC using a XBridge Prep OBD C18 150 mm×30 mm×5 m column (eluent: 27% to 52% (v/v) CH₃CN and H₂O with 10 mmol/L NH₄HCO₃) to afford the desired product as a white solid. LCMS (M+H)⁺: 356.0. ¹H NMR (300 MHz, DMSO-d₆) δ 8.49 (s, 2H), 7.54-7.42 (m, 2H), 7.32-7.14 (m, 4H), 2.40 (s, 3H).

Example 11: 5-(2-chloro-6-methylpyridin-4-yl)-6-(3-fluorophenyl)tetrazolo[1,5-a]pyrazin-8-amine (1-27)

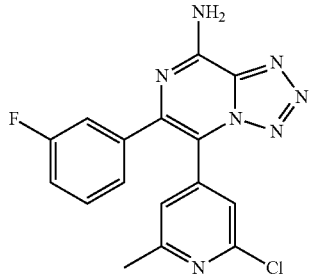 [SMILES: Cc1cc(-c2c(-c3cccc(F)c3)nc(N)c3nnnn23)cc(Cl)n1]

Step 11-1, preparation of 5-(2-chloro-6-methylpyridin-4-yl)-6-(3-fluorophenyl)tetrazolo[1,5-a]pyrazin-8-amine: The title compound was prepared by using the similar procedures as described in the synthesis of Example 1. The crude product was purified by preparative HPLC using a XBridge Prep OBD C18 150 mm×30 mm×5 m column (eluent: 29% to 54% (v/v) $CH_3CN$ and $H_2O$ with 10 mmol/L $NH_4HCO_3$) to afford the desired product as a white solid. LCMS (M+H)$^+$: 356.0. $^1$H NMR (300 MHz, DMSO-$d_6$) δ 8.46 (s, 2H), 7.44-7.33 (m, 3H), 7.28-7.17 (m, 2H), 7.16-7.07 (m, 1H), 2.44 (s, 3H).

Example 12: 6-(2,4-difluorophenyl)-5-(4-methylquinolin-6-yl)tetrazolo[1,5-a]pyrazin-8-amine (1-43)

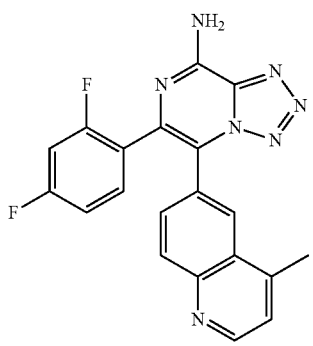 [SMILES: Cc1ccnc2ccc(-c3c(-c4ccc(F)cc4F)nc(N)c4nnnn34)cc12]

Step 12-1, preparation of 6-(2,4-difluorophenyl)-5-(4-methylquinolin-6-yl)tetrazolo[1,5-a]pyrazin-8-amine: The title compound was prepared by using the similar procedures as described in the synthesis of Example 1. The crude product was purified by preparative HPLC using a XBridge Prep OBD C18 150 mm×30 mm×5 m column (eluent: 25% to 46% (v/v) $CH_3CN$ and $H_2O$ with 10 mmol/L $NH_4HCO_3$) to afford the desired product as a white solid. LCMS (M+H)$^+$: 390.0. $^1$H NMR (300 MHz, DMSO-$d_6$) δ 8.79 (d, J=4.3 Hz, 1H), 8.36 (s, 2H), 8.09-7.99 (m, 2H), 7.92-7.82 (m, 1H), 7.63-7.49 (m, 1H), 7.39 (d, J=4.4 Hz, 1H), 7.22-7.07 (m, 2H), 2.46 (s, 3H).

Example 13: 7-(4-fluorophenyl)-8-(3-methylimidazo[1,2-a]pyridin-6-yl)tetrazolo[1,5-c]pyrimidin-5-amine (1-25)

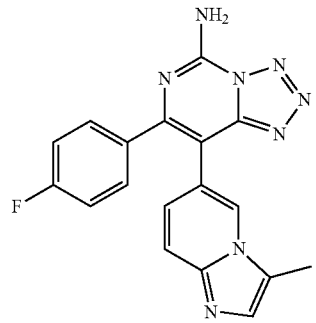 [SMILES: Cc1cnc2ccc(-c3c(-c4ccc(F)cc4)nc(N)n4nnnc34)cn12]

Step 13-1, preparation of 4-chloro-6-(4-fluorophenyl)pyrimidin-2-amine: To a solution of 4,6-dichloropyrimidin-2-amine (10 g, 61 mmol, 1 eq.) in 1,4-dioxane/$H_2O$ (20/1, 210 mL) was added (4-fluorophenyl)boronic acid (3.4 g, 24 mmol, 0.4 eq.), Pd(dppf)$Cl_2$ (2.2 g, 3 mmol, 0.05 eq.), and $K_2CO_3$ (17 g, 0.12 mol, 2 eq.). The reaction mixture was purged with anhydrous $N_2$ and then was stirred at 80° C. for 2 h. The reaction was cooled to rt, quenched with water (200 mL) and extracted with EA (500 mL×3). The combined organic extracts were washed with brine, dried over anhydrous $Na_2SO_4$, filtered, and concentrated under reduced pressure. The residue was purified by silica gel chromatography to afford the title compound as a white solid (2.0 g, 14.6% yield). LCMS (M+H)$^+$: 224.2.

Step 13-2, preparation of 4-(4-fluorophenyl)-6-hydrazineylpyrimidin-2-amine: To a solution of 4-chloro-6-(4-fluorophenyl)pyrimidin-2-amine (1.0 g, 4 mmol, 1 eq.) in BuOH (10 mL) was added $N_2H_4·H_2O$ (1.2 g, 0.03 mol, 6 eq.). The reaction was stirred at 100° C. for 0.5 h under $N_2$. It was cooled to rt, quenched with water (10 mL) and extracted with EA (20 mL×3). The combined organic extracts were washed with brine, dried over anhydrous $Na_2SO_4$, filtered and concentrated under reduced pressure. The residue was purified by silica gel chromatography to afford the title compound as a white solid (0.9 g, 90% yield). LCMS (M+H)$^+$: 220.05.

Step 13-3, preparation of 7-(4-fluorophenyl)tetrazolo[1,5-c]pyrimidin-5-amine: To a solution of 4-(4-fluorophenyl)-6-hydrazineylpyrimidin-2-amine (700 mg, 3.19 mmol, 1 eq.) in AcOH/$H_2O$ (1/1, 10 mL) was added $NaNO_2$ (242 mg, 3.51 mmol, 1.1 eq.). The reaction was stirred at 10° C. for 2 h under $N_2$. The reaction was quenched with water (50 mL) and extracted with EA (50 mL×3). The combined organic extracts were washed with brine, dried over anhydrous $Na_2SO_4$, filtered and concentrated. The crude product was purified by silica gel chromatography to afford the title compound as a yellow solid (500 mg, 68% yield). LCMS (M+H)$^+$: 231.1.

Step 13-4, preparation of 7-(4-fluorophenyl)-8-iodotetrazolo[1,5-c]pyrimidin-5-amine: To a solution of 7-(4-fluorophenyl)tetrazolo[1,5-c]pyrimidin-5-amine (200 mg, 869 μmol, 1 eq.) in DMF (5 mL) was added NIS (293 mg, 1.3 mmol, 1.5 eq.) at 0° C. The reaction was stirred at 25° C. for 16 h under $N_2$, quenched with water (5 mL) and extracted with EA (10 mL×3). The combined organic extracts were washed with brine, dried over anhydrous $Na_2SO_4$, filtered and concentrated under reduced pressure. The residue was purified by silica gel chromatography to afford the title compound as a yellow solid (190 mg, 62% yield). LCMS (M+H)+: 356.9.

Step 13-5, preparation of 7-(4-fluorophenyl)-8-(3-methylimidazo[1,2-a]pyridin-6-yl)tetrazolo[1,5-c]pyrimidin-5-amine: To a solution of 7-(4-fluorophenyl)-8-iodotetrazolo[1,5-c]pyrimidin-5-amine (190 mg, 534 μmol, 1 eq.) in 1,4-dioxane/H$_2$O (3/1, 12 mL) was added 3-methyl-6-(4,4,5,5-tetramethyl-1,3,2-dioxaborolan-2-yl)imidazo[1,2-a]pyridine (165 mg, 640 μmol, 1.5 eq.), Pd(dtbpf)Cl$_2$ (34.8 mg, 53.4 μmol, 0.1 eq.), and K$_3$PO$_4$ (226 mg, 1.07 mmol, 2 eq.). The reaction mixture was purged with anhydrous N$_2$ for 5 min, and then stirred at 60° C. for 2 h under N$_2$. The reaction was cooled to rt, quenched with water (50 mL) and extracted with EA (50 mL×3). The combined organic extracts were washed with brine, dried over anhydrous Na$_2$SO$_4$, filtered and concentrated under reduced pressure. The residue was purified by silica gel chromatography to afford the crude product, which was further purified by preparative HPLC using a XBridge Prep C18 OBD Column 150 mm×30 mm×5 m column (eluent: 15% to 40% (v/v) CH$_3$CN and H$_2$O with 10 mmol/L NH$_4$HCO$_3$) to afford the title compound as a white solid (20.7 mg, 11% yield). LCMS (M+H)+: 361.1. $^1$H NMR (400 MHz, DMSO-d$_6$) δ 8.82-8.78 (m, 2H), 8.32 (s, 1H), 7.58-7.44 (m, 3H), 7.41 (s, 1H), 7.28-7.13 (m, 2H), 6.94 (d, J=9.3, 1H), 2.38 (d, J=1.0 Hz, 3H).

Example 14: 8-(2,6-dimethylpyridin-4-yl)-7-(4-fluorophenyl)tetrazolo[1,5-c]pyrimidin-5-amine (1-28)

Example 15: 7-(4-fluorophenyl)-8-(1-methyl-1H-benzo[d]imidazol-6-yl)tetrazolo[1,5-c]pyrimidin-5-amine (1-30)

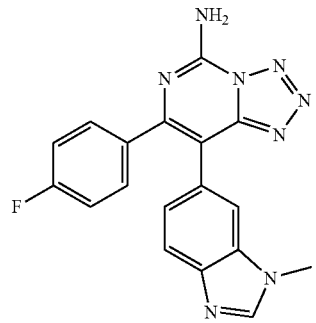

Step 15-1, preparation of 7-(4-fluorophenyl)-8-(1-methyl-1H-benzo[d]imidazol-6-yl)tetrazolo[1,5-c]pyrimidin-5-amine: The title compound was prepared by using the similar procedure as described in step 13-5, Example 13. The crude product was purified by preparative HPLC using a XBridge Prep OBD C18 150 mm×30 mm×5 m column (eluent: 33% to 53% (v/v) CH$_3$CN and H$_2$O with 10 mmol/L NH$_4$HCO$_3$) to afford the desired product as a white solid. LCMS (M+H)+: 361.1. $^1$H NMR (300 MHz, DMSO-d$_6$) δ 8.64 (s, 2H), 8.20 (s, 1H), 7.64-7.50 (m, 2H), 7.40 (dd, J=8.8, 5.6 Hz, 2H), 7.14-6.95 (m, 3H), 3.77 (s, 3H).

Example 16: 8-(2-chloro-6-(trifluoromethyl)pyridin-4-yl)-7-(4-fluorophenyl)tetrazolo[1,5-c]pyrimidin-5-amine (1-34)

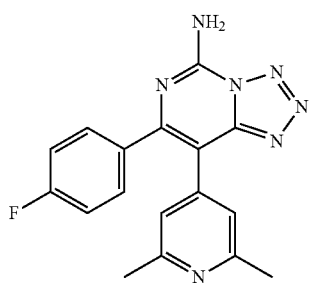 [SMILES: Cc1cc(-c2c(-c3ccc(F)cc3)nc(N)n3nnnc23)cc(C)n1]

Step 14-1, preparation of 8-(2,6-dimethylpyridin-4-yl)-7-(4-fluorophenyl)tetrazolo[1,5-c]pyrimidin-5-amine: The title compound was prepared by using the similar procedure as described in step 13-5, Example 13. The crude product was purified by preparative HPLC using a XBridge Prep OBD C18 150 mm×30 mm×5 m column (eluent: 33% to 63% (v/v) CH$_3$CN and H$_2$O with 10 mmol/L NH$_4$HCO$_3$) to afford the desired product as a white solid. LCMS (M+H)+: 336.1. $^1$H NMR (400 MHz, DMSO-d$_6$) δ 8.58 (s, 2H), 7.43 (dd, J=8.7, 5.6 Hz, 2H), 7.19 (dd, J=10.2, 7.5 Hz, 2H), 6.97 (s, 2H), 2.36 (s, 6H).

Step 16-1, preparation of 8-(2-chloro-6-(trifluoromethyl)pyridin-4-yl)-7-(4-fluorophenyl)tetrazolo[1,5-c]pyrimidin-5-amine: The title compound was prepared by using the similar procedure as described in step 13-5, Example 13. The crude product was purified by preparative HPLC using a XBridge Prep OBD C18 150 mm×30 mm×5 m column (eluent: 19% to 35% (v/v) CH$_3$CN and H$_2$O with 10 mmol/L NH$_4$HCO$_3$) to afford the desired product as a white solid. LCMS (M+H)+: 410.0. $^1$H NMR (300 MHz, DMSO-d$_6$) δ 9.25-8.97 (m, 2H), 7.79 (s, 1H), 7.65 (s, 1H), 7.45 (dd, J=8.8, 5.5 Hz, 2H), 7.25 (t, J=8.8 Hz, 2H).

Example 17: 8-(4-chloroquinolin-6-yl)-7-(4-fluorophenyl)tetrazolo[1,5-c]pyrimidin-5-amine (1-35)

Example 18: 7-(4-fluorophenyl)-8-(4-methylquinolin-6-yl)tetrazolo[1,5-c]pyrimidin-5-amine (1-36)

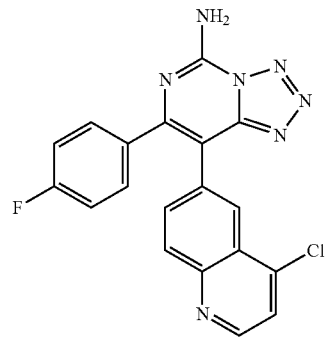 [SMILES: Nc1nc(-c2ccc(F)cc2)c(-c2ccc3nccc(Cl)c3c2)c2nnnn12]

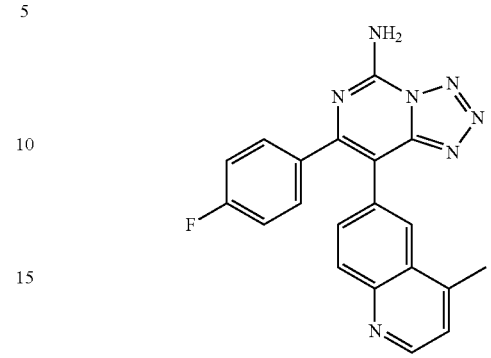

Step 17-1, preparation of 8-(4-chloroquinolin-6-yl)-7-(4-fluorophenyl)tetrazolo[1,5-c]pyrimidin-5-amine: 4-chloro-6-(4,4,5,5-tetramethyl-1,3,2-dioxaborolan-2-yl)quinoline was synthesized starting from 6-bromo-4-chloroquinoline as described in step 7-2, Example 7. The title compound was prepared by using the similar procedure as described in step 13-5, Example 13. The crude product was purified by preparative HPLC using a XBridge Prep OBD C18 150 mm×30 mm×5 m column (eluent: 28% to 53% (v/v) CH$_3$CN and H$_2$O with 10 mmol/L NH$_4$HCO$_3$) to afford the desired product as a white solid. LCMS (M+H)$^+$: 392.0. $^1$H NMR (300 MHz, DMSO-d$_6$) δ 8.93-8.72 (m, 3H), 8.28 (s, 1H), 8.02 (d, J=8.8 Hz, 1H), 7.77 (d, J=4.7 Hz, 1H), 7.68 (dd, J=8.8, 2.0 Hz, 1H), 7.42 (dd, J=8.8, 5.5 Hz, 2H), 7.12 (t, J=8.9 Hz, 2H).

Step 18-1, preparation of 7-(4-fluorophenyl)-8-(4-methylquinolin-6-yl)tetrazolo[1,5-c]pyrimidin-5-amine: The title compound was prepared by using the similar procedure as described in step 13-5, Example 13. The crude product was purified by preparative HPLC using a XBridge Prep OBD C18 150 mm×30 mm×5 m column (eluent: 29% to 51% (v/v) CH$_3$CN and H$_2$O with 10 mmol/L NH$_4$HCO$_3$) to afford the desired product as a white solid. LCMS (M+H)$^+$: 372.0. $^1$H NMR (300 MHz, DMSO-d$_6$) δ 8.82-8.72 (m, 3H), 8.10 (s, 1H), 7.95 (d, J=8.7 Hz, 1H), 7.64 (dd, J=8.7, 1.9 Hz, 1H), 7.50-7.35 (m, 3H), 7.14 (t, J=8.8 Hz, 2H), 2.54-2.51 (m, 3H).

The following compounds were prepared similarly to Example 13 with appropriate substituting reagents and substrates at different steps:

| Cmpd No. | Cmpd Structure | MS (M + H)$^+$ | $^1$H NMR |
|---|---|---|---|
| 1-29 | | 338.1 | (400 MHz, DMSO-d$_6$) δ 8.69 (s, 2H), 7.84 (d, J = 2.6 Hz, 1H), 7.61-7.51 (m, 2H), 7.30-7.19 (m, 2H), 7.10 (dd, J = 9.4, 2.6 Hz, 1H), 6.34 (d, J = 9.4 Hz, 1H), 3.44 (s, 3H). |
| 1-33 | | 356.1 | (300 MHz, DMSO-d$_6$) δ 8.96-8.90 (m, 2H), 7.47-7.37 (m, 2H), 7.27-7.14 (m, 4H), 2.38 (s, 3H). |

| Cmpd No. | Cmpd Structure | MS (M + H)+ | 1H NMR |
|---|---|---|---|
| 1-37 | | 358.1 | (300 MHz, DMSO-d6) δ 8.90 (dd, J = 4.3, 1.7 Hz, 1H), 8.33 (d, J = 8.3 Hz, 1H), 8.06 (s, 1H), 7.93 (d, J = 8.8 Hz, 1H), 7.57-7.50 (m, 2H), 7.43 (dd, J = 8.7, 5.6 Hz, 2H), 7.11 (t, J = 8.9 Hz, 2H). –NH2 was not observed. |
| 1-41 | | 367.0 | (300 MHz, Methanol-d4) δ 7.82 (s, 1H), 7.73 (s, 1H), 7.65-7.48 (m, 2H), 7.11 (t, J = 8.9 Hz, 2H). |
| 1-42 | | 347.1 | (300 MHz, Methanol-d4) δ 8.22 (s, 1H), 7.71-.58 (m, 2H), 7.54-7.43 (m, 2H), 7.18-7.26 (m, 1H), 6.91 (t, J = 8.8 Hz, 2H). |
| 1-52 | | 368.0 | (300 MHz, DMSO-d6) δ 8.75 (s, 2H), 8.23 (s, 1H), 7.75 (d, J = 8.4 Hz, 2H), 7.63 (s, 1H), 7.51-7.45 (m, 3H), 6.94 (d, J = 8.4 Hz, 1H), 3.78 (s, 3H). |

| Cmpd No. | Cmpd Structure | MS (M + H)+ | 1H NMR |
|---|---|---|---|
| 1-57 | | 373.0 | (300 MHz, DMSO-$d_6$) δ 8.64 (bs, 2 H), 8.35 (s, 1H), 7.53-7.35 (m, 4H), 7.00-6.84 (m, 3H), 3.74 (s, 3H), 2.39 (s, 3H). |
| 1-58 | | 372.1 | (300 MHz, DMSO-$d_6$) δ 8.93 (bs, 2H), 7.49-7.35 (m, 3H), 7.31 (s, 1H), 7.24-7.17 (m, 2H), 6.86 (t, J = 55.0 Hz, 1H), 3.36 (s, 3H). |
| 1-59 | | 421.8 | (400 MHz, DMSO-$d_6$) δ 9.06 (bs, 2H), 7.81 (s, 1H), 7.68 (s, 1H), 7.37 (d, J = 8.8 Hz, 2H), 6.97 (d, J = 8.8 Hz, 2H), 3.78 (s, 3H). |

Biological Data

Example A: Adenosine A2a Receptor Whole Cell Cyclic AMP Assay

Stably transfected HEK293 cells expressing the human adenosine A2a receptor were maintained in Dulbecco's Modified Eagle Medium (DMEM) supplemented with 10% FBS and 500 μg/mL Geneticin (Invitrogen) at 37° C., 10% $CO_2$. On day 1, 384-well plates were seeded with 50 μL of cells at 40,000 cells/mL for a total of 2,000 cells per well and incubated overnight at 37° C., 10% $CO_2$. On day 2, cells were refed with culture medium without FBS and Geneticin. Following 2-hour serum starvation, cells were treated with test compound for 1 hour in the presence of 1 μM, 10 μM, or 100 μM of adenosine. For dose-response and determination of $IC_{50}$, cells were incubated with 11 test compound concentrations (3-fold serial dilution from 10 μM to 169 μM). After compound treatment, cAMP levels in the treated cells were measured using cAMP-GS Dynamic kit (Cisbio) utilizing the FRET (Fluorescence Resonance Energy Transfer) technology. Briefly, detection reagents, d2-labeled cAMP conjugate (acceptor) and cryptate-labeled anti-cAMP antibody (donor) were added to each well and incubated for 60 min at room temperature. Following incubation, 18 μL of supernatant were transferred to ProxiPlate-384 Plus (Perkin Elmer). The fluorescence intensity was measured using CLARIOstar$^{plus}$ (BMG Labtech) at emission of 665 nm and 615 nm with excitation at 350 nm and the fluorescence ratio 665/620 was calculated. IC50 was determined by fitting the dose-response data to a four-parameter logistic curve using GraphPad Prism.

Example B: Adenosine A2b Receptor Whole Cell Cyclic AMP Assay

HEK293 cells were maintained in DMEM supplemented with 10% FBS at 37° C., 10% $CO_2$. On day 1, 4×10$^6$ cells were plated in 10 cm dish. On day 2, cells were transfected with plasmid expressing human adenosine A2b receptor using Lipofectamine 2000 (Invitrogen) following manufacturer's protocol. On day 3, 384-well plates were seeded with 50 μL of cells at 80,000 cells/mL for a total of 4,000 cells per well and incubated overnight at 37° C., 10% $CO_2$. On day 4, cells were refed with culture medium without FBS. Following 2-hour serum starvation, cells were treated with test compound for 1 hour in the presence of 1 μM, 10 μM, or 100 μM of adenosine. For dose-response and determination of IC50, cells were incubated with 11 test compound concentrations (3-fold serial dilution from 10 μM to 169 μM). After compound treatment, cAMP levels in the treated cells were measured using cAMP-GS Dynamic kit (Cisbio) utilizing the FRET (Fluorescence Resonance Energy Transfer) technology. Briefly, detection reagents, d2-labeled cAMP conjugate (acceptor) and cryptate-labeled anti-cAMP antibody (donor) were added to each well and incubated for 60 min at room temperature. Following incubation, 18 μL of supernatant were transferred to ProxiPlate-384 Plus (Perkin Elmer). The fluorescence intensity was measured using CLARIOstar$^{plus}$ (BMG Labtech) at emission of 665 nm and 615 nm with excitation at 350 nm and the fluorescence ratio 665/620 was calculated. IC50 was determined by fitting the dose-response data to a four-parameter logistic curve using GraphPad Prism.

The A2a cAMP $IC_{50}$ data at 1 μM and 100 μM of Adenosine and A2b cAMP $IC_{50}$ data at 10 μM of Adenosine are provided in Table 2. The symbol "+" indicates A2a or A2b $IC_{50}$ is greater than 1 μM. "++" indicates A2a or A2b $IC_{50}$>100 nM but ≤1 μM. "+++" indicates A2a or A2b $IC_{50}$≤100 nM. "NR" indicates A2a or A2b mean inhibition is <25% at the top concentration. Cells with no symbol indicates the $IC_{50}$ was not determined. Herein, the $IC_{50}$ data of comparative compounds (e.g., AZD4635, CPJ-444, AB928, SEL330-639, EOS-805) were determined by in-house assay.

TABLE 2

| Cmpd ID/No. | A2a @ 1 μM Adenosine | A2a @ 100 μM Adenosine | A2b @ 10 μM Adenosine |
| --- | --- | --- | --- |
| AZD4635[a] | ++ | NR | NR |
| CPI-444[b] | + | NR | NR |
| AB928[c] | ++ | + | + |
| SEL330-639[d] | ++ | + | NR |
| EOS-805[e] | ++ | + | NR |
| 1-1 | ++ | | |
| 1-2 | + | | |
| 1-3 | + | | |
| 1-4 | + | | |
| 1-5 | ++ | | |
| 1-6 | +++ | ++ (partial) | NR |
| 1-7 | +++ | ++ | ++ |
| 1-8 | + | | |
| 1-9 | ++ | NR | |
| 1-10 | ++ | + (partial) | |
| 1-11 | +++ | NR | |
| 1-12 | ++ | NR | |
| 1-13 | +++ | ++ | ++ |
| 1-14 | ++ | NR | |
| 1-15 | ++ | NR | |
| 1-16 | ++ | NR | |
| 1-17 | ++ | NR | |
| 1-18 | + | NR | |
| 1-19 | ++ | + | |
| 1-20 | +++ | + | ++ |
| 1-21 | + | NR | |
| 1-22 | +++ | NR | |
| 1-23 | +++ | ++ (partial) | |
| 1-24 | ++ | ++ | |
| 1-25 | +++ | ++ | ++ |
| 1-26 | ++ | | |
| 1-27 | ++ | | |
| 1-28 | +++ | NR | + (partial) |
| 1-29 | ++ | | |
| 1-30 | +++ | | |
| 1-31 | ++ | | |
| 1-32 | ++ | | |
| 1-33 | ++ | | |
| 1-34 | ++ | + | NR |
| 1-35 | +++ | | |
| 1-36 | +++ | | ++ |
| 1-37 | ++ | | |
| 1-38 | ++ | | NR |
| 1-39 | +++ (partial) | | |
| 1-40 | +++ (partial) | | |
| 1-41 | ++ | | |
| 1-42 | ++ | | |
| 1-43 | +++ | NR | NR |
| 1-44 | +++ | | |
| 1-45 | ++ | | |
| 1-46 | ++ | | |
| 1-47 | ++ | | |
| 1-48 | ++ | ++ | ++ |
| 1-49 | ++ | | |
| 1-50 | +++ (partial) | | |
| 1-51 | ++ | | |
| 1-52 | ++ | | |
| 1-53 | +++ | NR | |
| 1-54 | ++ | NR | |
| 1-55 | ++ | NR | |
| 1-56 | ++ | + | |
| 1-57 | ++ | + | ++ |
| 1-58 | ++ | + | |
| 1-59 | ++ | + | |

[a]Cayman, cat. # 26322,
[b]MCE, cat. # HY-101978,
[c]MCE, cat. # HY-129393,
[d]Int. Immunopharmacol. 2021, 96, 107645,
[e]MCE, cat. # HY-137442

The disclosures of each and every patent, patent application, and publication cited herein are hereby incorporated herein by reference in their entireties.

What is claimed is:

1. A compound of Formula (I):

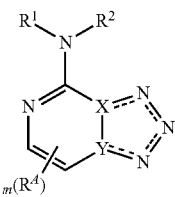

or a pharmaceutically acceptable salt thereof, wherein:

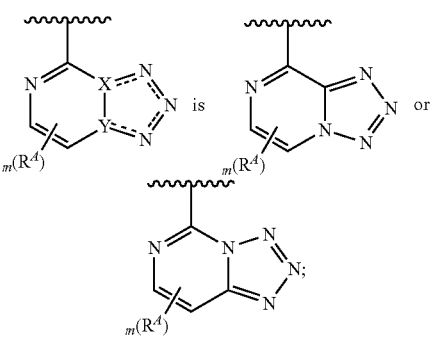

(i) $R^1$ is H, C1-C4 alkyl, C1-C4 haloalkyl, C2-C4 alkenyl, C2-C4 alkynyl, C3-C6 cycloalkyl, or 4- to 7-membered heterocyclyl; and
$R^2$ is H, C1-C4 alkyl, C1-C4 haloalkyl, C2-C4 alkenyl, C2-C4 alkynyl, C3-C6 cycloalkyl, or 4- to 7-membered heterocyclyl; or (ii) R¹ is H; and
R², taken together with the nitrogen atom to which it is attached, forms an (acyloxy)C1-C6 alkyl carbamate or an (oxodioxolenyl)methyl carbamate; or
(iii) R¹, taken together with the nitrogen atom to which it is attached, forms an (acyloxy)C1-C6 alkyl carbamate or an (oxodioxolenyl)methyl carbamate; and R² is H:
each R$^A$ is independently C5-C7 cycloalkyl, 4- to 7-membered heterocyclyl, phenyl, or 5- to 10-membered heteroaryl, wherein each C5-C7 cycloalkyl, 4- to 7-membered heterocyclyl, phenyl, and 5- to 10-membered heteroaryl is optionally and independently substituted with 1, 2, or 3 independently selected R³ substituents;
each R³ is independently halogen, CN, —OR⁴, —NR⁴R⁵, —C(=O)R$^{4A}$, —C(=O)OR$^{4B}$, —C(=O)NR⁴R⁵, —SR⁴, —S(=O)R$^{4A}$, —S(=O)₂R$^{4A}$, —NO₂, —OC(=O)R$^{4A}$, —OC(=O)NR⁴R⁵, —S(=O)NR⁴R⁵, —S(=O)₂NR⁴R⁵, —NR⁴C(=O)NR⁴R⁵, —NR⁴C(=O)R$^{4A}$, —NR⁴C(=O)OR$^{4A}$, —NR⁴S(=O)R$^{4A}$, —NR⁴S(=O)₂R$^{4A}$, C1-C6 haloalkyl, C2-C6 alkenyl, C2-C6-alkynyl, C3-C6 cycloalkyl, C1-C6 alkyl, wherein each C1-C6 alkyl is optionally and independently substituted with 1 -OH substituent;
each R⁴ is independently H, C1-C6 alkyl, C1-C6 haloalkyl, C3-C6 cycloalkyl, C2-C6 alkenyl, C2-C6-alkynyl, or —C(=O)R⁶;
each R$^{4A}$ is independently C1-C6 alkyl, C1-C6 haloalkyl, C2-C6 alkenyl, C2-C6-alkynyl, or C3-C6 cycloalkyl;
each R$^{4B}$ is independently hydrogen, C1-C6 alkyl, C1-C6 haloalkyl, C2-C6 alkenyl, C2-C6-alkynyl, or C3-C6 cycloalkyl;
each R⁵ is independently H, C1-C6 alkyl, C1-C6 haloalkyl, C3-C6 cycloalkyl, C2-C6 alkenyl, C2-C6-alkynyl, or —C(=O)R⁶;
each R⁶ is independently C1-C6 alkyl, C1-C6 haloalkyl, C2-C6 alkenyl, C2-C6-alkynyl, or C3-C6 cycloalkyl; and
m is 2.

2. The compound of claim 1, or a pharmaceutically acceptable salt thereof, wherein:

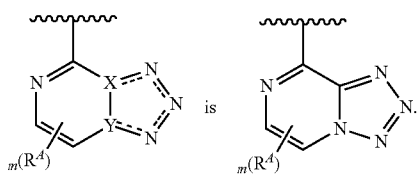

is

3. The compound of claim 1, or a pharmaceutically acceptable salt thereof, wherein:

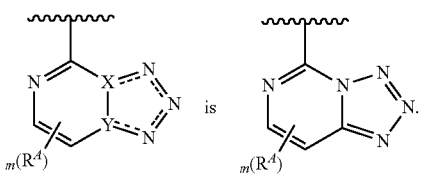

is

4. The compound of claim 1, or a pharmaceutically acceptable salt thereof, wherein R¹ is H; and
R² is H.

5. The compound of claim 1, or a pharmaceutically acceptable salt thereof, wherein:
R¹ is C1-C4 alkyl; and
R² is C1-C4 alkyl.

6. The compound of claim 1, or a pharmaceutically acceptable salt thereof, wherein each R$^A$ is the same.

7. The compound of claim 1, or a pharmaceutically acceptable salt thereof, wherein each R$^A$ is different.

8. The compound of claim 1, or a pharmaceutically acceptable salt thereof, wherein each R$^A$ is independently 4- to 7-membered heterocyclyl, wherein each 4- to 7-membered heterocyclyl is optionally and independently substituted with 1, 2, or 3 independently selected R³ substituents.

9. The compound of claim 1, or a pharmaceutically acceptable salt thereof, wherein:
one R$^A$ is phenyl or 6-membered heteroaryl, wherein the phenyl or 6-membered heteroaryl is substituted with 1 or 2 independently selected R³ substituents; and
the other R$^A$ is 6- to 10-membered heteroaryl, wherein the 6- to 10-membered heteroaryl is substituted with 1 or 2 independently selected R³ substituents.

10. The compound of claim 1, or a pharmaceutically acceptable salt thereof, wherein each R$^A$ is independently phenyl or 5- to 10-membered heteroaryl, wherein each phenyl and 5- to 10-membered heteroaryl is optionally and independently substituted with 1, 2, or 3 independently selected R³ substituents.

11. The compound of claim 10, or a pharmaceutically acceptable salt thereof, wherein each R$^A$ is independently phenyl, wherein each phenyl is optionally and independently substituted with 1, 2, or 3 independently selected R³ substituents.

12. The compound of claim 10, or a pharmaceutically acceptable salt thereof, wherein each R$^A$ is independently 5- to 10-membered heteroaryl, wherein each 5- to 10-membered heteroaryl is optionally and independently substituted with 1, 2, or 3 independently selected R³ substituents.

13. The compound of claim 1, or a pharmaceutically acceptable salt thereof, wherein one R$^A$ is selected from:

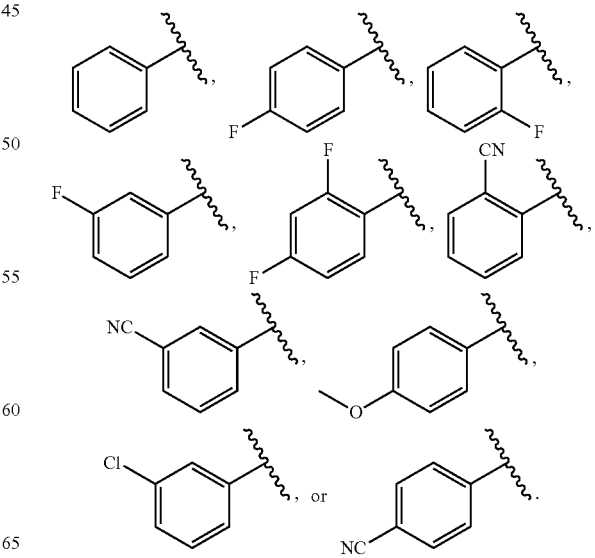

14. The compound of claim 1, or a pharmaceutically acceptable salt thereof, wherein one $R^A$ is selected from:
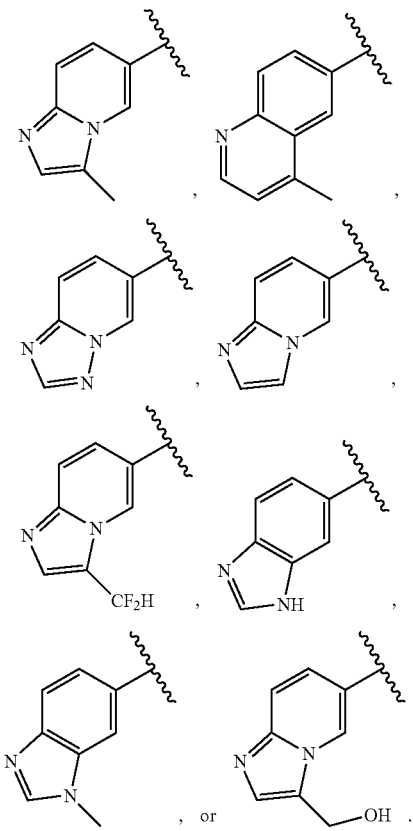
, or .
15. The compound of claim 1, or a pharmaceutically acceptable salt thereof, wherein each $R^A$ is independently selected from:
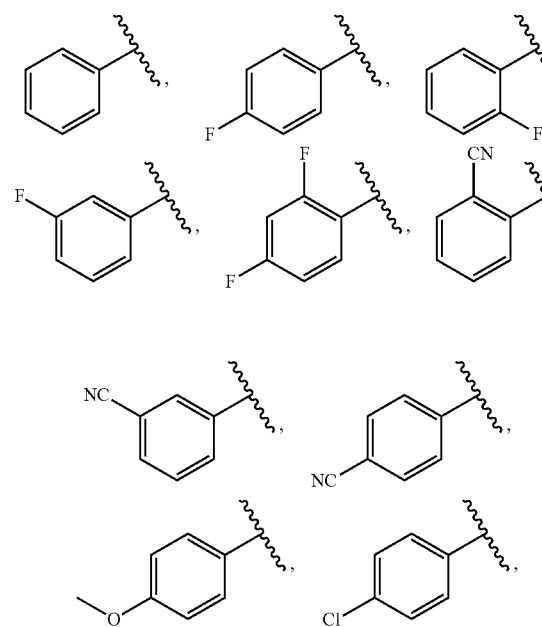
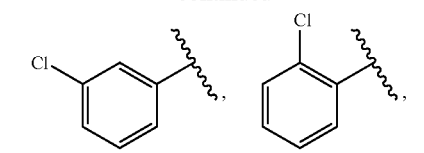
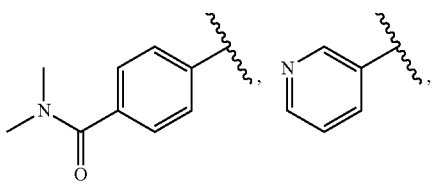
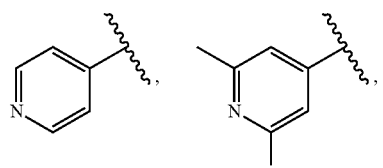
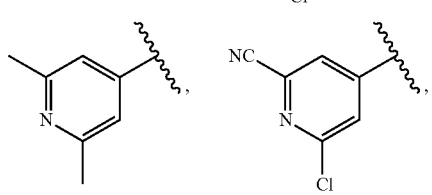
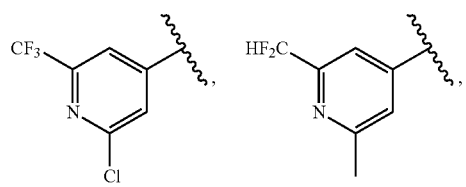
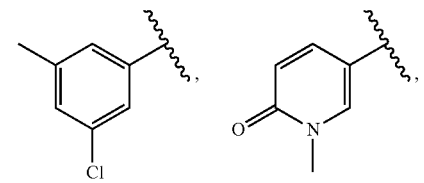
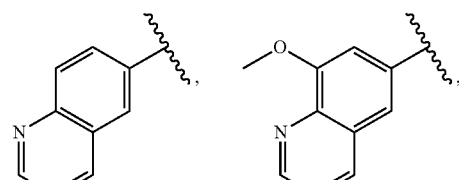
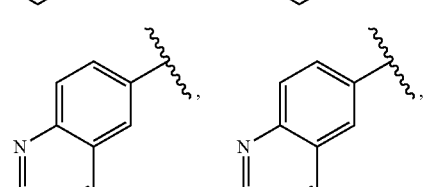
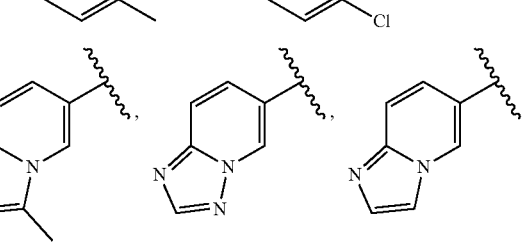

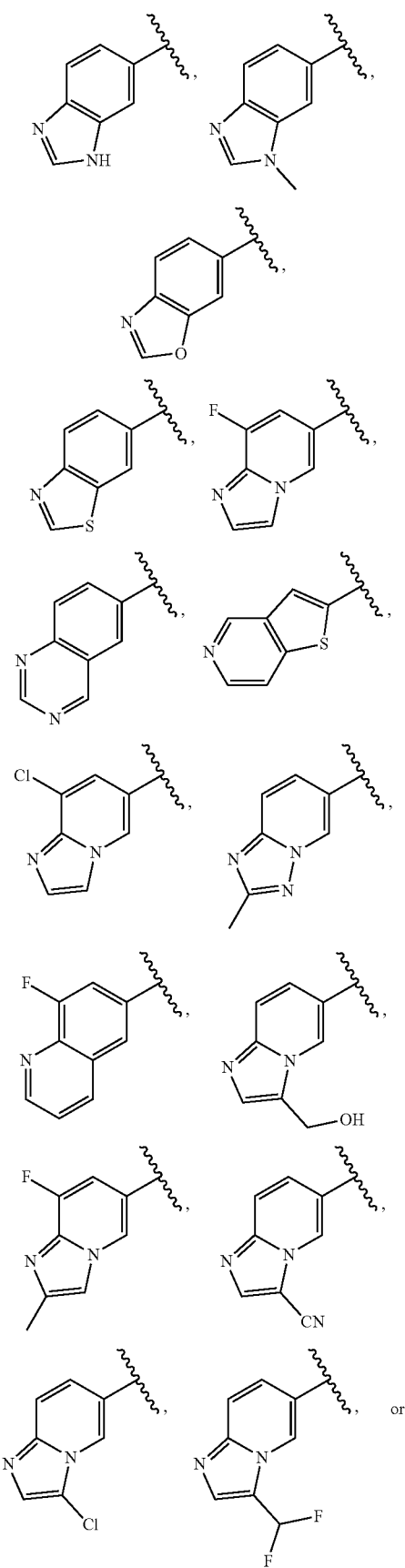
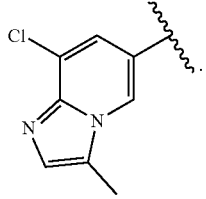

16. The compound of claim 1, or a pharmaceutically acceptable salt thereof, wherein each $R^3$ is independently C1-C3 alkyl, C1-C3 haloalkyl, —OCH$_3$, F, Cl, or CN, wherein each C1-C3 alkyl is optionally and independently substituted with 1 -OH substituent.

17. The compound of claim 1, wherein the compound is selected from the group consisting of: 5-(2-chloro-6-methylpyridin-4-yl)-6-(4-fluorophenyl)tetrazolo[1,5-a]pyrazin-8-amine, 6-(2-chloro-6-methylpyridin-4-yl)-5-(4-fluorophenyl)tetrazolo[1,5-a]pyrazin-8-amine, 5-(3-chloro-5-methylphenyl)-6-(4-fluorophenyl)tetrazolo[1,5-a]pyrazin-8-amine, 5-(8-amino-6-(4-fluorophenyl)tetrazolo[1,5-a]pyrazin-5-yl)-1-methylpyridin-2(1H)-one, 6-(4-fluorophenyl)-5-(8-methoxyquinolin-6-yl)tetrazolo[1,5-a]pyrazin-8-amine, 6-(4-fluorophenyl)-5-(4-methylquinolin-6-yl)tetrazolo[1,5-a]pyrazin-8-amine, 6-(4-fluorophenyl)-5-(3-methylimidazo[1,2-a]pyridin-6-yl)tetrazolo[1,5-a]pyrazin-8-amine, 5-([1,2,4]triazolo[1,5-a]pyridin-6-yl)-6-(4-fluorophenyl)tetrazolo[1,5-a]pyrazin-8-amine, 6-(4-fluorophenyl)-5-(imidazo[1,2-a]pyridin-6-yl)tetrazolo[1,5-a]pyrazin-8-amine, 5-(benzo[d]oxazol-6-yl)-6-(4-fluorophenyl)tetrazolo[1,5-a]pyrazin-8-amine, 6-(4-fluorophenyl)-5-(quinolin-6-yl)tetrazolo[1,5-a]pyrazin-8-amine, 5-(benzo[d]thiazol-6-yl)-6-(4-fluorophenyl)tetrazolo[1,5-a]pyrazin-8-amine, 6-(4-fluorophenyl)-5-(1-methyl-1H-benzo[d]imidazol-6-yl)tetrazolo[1,5-a]pyrazin-8-amine, 5-(8-fluoroimidazo[1,2-a]pyridin-6-yl)-6-(4-fluorophenyl)tetrazolo[1,5-a]pyrazin-8-amine, 6-(4-fluorophenyl)-5-(quinazolin-6-yl)tetrazolo[1,5-a]pyrazin-8-amine, 6-(4-fluorophenyl)-5-(thieno[3,2-c]pyridin-2-yl)tetrazolo[1,5-a]pyrazin-8-amine, 5-(8-chloroimidazo[1,2-a]pyridin-6-yl)-6-(4-fluorophenyl)tetrazolo[1,5-a]pyrazin-8-amine, 6-(4-fluorophenyl)-5-(2-methyl-[1,2,4]triazolo[1,5-a]pyridin-6-yl)tetrazolo[1,5-a]pyrazin-8-amine, 6-(4-fluorophenyl)-5-(8-fluoroquinolin-6-yl)tetrazolo[1,5-a]pyrazin-8-amine, (6-(8-amino-6-(4-fluorophenyl)tetrazolo[1,5-a]pyrazin-5-yl)imidazo[1,2-a]pyridin-3-yl)methanol, 5-(8-fluoro-2-methylimidazo[1,2-a]pyridin-6-yl)-6-(4-fluorophenyl)tetrazolo[1,5-a]pyrazin-8-amine, 6-(8-amino-6-(4-fluorophenyl)tetrazolo[1,5-a]pyrazin-5-yl)imidazo[1,2-a]pyridine-3-carbonitrile, 5-(3-chloroimidazo[1,2-a]pyridin-6-yl)-6-(4-fluorophenyl)tetrazolo[1,5-a]pyrazin-8-amine, 5-(8-chloro-3-methylimidazo[1,2-a]pyridin-6-yl)-6-(4-fluorophenyl)tetrazolo[1,5-a]pyrazin-8-amine, 7-(4-fluorophenyl)-8-(3-methylimidazo[1,2-a]pyridin-6-yl)tetrazolo[1,5-c]pyrimidin-5-amine, 5-(2-chloro-6-methylpyridin-4-yl)-6-(2-fluorophenyl)tetrazolo[1,5-a]pyrazin-8-amine, 5-(2-chloro-6-methylpyridin-4-yl)-6-(3-fluorophenyl)tetrazolo[1,5-a]pyrazin-8-amine, 8-(2,6-dimethylpyridin-4-yl)-7-(4-fluorophenyl)tetrazolo[1,5-c]pyrimidin-5-amine, 5-(5-amino-7-(4-fluorophenyl)tetrazolo[1,5-c]pyrimidin-8-yl)-1-methylpyridin-2(1H)-one, 7-(4-fluorophenyl)-8-(1-methyl-1H-benzo[d]imidazol-6-yl)tetrazolo[1,5-c]pyrimidin-5-amine, 3-(8-amino-5-(4-methylquinolin-6-yl)tetrazolo[1,5-a]pyrazin-6-yl)benzonitrile, 5-(2-chloro-6-methylpyridin-4-yl)-6-phenyltetrazolo[1,5-a]pyrazin-8-amine, 8-(2-chloro-6- methylpyridin-4-yl)-7-(4-fluorophenyl)tetrazolo[1,5-c]pyrimidin-5-amine, 8-(2-chloro-6-(trifluoromethyl)pyridin-4-yl)-7-(4-fluorophenyl)tetrazolo[1,5-c]pyrimidin-5-amine, 8-(4-chloroquinolin-6-yl)-7-(4-fluorophenyl)tetrazolo[1,5-c]pyrimidin-5-amine, 7-(4-fluorophenyl)-8-(4-methylquinolin-6-yl)tetrazolo[1,5-c]pyrimidin-5-amine, 7-(4-fluorophenyl)-8-(quinolin-6-yl)tetrazolo[1,5-c]pyrimidin-5-amine, 6-(2,4-difluorophenyl)-5-(4-methylquinolin-6-yl)tetrazolo[1,5-a]pyrazin-8-amine, 4-(8-amino-5-(4-methylquinolin-6-yl)tetrazolo[1,5-a]pyrazin-6-yl)benzonitrile, 6-(4-methoxyphenyl)-5-(4-methylquinolin-6-yl)tetrazolo[1,5-a]pyrazin-8-amine, 6-(4-chlorophenyl)-5-(4-methylquinolin-6-yl)tetrazolo[1,5-a]pyrazin-8-amine, 6-(2-chlorophenyl)-5-(4-methylquinolin-6-yl)tetrazolo[1,5-a]pyrazin-8-amine, 5-(4-methylquinolin-6-yl)-6-(pyridin-3-yl)tetrazolo[1,5-a]pyrazin-8-amine, 5-(4-methylquinolin-6-yl)-6-(pyridin-4-yl)tetrazolo[1,5-a]pyrazin-8-amine, 4-(8-amino-5-(4-methylquinolin-6-yl)tetrazolo[1,5-a]pyrazin-6-yl)-N,N-dimethylbenzamide, 4-(5-amino-7-(4-fluorophenyl)tetrazolo[1,5-c]pyrimidin-8-yl)-6-chloropicolinonitrile, 8-(1H-benzo[d]imidazol-6-yl)-7-(4-fluorophenyl)tetrazolo[1,5-c]pyrimidin-5-amine, 5-(3-(difluoromethyl)imidazo[1,2-a]pyridin-6-yl)-6-(4-fluorophenyl)tetrazolo[1,5-a]pyrazin-8-amine, 2-(8-amino-5-(4-methylquinolin-6-yl)tetrazolo[1,5-a]pyrazin-6-yl)benzonitrile, 6-(3-chlorophenyl)-5-(4-methylquinolin-6-yl)tetrazolo[1,5-a]pyrazin-8-amine, 4-(8-amino-5-(3-methylimidazo[1,2-a]pyridin-6-yl)tetrazolo[1,5-a]pyrazin-6-yl)benzonitrile, 5-(2-(difluoromethyl)-6-methylpyridin-4-yl)-6-(4-fluorophenyl)tetrazolo[1,5-a]pyrazin-8-amine, 6-(4-methoxyphenyl)-5-(1-methyl-1H-benzo[d]imidazol-6-yl)tetrazolo[1,5-a]pyrazin-8-amine, 5-(2-chloro-6-(trifluoromethyl)pyridin-4-yl)-6-(4-fluorophenyl)tetrazolo[1,5-a]pyrazin-8-amine, 6-(4-methoxyphenyl)-5-(3-methylimidazo[1,2-a]pyridin-6-yl)tetrazolo[1,5-a]pyrazin-8-amine, 4-(5-amino-8-(1-methyl-1H-benzo[d]imidazol-6-yl)tetrazolo[1,5-c]pyrimidin-7-yl)benzonitrile, 7-(4-methoxyphenyl)-8-(3-methylimidazo[1,2-a]pyridin-6-yl)tetrazolo[1,5-c]pyrimidin-5-amine, 8-(2-(difluoromethyl)-6-methylpyridin-4-yl)-7-(4-fluorophenyl)tetrazolo[1,5-c]pyrimidin-5-amine, and 8-(2-chloro-6-(trifluoromethyl)pyridin-4-yl)-7-(4-methoxyphenyl)tetrazolo[1,5-c]pyrimidin-5-amine, or a pharmaceutically acceptable salt thereof.

18. A pharmaceutical composition comprising a pharmaceutically acceptable excipient and the compound of claim 1, or a pharmaceutically acceptable salt thereof.

* * * * *

UNITED STATES PATENT AND TRADEMARK OFFICE
CERTIFICATE OF CORRECTION

PATENT NO. : 12,065,444 B2
APPLICATION NO. : 17/989584
DATED : August 20, 2024
INVENTOR(S) : Sangdon Han It is certified that error appears in the above-identified patent and that said Letters Patent is hereby corrected as shown below:

In the Specification

In Column 1, Line 44, delete "homeostatis," and insert -- homeostasis, --, therefor.

In Column 2, Line 28, delete "—NR$^4$S(=O)R$^{4A}$" and insert -- —NR$^4$S(=O)R$^{4A}$, --, therefor.

In Column 4, Line 13, delete "R$^2$" and insert -- R$^1$ --, therefor.

In Column 4, Line 31, delete "R$^1$" and insert -- R$^2$ --, therefor.

In Column 11, Lines 20-25, delete " 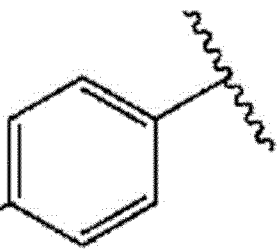 " and insert -- 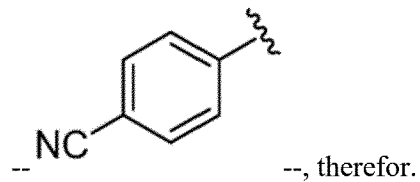 --, therefor.

Signed and Sealed this
Thirty-first Day of December, 2024

Derrick Brent
*Acting Director of the United States Patent and Trademark Office*

In Column 12, Line 28, delete "—N⁴CO₂R⁴ᴬ," and insert -- —NR⁴CO₂R⁴ᴬ, --, therefor.

In Column 19, Line 60, delete " 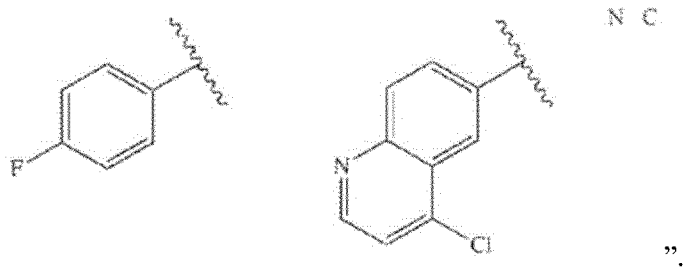 ".

In Column 31, Line 32, delete ""about."""" and insert -- "about." --, therefor.

In Column 32, Line 31, delete "azirldinyl," and insert -- aziridinyl, --, therefor.

In Column 32, Line 33, delete "imidazolinyl," and insert -- imidazolidinyl, --, therefor.

In Column 32, Line 36, delete ""oxazolidinyt," and insert -- oxazolidinyl, --, therefor.

In Column 32, Line 37, delete ""pyrazolidinyl." and insert -- pyrazolidinyl, --, therefor.

In Column 32, Line 38, delete "pyrrotidinyl," and insert -- pyrrolidinyl, --, therefor.

In Column 35, Line 58, delete " 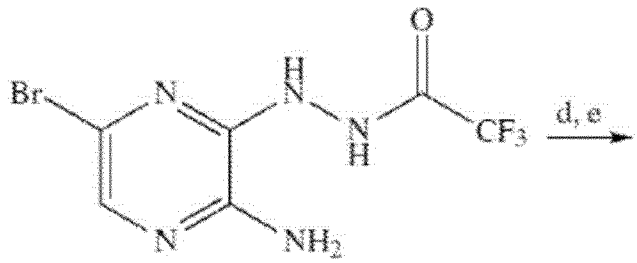 " and insert -- 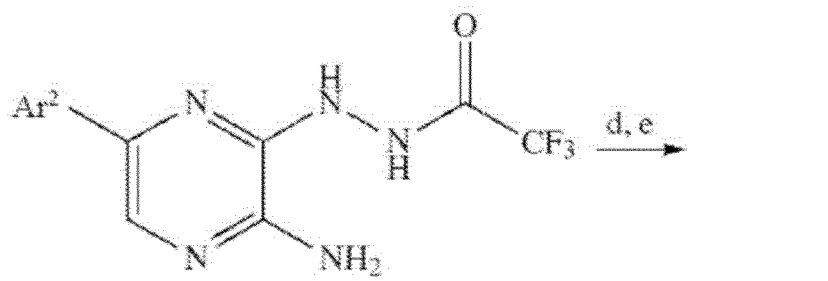 --, therefor.

In Column 36, Lines 49-50, delete "a) Ar²M, Pd, base, b) NH₂NH₂ EtOH, b) (CF₃CO)₂O, d) NBS, e) HCl, f) NaNO₂, AcOH" and insert -- a) Ar²M, Pd, base, b) NH₂NH₂ EtOH, c) (CF₃CO)₂O, d) NBS, e) HCl, f) NaNO₂, AcOH --, therefor.

CERTIFICATE OF CORRECTION (continued)
U.S. Pat. No. 12,065,444 B2

In Column 39, Line 18, delete "tri-tert-buytlphosphine;" and insert -- tri-tert-butylphosphine; --, therefor.

In Column 39, Line 46, delete "EDCI" and insert -- EDCI: --, therefor.

In Column 41, Line 15, delete "(M+H)$^{30}$:" and insert -- (M+H)$^+$: --, therefor.

In Column 42, Line 19, delete "4700" and insert -- 47% --, therefor.

In Column 42, Line 22, delete "(M+H):" and insert -- (M+H)+: --, therefor.

In Column 42, Line 24, "(i, 2H)," and insert -- (m, 2H), --, therefor.

In Column 45, Line 5, delete " 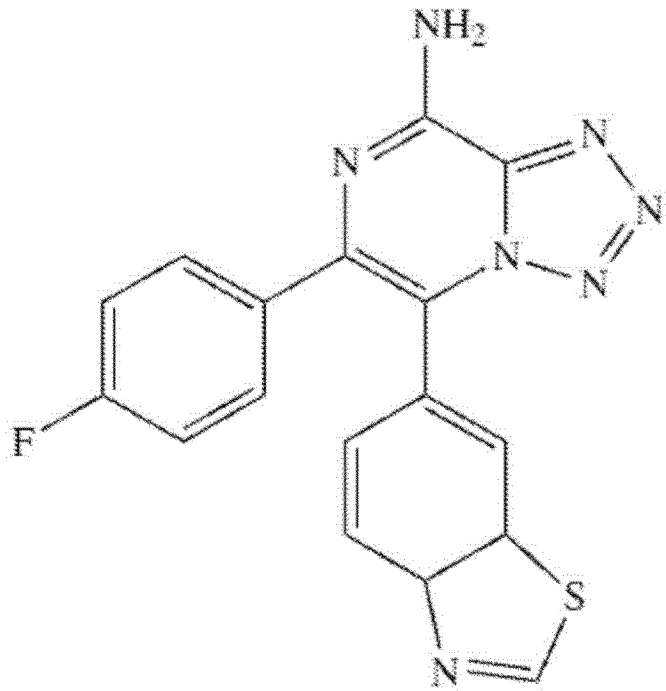 " and insert

CERTIFICATE OF CORRECTION (continued)
U.S. Pat. No. 12,065,444 B2

Page 4 of 5

-- 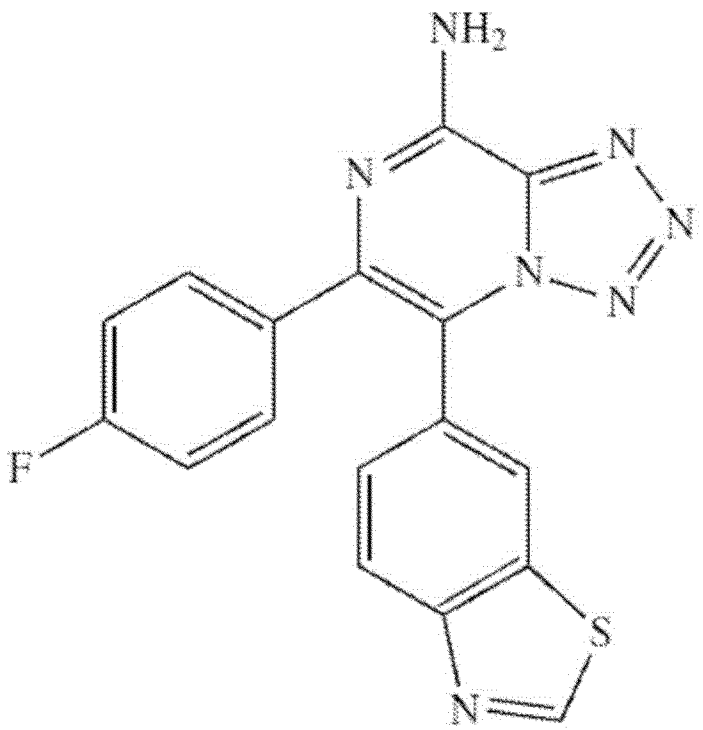 --, therefor.

In Columns 47-48, Line 8, after "2H)" insert -- . --.

In Column 57, Line 61, delete "m" and insert -- μm --, therefor.

In Column 57, Line 64, delete "(M+H)30:" and insert -- (M+H)+: --, therefor.

In Column 59, Line 1, delete "m" and insert -- μm --, therefor.

In Column 59, Line 35, delete "m" and insert -- μm --, therefor.

In Column 59, Line 67, delete "m" and insert -- μm --, therefor.

In Column 61, Line 22, delete "m" and insert -- μm --, therefor.

In Column 61, Line 62, delete "m" and insert -- μm --, therefor.

In Column 62, Line 29, delete "m" and insert -- μm --, therefor.

In Column 62, Line 63, delete "m" and insert -- μm --, therefor.

In Column 63, Line 25, delete "m" and insert -- μm --, therefor.

In Column 63, Line 61, delete "m" and insert -- μm --, therefor.

In Column 65, Line 25, delete "m" and insert -- µm --, therefor.

In Column 65, Line 62, delete "m" and insert -- µm --, therefor.

In Column 66, Line 26, delete "m" and insert -- µm --, therefor.

In Column 66, Line 62, delete "m" and insert -- µm --, therefor.

In Column 67, Line 28, delete "m" and insert -- µm --, therefor.

In Column 68, Line 25, delete "m" and insert -- µm --, therefor.

In Column 73, Line 25, delete "CPJ-444" and insert -- CPI-444 --, therefor.

In the Claims

Claim 1: In Column 75, Line 9, delete "H:" and insert -- H; --, therefor.

Claim 9: In Column 76, Line 22, after "is" insert -- a --.